US012650428B2

(12) United States Patent
Ng et al.

(10) Patent No.: US 12,650,428 B2
(45) Date of Patent: Jun. 9, 2026

(54) NEUTROPHIL PROGENITORS AND RELATED METHODS AND USES

(71) Applicant: Agency for Science, Technology and Research, Singapore (SG)

(72) Inventors: Lai Guan Ng, Singapore (SG); Immanuel Weng Han Kwok, Singapore (SG); De Li Leonard Tan, Singapore (SG); Florent Ginhoux, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 720 days.

(21) Appl. No.: 18/000,559

(22) PCT Filed: Jun. 11, 2021

(86) PCT No.: PCT/SG2021/050342
§ 371 (c)(1),
(2) Date: Dec. 2, 2022

(87) PCT Pub. No.: WO2021/251908
PCT Pub. Date: Dec. 16, 2021

(65) Prior Publication Data
US 2023/0213513 A1 Jul. 6, 2023

(30) Foreign Application Priority Data
Jun. 12, 2020 (SG) ............................ 10202005589P

(51) Int. Cl.
*G01N 33/569* (2006.01)
*A61K 35/15* (2025.01)

(52) U.S. Cl.
CPC ....... *G01N 33/56972* (2013.01); *A61K 35/15* (2013.01); *G01N 2333/705* (2013.01)

(58) Field of Classification Search
CPC ....... G01N 33/56972; G01N 2333/705; G01N 33/5005; A61K 35/15; C12N 2501/22; C12N 5/0642; A61P 7/00
See application file for complete search history.

(56) References Cited

FOREIGN PATENT DOCUMENTS

WO 2018/187786 A1 10/2018
WO 2019/147187 A1 8/2019

OTHER PUBLICATIONS

Zhu et al. Identification of an Early Unipotent Neutrophil Progenitor with Pro-tumoral Activity in Mouse and Human Bone Marrow. 2018, Cell Reports 24, 2329-2341. (Year: 2018).*
Lochem et al. Immunophenotypic Differentiation Patterns of Normal Hematopoiesis in Human Bone Marrow: Reference Patterns for Age-Related Changes and Disease-Induced Shifts. Cytometry Part B (Clinical Cytometry) 60B:1-13 (2004) (Year: 2004).*
Deniset, J. F. et al: "Neutrophil heterogeneity: Bona fide subsets or polarization states?", Journal of Leukocyte Biology, vol. 103, No. 5, May 1, 2018 (May 1, 2018), pp. 829-838.
International Preliminary Report on Patentability for International Application No. PCTSG2021/050342 "Neutrophil Progenitors and Related Methods and Uses" date of issuance: Dec. 13, 2022.
Supplementary Partial European Search Report for EP Application No. 21821870, "Neutrophil Progenitors and Related Methods and Uses" date: Jul. 8, 2024.
Notification of Transmittal of the International Search Report and the Written Opinion of the International Searching Authority, or the Declaration for International Application No. PCTSG2021/050342 "Neutrophil Progenitors and Related Methods and Uses" dated Sep. 13, 2021.
Dinh, H.Q., et al., "Coexpression of CD71 and CD117 identifies an early unipotent neutrophil progenitor population in human bone marrow", Immunity, Aug. 18, 2020; 52(2): 319-334.
Kwok, I., et al., "Combinatorial Single-Cell Analyses of Granulocyte-Monocyte Progenitor Heterogeneity Reveals an Early Uni-potent Neutrophil Progenitor", 2020, Immunity 53, 303-318.
Evrard, M., et al., "Developmental Analysis of Bone Marrow Neutrophils Reveals Populations Specialized in Expansion, Trafficking, and Effector Functions", 2018, Immunity 48, 364-379.
Zhu, Y.P., et al., "Identification of an Early Unipotent Neutrophil Progenitor with Pro-Tumoral Activity in Mouse and Human Bone Marrow", Cell Rep. Aug. 28, 2018; 24(9): 2329-2341.

* cited by examiner

*Primary Examiner* — Shafiqul Haq
(74) *Attorney, Agent, or Firm* — Hamilton, Brook, Smith & Reynolds, P.C.

(57) ABSTRACT

There is provided a method of identifying a neutrophil progenitor, the method comprising: determining an expression of at least one biomarker selected from the group consisting of: CD71, LOX-1, CD164, CD112, CD181, TAC-STD2, CD11b and CD49d in a cell. In various embodiments, the cell is identified as a neutrophil progenitor when it is determined to have at least one of the following expression profiles: $CD71^{hi/+}$, $LOX-1^{int/lo/-}$, $CD164^{hi/+}$, $CD112^{hi/+}$, $CD181^{int/lo/-}$, $TACSTD2^{hi/+}$, $CD11b^{lo/-}$ and/or $CD49d^{int/hi/+}$. Also disclosed are a method of sorting and/or separating neutrophil progenitors from a cell population, a composition that is enriched in neutrophil progenitors and related uses and methods.

11 Claims, 36 Drawing Sheets

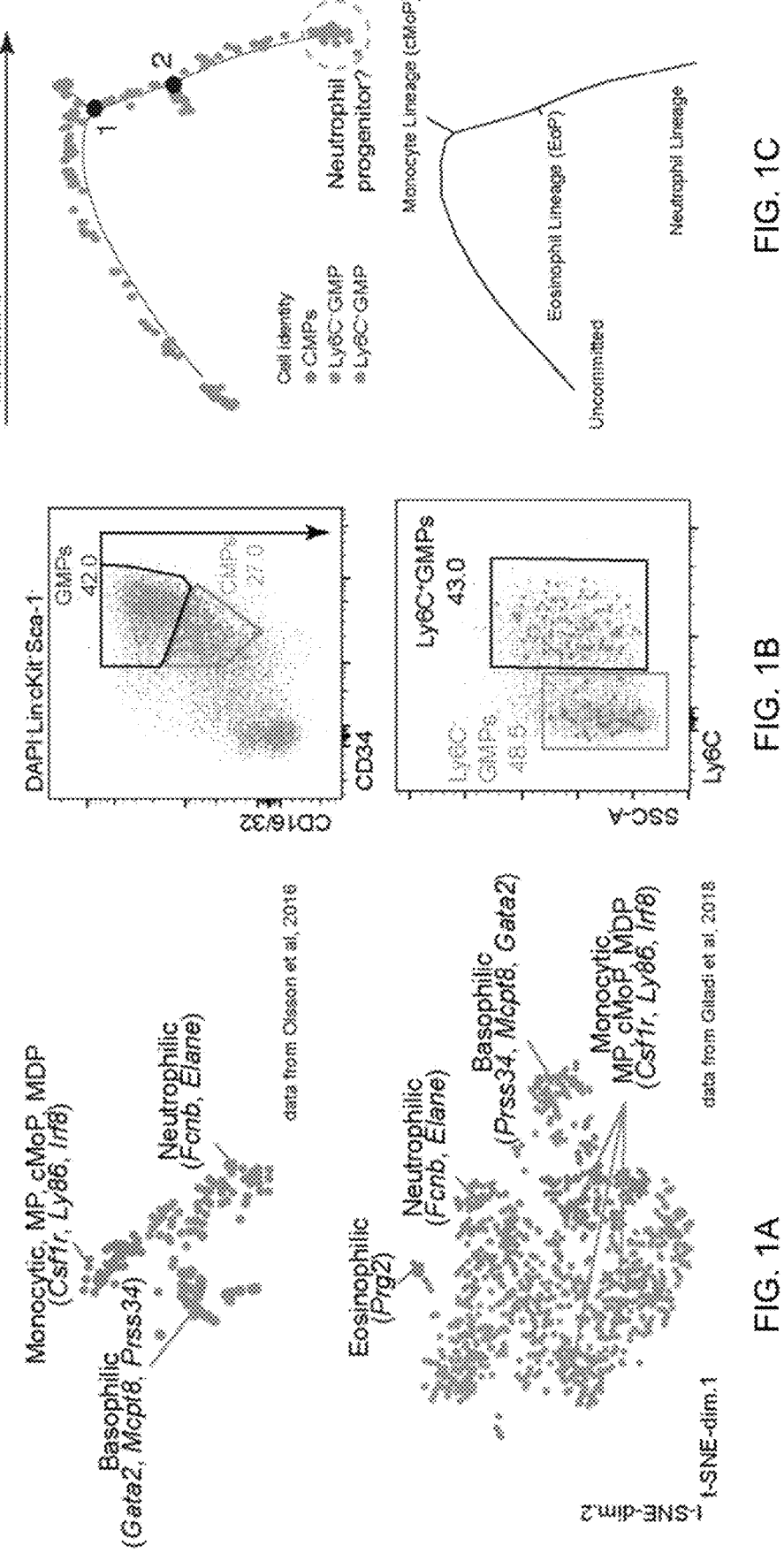

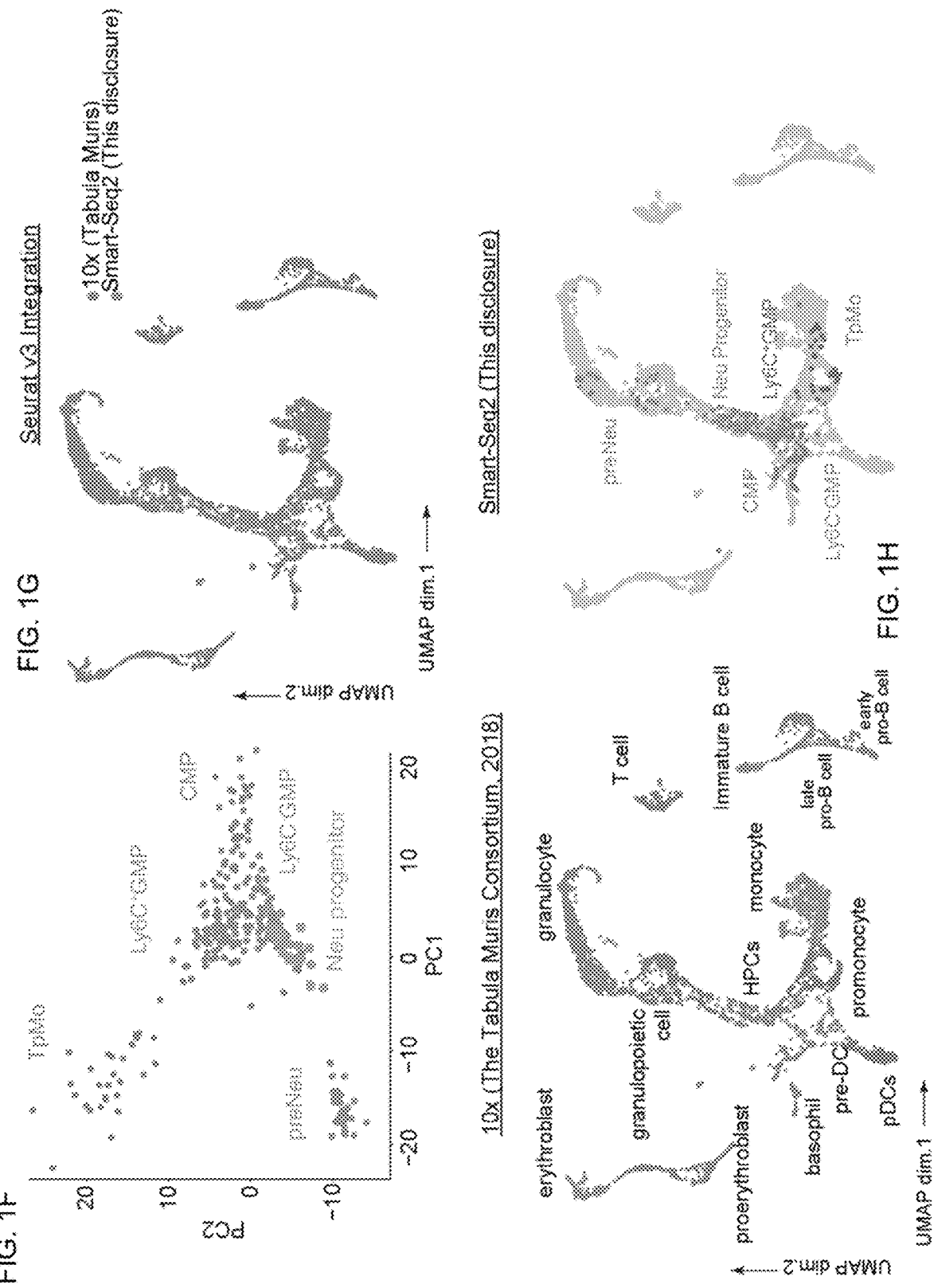

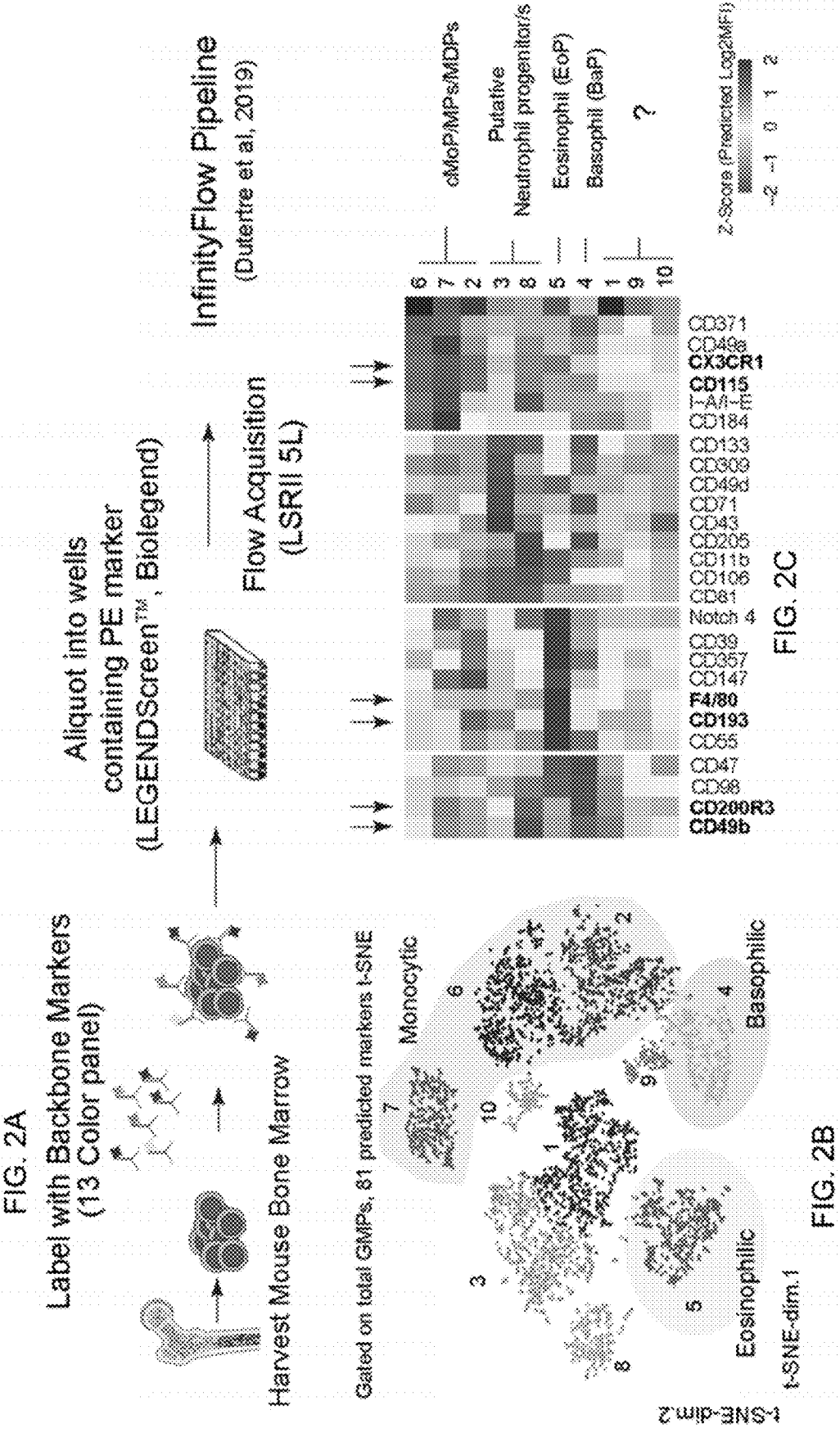

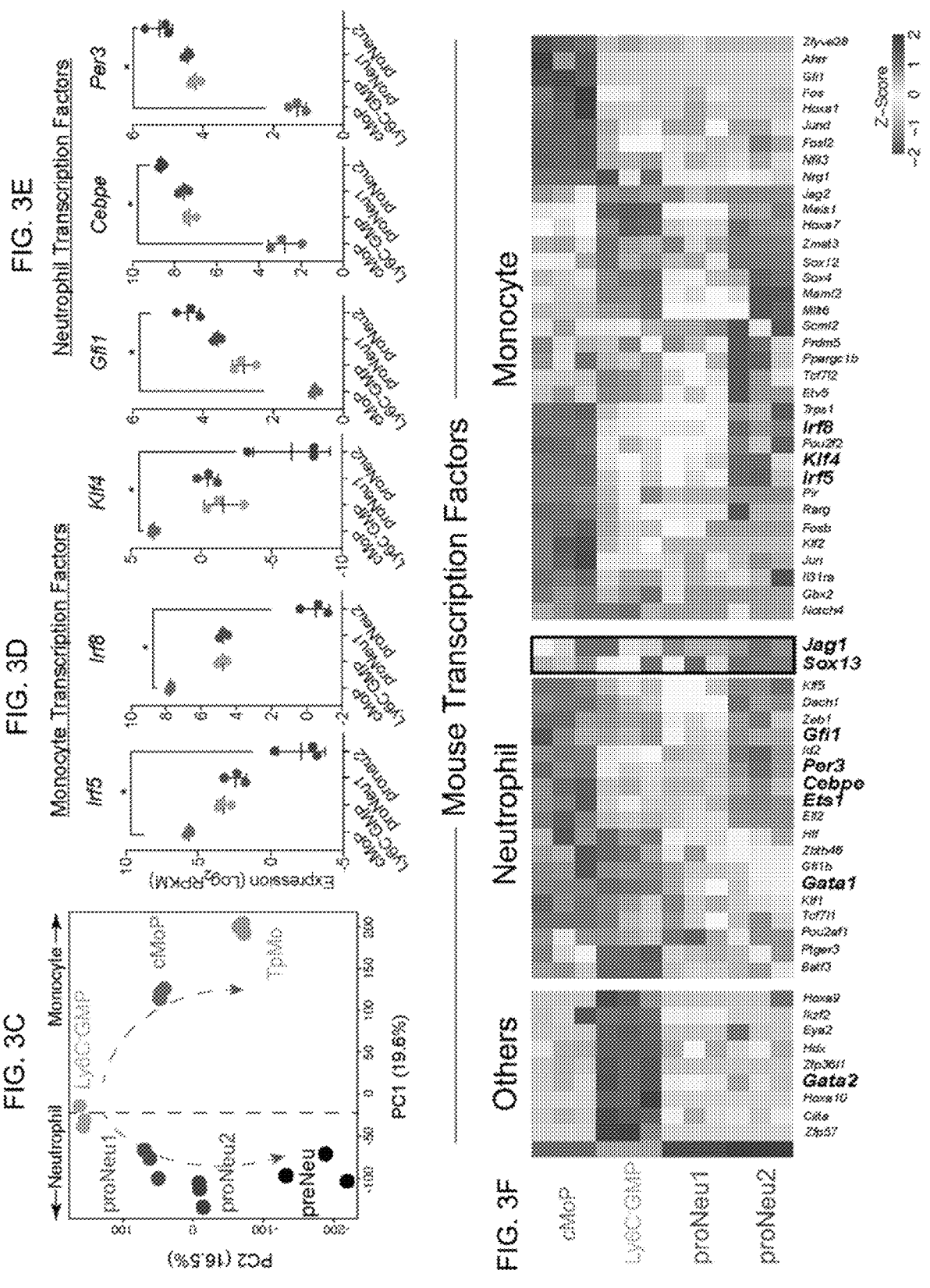

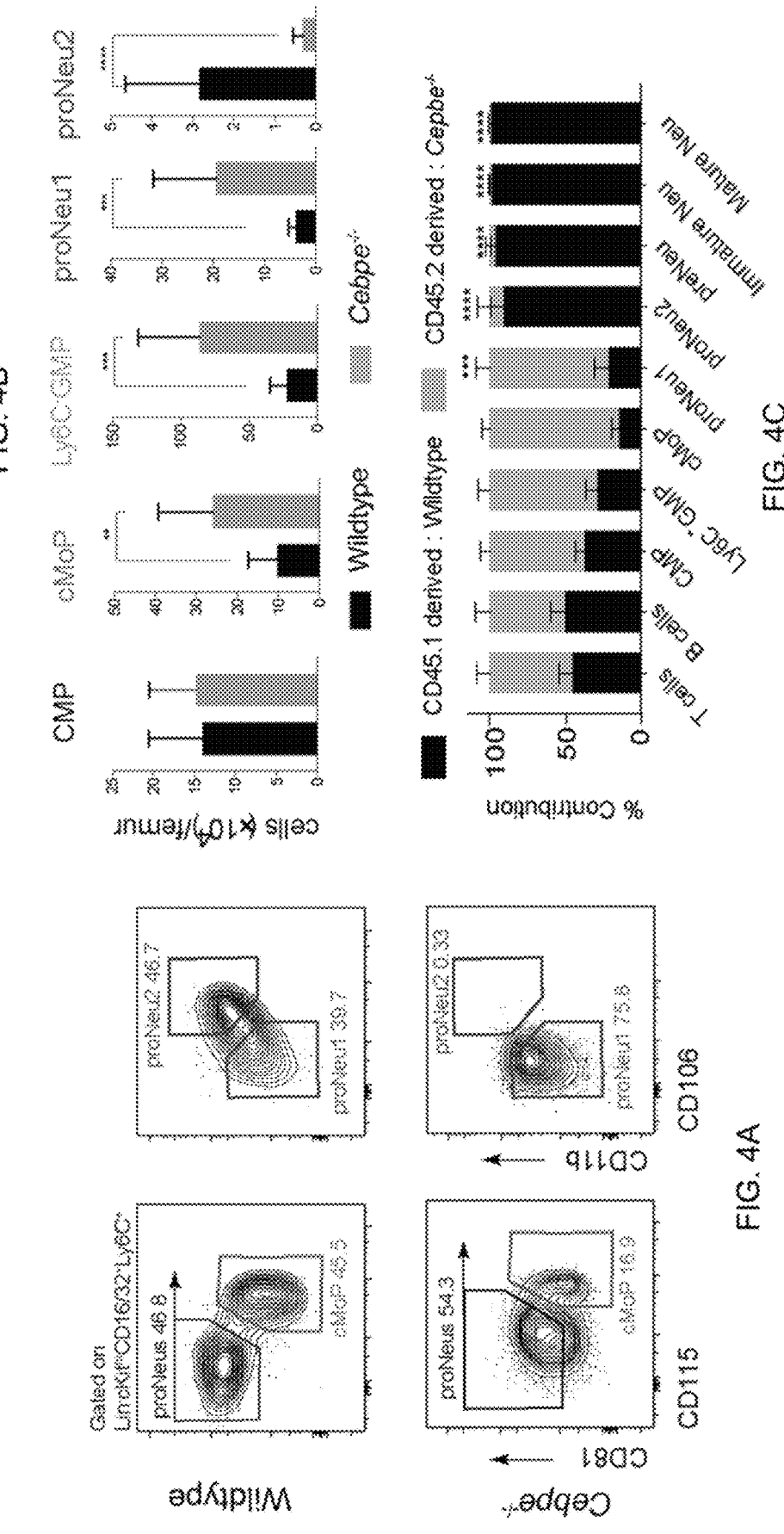

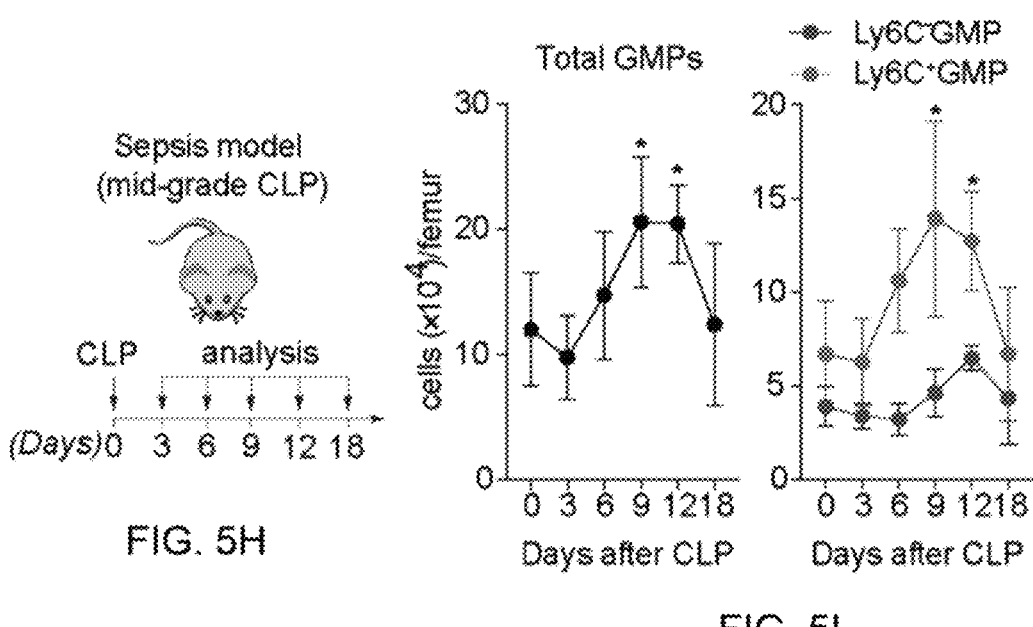
FIG. 5H
FIG. 5I
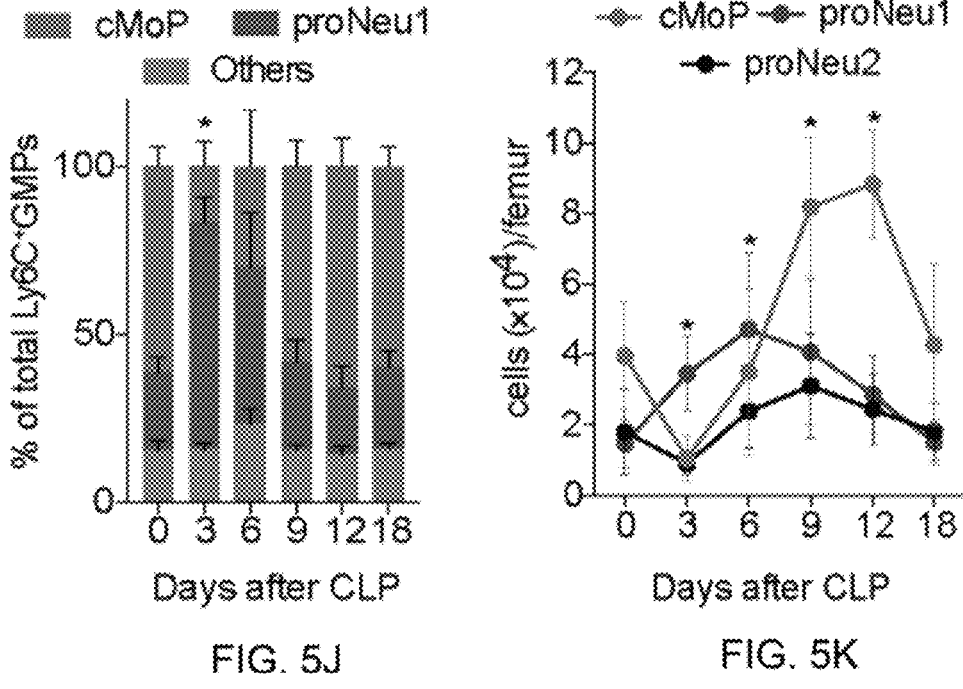
FIG. 5J
FIG. 5K

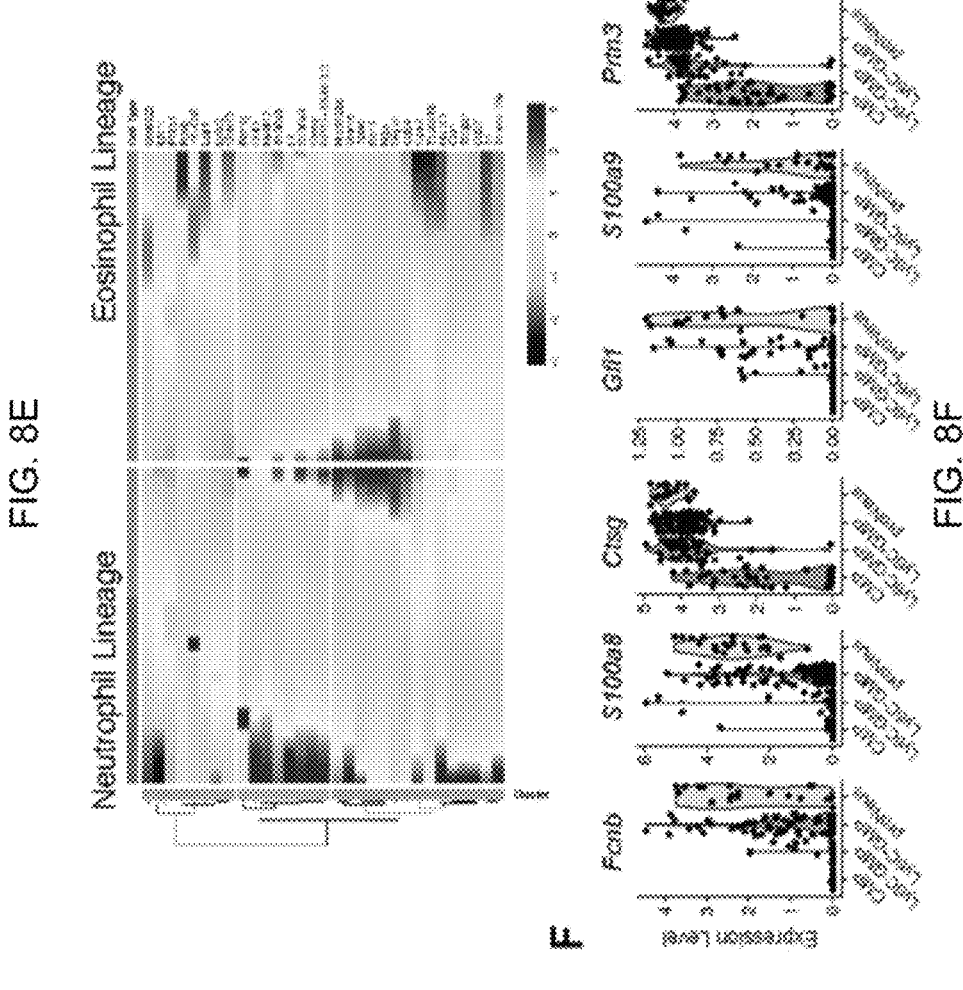
FIG. 8E
FIG. 8F
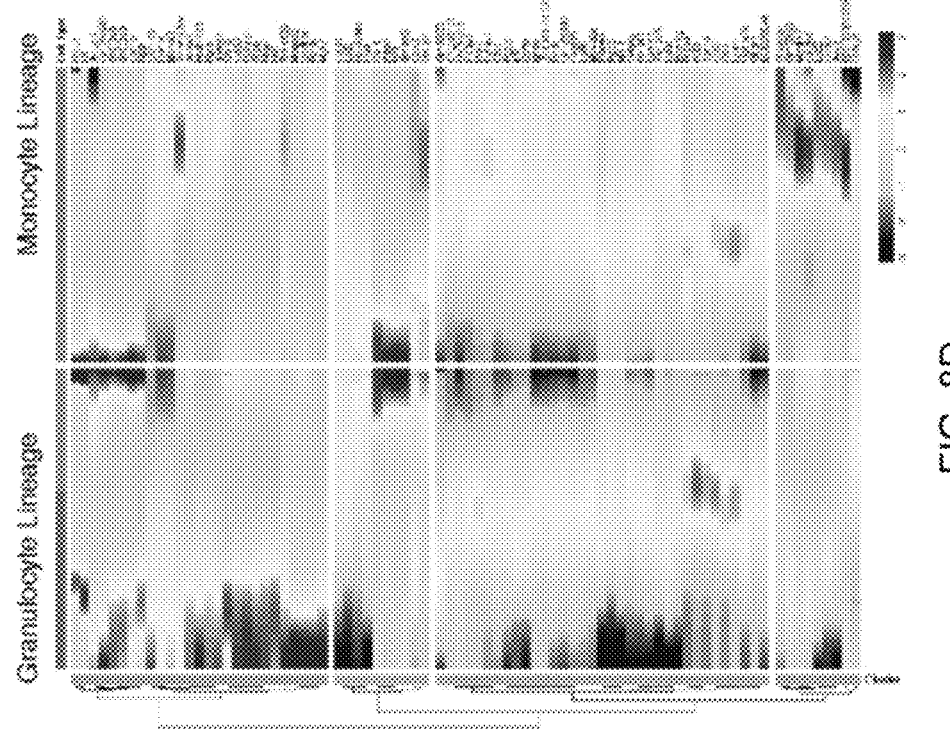
FIG. 8D

Phenograph

Total Mouse Bone Marrow

FIG. 9C

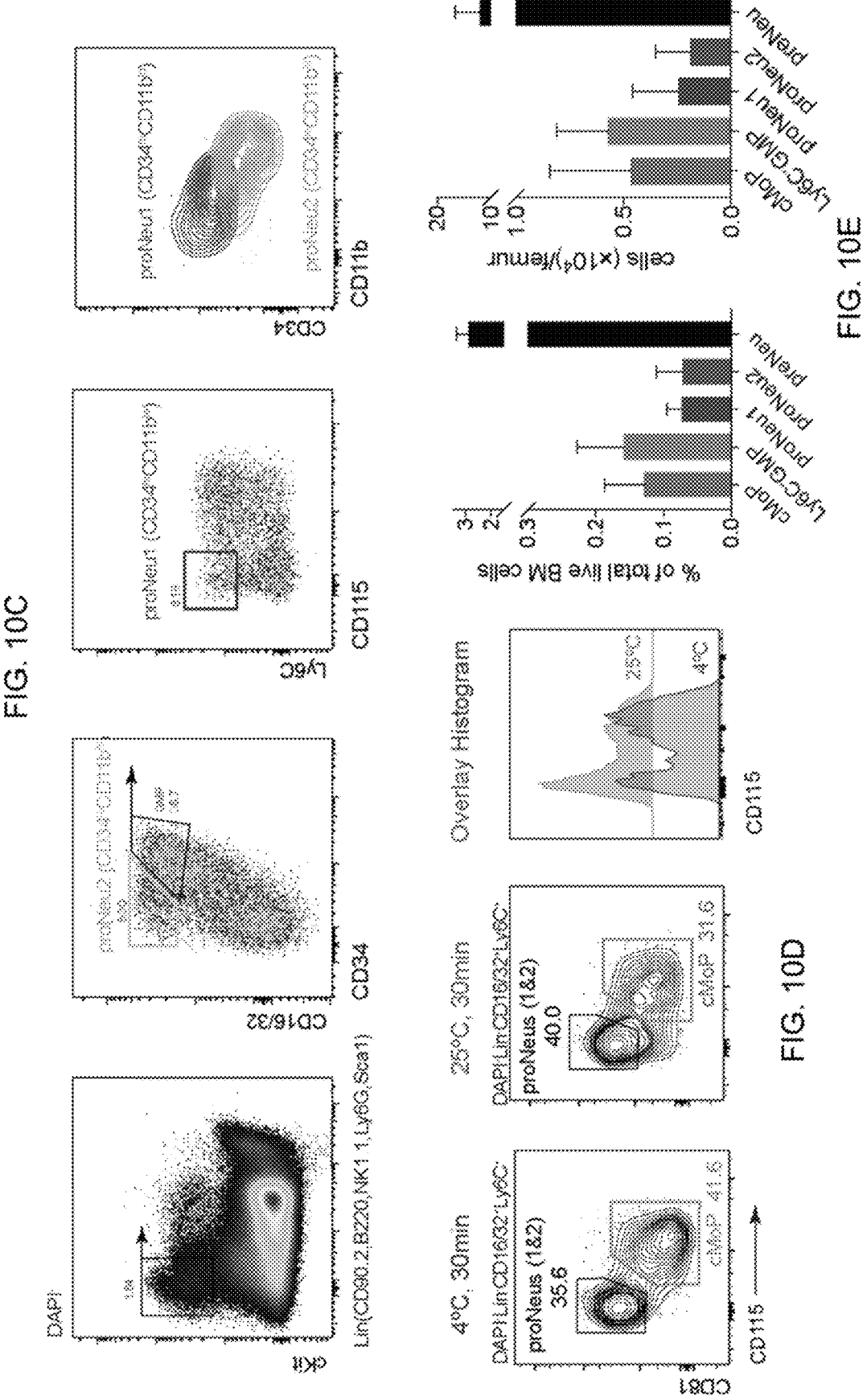

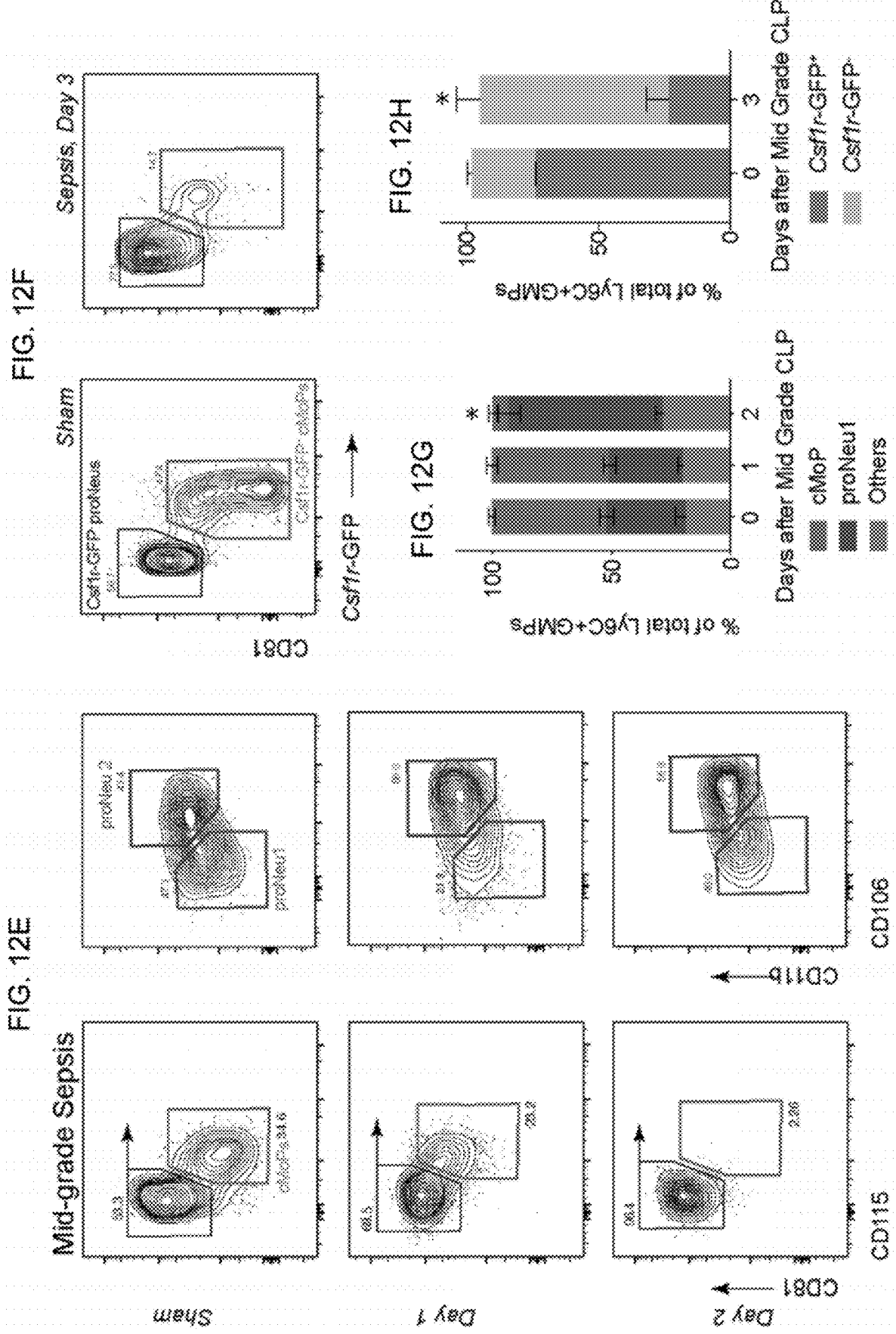

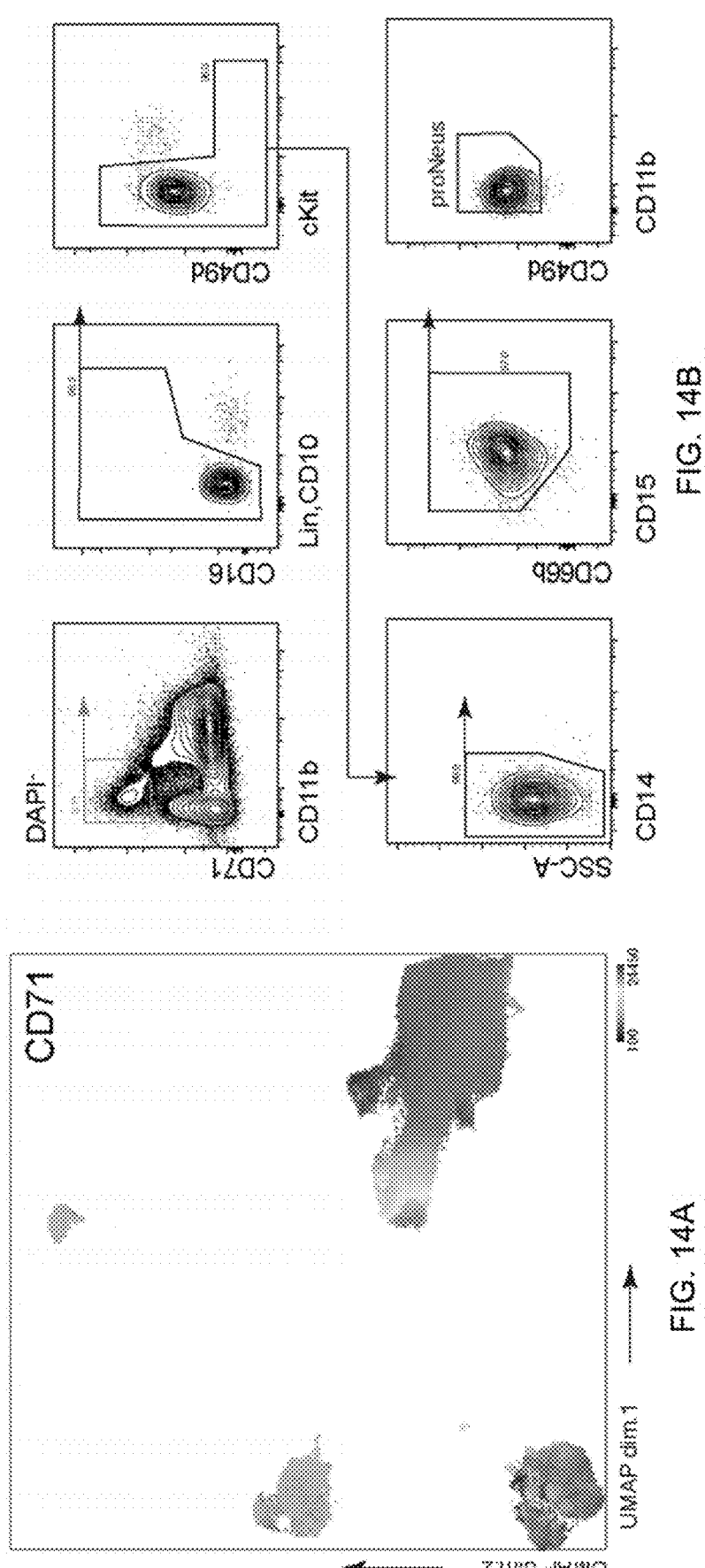

NEUTROPHIL PROGENITORS AND RELATED METHODS AND USES

This application is the U.S. National Stage of International Application No. PCT/SG2021/050342, filed Jun. 11, 2021, which designates the U.S., published in English, and claims priority under 35 U.S.C. § 119 or 365(c) to Singapore Application No. 10202005589P, filed Jun. 12, 2020. The entire teachings of the above applications are incorporated herein by reference.

TECHNICAL FIELD

The present disclosure relates broadly to a granulocyte-monocyte progenitor (GMP) subpopulation, such as neutrophil progenitors, and related methods and uses.

BACKGROUND

Hematopoietic Stem Cell Transplantation (HSCT) is a common treatment for hematological disorders and neoplastic diseases. However, the generation of neutrophils, which are important immune cells that provide protection against bacterial and fungal infections, from stem cells is a long process that takes an estimated 3-4 weeks in human. Thus, neutropenia after transplantation often leads to morbidity and mortality caused by infections. Current clinical management involves administration of prophylactic antimicrobial drugs, recombinant growth factors (e.g., G-CSF) or repeated Donor Granulocyte Infusion (DGI) in isolation wards to provide immune protection for patients during the neutropenic period, which can be ineffective and associated with high healthcare costs.

Thus, there is a need to address or at least ameliorate one or more of the above-mentioned problems. In particular, there is a need to provide a method of identifying a neutrophil progenitor, a method of sorting and/or separating neutrophil progenitors from a cell population, a composition that is enriched in neutrophil progenitors and related uses and methods that address or at least ameliorate one or more of the above-mentioned problems.

SUMMARY

In one aspect, there is provided a method of identifying a neutrophil progenitor, the method comprising: determining an expression of at least one biomarker selected from the group consisting of: CD71, LOX-1, CD164, CD112, CD181, TACSTD2, CD11b and CD49d in a cell; and identifying the cell as a neutrophil progenitor when it is determined to have at least one of the following expression profiles: CD71$^{hi/+}$, LOX-1$^{int/lo/-}$, CD164$^{hi/+}$, CD112$^{hi/+}$, CD181$^{int/lo/-}$, TACSTD2$^{hi/+}$, CD11b$^{lo/-}$ and/or CD49d$^{int/hi/+}$.

In one embodiment, the biomarker comprises CD71 and the cell is identified to be a neutrophil progenitor when it is determined to have CD71$^{hi/+}$ expression.

In one embodiment, where the cell is identified as a neutrophil progenitor, the method further comprises: determining an expression of a further biomarker selected from CD49d and/or a side-scatter (SSC) property of the neutrophil progenitor; and identifying a subtype of the neutrophil progenitor based on the expression of the further biomarker and/or the side-scatter property.

In one embodiment, where the neutrophil progenitor is determined to be CD49d$^{hi/+}$ and/or SSC$^{lo}$, the neutrophil progenitor is identified as an early committed neutrophil progenitor, and wherein where the neutrophil progenitor is determined to be CD49d$^{int/lo/-}$ and/or SSC$^{hi}$, the neutrophil progenitor is identified as an intermediate neutrophil progenitor that is downstream in neutrophil lineage to the early committed neutrophil progenitor.

In one embodiment, determination of the expression of the at least one biomarker and/or the further biomarker comprises contacting the cell with one or more antibodies against the biomarker and/or the further biomarker.

In one aspect, there is provided a method of sorting and/or separating neutrophil progenitors from a cell population, the method comprising: selecting for cells having at least one of the following expression profiles: CD71$^{hi/+}$, LOX-1$^{int/lo/-}$, CD164$^{hi/+}$, CD112$^{hi/+}$, CD181$^{int/lo/-}$, TACSTD2$^{hi/+}$, CD11b$^{lo/-}$ and/or CD49d$^{int/hi/+}$.

In one embodiment, the method comprises selecting for CD71$^{hi/+}$ cells.

In one embodiment, the cell population is derived from cord blood and/or bone marrow.

In one embodiment, the method further comprises culturing the neutrophil progenitors to obtain proliferation and/or differentiation of the neutrophil progenitors to obtain progenies thereof.

In one embodiment, the method further comprises administering the neutrophil progenitors and/or the progenies thereof to a subject in need thereof.

In one embodiment, the subject has neutropenia.

In one embodiment, the selecting step comprises contacting the cells with one or more antibodies against one or more of CD71, LOX-1, CD164, CD112, CD181, TACSTD2, CD11b and CD49d.

In one aspect, there is provided a composition that is enriched in neutrophil progenitors having at least one of the following expression profiles: CD71$^{hi/+}$, LOX-1$^{int/lo/-}$, CD164$^{hi/+}$, CD112$^{hi/+}$, CD181$^{int/lo/-}$, TACSTD2$^{hi/+}$, CD11b$^{lo/-}$ and/or CD49d$^{int/hi/+}$.

In one embodiment, the composition is enriched in CD71$^{hi/+}$ neutrophil progenitors.

In one aspect, there is provided the composition for use in therapy.

In one aspect, there is provided the composition for use in treating neutropenia.

In one aspect, there is provided use of the composition in the manufacture of a medicament for treating neutropenia.

In one aspect, there is provided a method of preparing a transfusion composition, the method comprising: enriching a composition for neutrophil progenitors having at least one of the following expression profiles: CD71$^{hi/+}$, LOX-1$^{int/lo/-}$, CD164$^{hi/+}$, CD112$^{hi/+}$, CD181$^{int/lo/-}$, TACSTD2$^{hi/+}$, CD11$^{lo/-}$ and/or CD49d$^{int/hi/+}$.

In one embodiment, the method comprises enriching the composition for CD71$^{hi/+}$ neutrophil progenitors.

In one embodiment, the enriching step comprises contacting the composition with one or more antibodies against one or more of CD71, LOX-1, CD164, CD112, CD181, TACSTD2, CD11b and CD49d.

Definitions

The term "treatment", "treat" and "therapy", and synonyms thereof as used herein refer to both therapeutic treatment and prophylactic or preventative measures, wherein the object is to prevent or slow down (lessen) a medical condition, which includes but is not limited to diseases, symptoms and disorders. A medical condition also includes a body's response to a disease or disorder, e.g., inflammation. Those in need of such treatment include those already with a medical condition as well as those prone to getting the medical condition or those in whom a medical condition is to be prevented.

As used herein, the term "therapeutically effective amount" of a compound will be an amount of an active agent that is capable of preventing or at least slowing down (lessening) a medical condition, such as neutropenia. Dosages and administration of compounds, compositions and formulations of the present disclosure may be determined by one of ordinary skill in the art of clinical pharmacology or pharmacokinetics. See, for example, Mordenti and Rescigno, (1992) Pharmaceutical Research. 9:17-25; Morenti et al., (1991) Pharmaceutical Research. 8:1351-1359; and Mordenti and Chappell, "The use of interspecies scaling in toxicokinetics" in Toxicokinetics and New Drug Development, Yacobi et al. (eds) (Pergamon Press: NY, 1989), pp. 42-96. An effective amount of the active agent of the present disclosure to be employed therapeutically will depend, for example, upon the therapeutic objectives, the route of administration, and the condition of the patient. Accordingly, it may be necessary for the therapist to titer the dosage and modify the route of administration as required to obtain the optimal therapeutic effect.

The term "subject" as used herein includes patients and non-patients. The term "patient" refers to individuals suffering or are likely to suffer from a medical condition such as cancer, while "non-patients" refer to individuals not suffering and are likely to not suffer from the medical condition. "Non-patients" include healthy individuals, non-diseased individuals and/or an individual free from the medical condition. The term "subject" includes humans and animals. Animals include murine and the like. "Murine" refers to any mammal from the family Muridae, such as mouse, rat, and the like.

As used herein, an "expression" refers to both genotypic as well as phenotypic expression of biomarkers in the present disclosure.

A "biomarker" refers to a molecule, for example, a protein, carbohydrate structure, glycolipid, glycoprotein (including cell surface glycoprotein), receptor (including cell surface receptor) or gene (or nucleic acid encoding the gene), the expression of which in or on a cell (or sample) derived from a subject (such as a mammalian tissue) can be detected by standard methods in the art (as well as those disclosed herein). In some examples, a biomarker may be any molecule that may serve as an identifier (i.e., marker) of a target of interest. In some examples, a biomarker may be a cell surface receptor, a cell surface glycoprotein, a transcription factor, and the like. In some examples, the biomarker may be used to classify, identify, detect, isolate, purify, enrich, select, sort, and/or separate a cell/cell population, and/or determine a stage of differentiation, a stage of development and/or activity state of a cell.

In some examples, where the biomarker comprises a cell surface marker, the expression of the marker may be denoted in accordance to the acceptable denotation known in common general knowledge. For example, for a cell surface marker CD71, a $CD71^+$ refers to the cell positively expressing CD71, a $CD71^-$ refers to the cell not expressing detectable CD71, $CD71^{lo}$ refers to the cell expressing low CD71, $CD71^{int}$ refers to the cell expressing intermediate CD71, and $CD71^{hi}$ refers to the cell expressing high CD71.

As used in the specification herein, agents for detecting biomarkers in the present disclosure refer to any compound, molecule and/or system that functions to detect the presence/absence and/or expression or level thereof of biomarkers in the present disclosure. Such agents are capable of detecting and/or binding directly or indirectly to a biomarker. In the present disclosure, additional moieties may be required to enhance the detection of the biomarkers, for example, by/through amplifying optical diffraction. Examples of agents and the additional moieties include but are not limited to proteins (for example antigen binding proteins such as antibodies or fragments thereof, enzymes such as horseradish peroxides and alkaline phosphatase, and the like), polynucleotides (for example aptamers), and small molecules (for example metallic nanoparticles).

The term "micro" as used herein is to be interpreted broadly to include dimensions from about 1 micron to about 1000 microns.

The term "nano" as used herein is to be interpreted broadly to include dimensions less than about 1000 nm.

The term "particle" as used herein broadly refers to a discrete entity or a discrete body. The particle described herein can include an organic, an inorganic or a biological particle. The particle used described herein may also be a macro-particle that is formed by an aggregate of a plurality of sub-particles or a fragment of a small object.

The particle of the present disclosure may be spherical, substantially spherical, or non-spherical, such as irregularly shaped particles or ellipsoidally shaped particles. The term "size" when used to refer to the particle broadly refers to the largest dimension of the particle. For example, when the particle is substantially spherical, the term "size" can refer to the diameter of the particle; or when the particle is substantially non-spherical, the term "size" can refer to the largest length of the particle.

The terms "coupled" or "connected" as used in this description are intended to cover both directly connected or connected through one or more intermediate means, unless otherwise stated.

The term "associated with", used herein when referring to two elements refers to a broad relationship between the two elements. The relationship includes, but is not limited to a physical, a chemical or a biological relationship. For example, when element A is associated with element B, elements A and B may be directly or indirectly attached to each other or element A may contain element B or vice versa.

The term "adjacent" used herein when referring to two elements refers to one element being in close proximity to another element and may be but is not limited to the elements contacting each other or may further include the elements being separated by one or more further elements disposed therebetween.

The term "and/or", e.g., "X and/or Y" is understood to mean either "X and Y" or "X or Y" and should be taken to provide explicit support for both meanings or for either meaning.

Further, in the description herein, the word "substantially" whenever used is understood to include, but not restricted to, "entirely" or "completely" and the like. In addition, terms such as "comprising", "comprise", and the like whenever used, are intended to be non-restricting descriptive language in that they broadly include elements/components recited after such terms, in addition to other components not explicitly recited. For example, when "comprising" is used, reference to a "one" feature is also intended to be a reference to "at least one" of that feature. Terms such as "consisting", "consist", and the like, may in the appropriate context, be considered as a subset of terms such as "comprising", "comprise", and the like. Therefore, in embodiments disclosed herein using the terms such as "comprising", "comprise", and the like, it will be appreciated that these embodiments provide teaching for corresponding embodiments using terms such as "consisting", "consist", and the like. Further, terms such as "about", "approximately" and the like whenever used, typically means a reasonable variation, for example a variation of +/−5% of the disclosed value, or a variance of 4% of the disclosed value, or a variance of 3% of the disclosed value, a variance of 2% of the disclosed value or a variance of 1% of the disclosed value.

Furthermore, in the description herein, certain values may be disclosed in a range. The values showing the end points of a range are intended to illustrate a preferred range. Whenever a range has been described, it is intended that the range covers and teaches all possible sub-ranges as well as individual numerical values within that range. That is, the end points of a range should not be interpreted as inflexible limitations. For example, a description of a range of 1% to 5% is intended to have specifically disclosed sub-ranges 1% to 2%, 1% to 3%, 1% to 4%, 2% to 3% etc., as well as individually, values within that range such as 1%, 2%, 3%, 4% and 5%. It is to be appreciated that the individual numerical values within the range also include integers, fractions and decimals. Furthermore, whenever a range has been described, it is also intended that the range covers and teaches values of up to 2 additional decimal places or significant figures (where appropriate) from the shown numerical end points. For example, a description of a range of 1% to 5% is intended to have specifically disclosed the ranges 1.00% to 5.00% and also 1.0% to 5.0% and all their intermediate values (such as 1.01%, 1.02% . . . 4.98%, 4.99%, 5.00% and 1.1%, 1.2% . . . 4.8%, 4.9%, 5.0% etc.,) spanning the ranges. The intention of the above specific disclosure is applicable to any depth/breadth of a range.

Additionally, when describing some embodiments, the disclosure may have disclosed a method and/or process as a particular sequence of steps. However, unless otherwise required, it will be appreciated that the method or process should not be limited to the particular sequence of steps disclosed. Other sequences of steps may be possible. The particular order of the steps disclosed herein should not be construed as undue limitations. Unless otherwise required, a method and/or process disclosed herein should not be limited to the steps being carried out in the order written. The sequence of steps may be varied and still remain within the scope of the disclosure.

Furthermore, it will be appreciated that while the present disclosure provides embodiments having one or more of the features/characteristics discussed herein, one or more of these features/characteristics may also be disclaimed in other alternative embodiments and the present disclosure provides support for such disclaimers and these associated alternative embodiments.

DESCRIPTION OF EMBODIMENTS

Exemplary, non-limiting embodiments of a method of characterising/identifying a granulocyte-monocyte progenitor (GMP) population, such as a neutrophil progenitor subpopulation, and related compositions, methods and kits are disclosed hereinafter.

GMPs are known to give rise to granulocytes (such as neutrophils, eosinophils, and basophils) and monocytes. In some examples, GMPs are found to contain a mixed population of monocytic, neutrophilic, eosinophilic and basophilic progenitor subsets. In various embodiments, there is provided a method of classifying, identifying, detecting, isolating, purifying, enriching, selecting, sorting and/or separating a GMP cell/population/subpopulation/subset and/ or determining a stage of differentiation, a stage of development and/or activity state of a cell/population/subpopulation/subset. GMP subpopulations (or subsets) may include a monocytic progenitor subpopulation, a neutrophilic progenitor subpopulation, an eosinophilic progenitor subpopulation and a basophilic progenitor subpopulation. Further distinct subpopulations (or subsets) may exist within these progenitor subpopulations.

In various embodiments, the method comprises determining a transcriptomic profile and/or proteomic profile of the cell/population/subpopulation/subset. In various embodiments, the method comprises determining and/or measuring the presence/absence/amount/level/proportion of one or more markers/biomarkers/signatures in the cell/population/subpopulation/subset. In various embodiments, the method comprises determining and/or measuring one or more physical properties of the cell/population/subpopulation/subset. The determination or measurement may be quantitative, semi-quantitative or qualitative.

In various embodiments, the method comprises determining or measuring the presence/absence/amount/level/proportion of at least about one, at least about two, at least about three, at least about four, at least about five, at least about six, at least about seven, at least about eight, at least about nine or at least about ten markers/biomarkers and/or physical properties associated with the cell/population/subpopulation/subset. In various embodiments, the method comprises determining or measuring the presence/absence/amount/level/proportion of no more than about ten, no more than about nine, no more than about eight, no more than about seven, no more than about six, no more than about five, no more than about four, no more than about three, no more than two or not more than about one marker/biomarker and/or physical property associated with the cell/population/subpopulation/subset.

Markers/biomarkers/signature or a component thereof include, but are not limited to, polypeptides (e.g., cell surface proteins) and polynucleotides (e.g., DNA and RNA). The markers/biomarkers/signature may be transcriptomic and/or proteomic markers/biomarkers/signatures. In some embodiments, the marker comprises an RNA marker/biomarker/signature. In some embodiments, the marker comprises a protein marker/biomarker/signature. In some embodiments, the marker comprises a surface/cell surface marker/biomarker/signature. In some embodiments, the marker comprises a transcription factor.

In various embodiments, the marker/biomarker/signature is selected from the group consisting of: 33D1, 4-11BB Ligand, APCDD1, B220, B7H4, B7-H4, C3aR, Cadherin 11, CCR10, CCRL2, CCX-CKR (CCRL1), CD10, CD100, CD102, CD103, CD104, CD105 (Endoglin), CD106, CD107a, CD107b, CD109, CD111, CD112, CD114, CD115, CD116, CD117, CD119, CD11a, CD11b, CD11c, CD120a, CD120b, CD121a, CD122, CD123, CD124, CD126, CD127, CD129, CD13, CD130, CD131, CD132, CD133, CD134, CD135, CD137, CD138, CD14, CD140a, CD140b, CD141, CD142, CD143, CD144, CD146, CD147, CD148, CD15, CD150, CD151, CD152, CD152 (CTLA-4), CD153, CD154, CD155, CD156c, CD157, CD158, CD158b, CD158e1, CD159a, CD16, CD16.2, CD160, CD161, CD162, CD163, CD164, CD165, CD166, CD169, CD170, CD172a (SIRPα), CD172b (SIRPβ), CD172g (SIRPγ), CD178, CD179a, CD179b, CD18, CD180, CD181, CD182, CD183, CD184, CD185, CD186 (CXCR6), CD19, CD191, CD192, CD193, CD194, CD195, CD196, CD197, CD198, CD199, CD1a, CD1b, CD1c, CD1d, CD2, CD20, CD200, CD200R, CD200R3, CD201, CD202b, CD203c, CD205, CD206, CD207, CD209, CD21, CD210, CD213α1, CD213α2, CD215, CD217, CD218a, CD22, CD220, CD220R, CD221, CD223 (LAG-3), CD226, CD227, CD229, CD23, CD230 (Prion), CD235ab, CD24, CD243, CD244 (2B4) CD245, CD25, CD252, CD253, CD254, CD255, CD258, CD26, CD261, CD262, CD263, CD265, CD266, CD267, CD268, CD269, CD27, CD272, CD273, CD274, CD275, CD276, CD277, CD278, CD279, CD28, CD282, CD284, CD29, CD290, CD294, CD298, CD3, CD30, CD300c, CD300d, CD300LG, CD301, CD301b, CD303, CD304, CD307e, CD309, CD31, CD314, CD317, CD318, CD319, CD32, CD323, CD324, CD325, CD326, CD328, CD33, CD334, CD335, CD336, CD337, CD338, CD339, CD34, CD34_MEC14.7, CD34_SA376A4, CD340, CD344, CD35, CD351, CD352, CD354, CD355, CD357, CD36, CD360, CD365, CD366, CD368, CD369, CD36L1, CD37, CD370, CD371, CD38, CD39, CD3e, CD4, CD40, CD41, CD42b, CD43, CD44, CD45, CD45.1, CD45.2, CD45RA, CD45RB, CD45RO, CD46, CD47, CD48, CD49a, CD49b, CD49c, CD49d, CD49e, CD49f, CD5, CD50, CD51, CD52, CD54, CD55, CD56 (NCAM), CD57, CD58, CD59, CD59a, CD6, CD61, CD62L, CD62P, CD63, CD64, CD66a, CD66b, CD66c, CD66e, CD69, CD7, CD70, CD71, CD73, CD74, CD79b, CD80, CD81, CD82, CD83, CD84, CD85, CD85d, CD85h, CD85k, CD86, CD87, CD88, CD89, CD8a, CD8b, CD9, CD90, CD90.1, CD90.2, CD92, CD93, CD94, CD95, CD96, CD97, CD98, CD99, cKit, CLEC4A, CX3CR1, CXCL16, CXCR7, DcTRAIL R1, Delta Opioid Receptor, Delta-like 1 (DLL1), Delta-like 4 (DLL4), Dopamine Receptor D1 (DRD1), DR3, E-Cadherin, EGFR, EphA2, erbB3, ESAM, F4/80, FcεRIα, FLT3, FPR3, FR4, Galectin9, Ganglioside GD2, GARP, GITR Ligand, GL7, GPR19, GPR56, GPR83, Gr1, H2, HLA-A, HLA-B, HLA-C, HLA-DR, HLA-E, HVEM, IA/IE, IFNAR1, IFNgR b chain, IFN-γ R b chain, Ig light chain κ, Ig light chain λ, IgD, IgG Fc, IgM, IL21R, IL23R, IL-28RA, IL33R, IL33Ra, Integrin α9β1, integrin β5, Integrin β7, Isotype AHIgG, Isotype mIgG1, Isotype mIgG2a, Isotype mIgG2b, Isotype mIgM, Isotype rIgG1, Isotype rIgG2a, Isotype rIgG2b, Isotype rIgG2c, Isotype rIgM, Isotype SHIgG, Jagged 2, JAML, KLRG1, Ksp37, LAP, LOX-1, LPAM_1, Ly-49A, Ly108, Ly49CFIH, Ly49D, Ly49H, Ly51, Ly6C, Ly6D, Ly6G, LY6G6D, Ly6K, Lymphotoxin β Receptor, Mac2, Mac3, MAdCAM1, MAIR-IV, MAIRV, MD1, MERTK, MICA, MICB, MRGX2, MSC, MUC-13, NK1.1, NKG2D, NKp80, Notch 1, Notch 2, Notch 3, Notch 4, Notch3, NPC, PD1H, PDC-TREM, PIR A, PIR B, Plexin B2, Podoplanin, PSMA, RAE1y, Sca-1, Sialyl Lewis X (dimeric), Siglec H, Siglec-10, Siglec-8, Siglec-9, SiglecF, SiglecH, SSC, SSEA-1, SSEA-3, SSEA-4, SSEA-5, SUSD2, TACSTD2, TCR gd, TCR Vd1.1_1.2, TCR α, TCR β, TCRb chain, TER119, TIGIT (VSTM3), Tim-2, Tim-4, TLR4, TLT-2, TM4SF20, TMEM8A, TNAP, TRA-1-60-R, TRA-1-81, TRA-2-49, TRA-2-54, Trem-like 4, TSLPR, VEGFR-3, VISTA and XCR1. In various embodiments, the markers/biomarkers/signature comprises one discussed in the Examples section of the present disclosure.

In some examples, a population of early neutrophil progenitors is found to exist within GMPs, the population extending along the developmental trajectory towards mature neutrophils. In various embodiments therefore, there is provided a method of classifying, identifying, detecting, isolating, purifying, enriching, selecting, sorting and/or separating a neutrophil progenitor/neutrophil progenitor population and/or determining a stage of differentiation, a stage of development and/or activity state of a neutrophil progenitor/neutrophil progenitor population. In various embodiments, the neutrophil progenitor comprises a committed neutrophil progenitor. For example, the neutrophil progenitor may be incapable of differentiating into a cell of a non-neutrophil lineage, such as a monocyte, under physiological conditions. In some examples, neutrophil progenitors give rise to Ly6G⁺ neutrophils but not macrophages when cultured with a factor (e.g., CSF-1) that promotes differentiation towards the monocytic lineage. Thus, while a neutrophil progenitor may differentiate (exclusively) along the neutrophil lineage (for example, to give rise to a preneutrophil (preNeu), an immature neutrophil or a mature neutrophil), a neutrophil progenitor may not differentiate into a cell of a non-neutrophil lineage. In various embodiments, the neutrophil progenitor is capable of generating mature neutrophils, for example, CD16⁺CD10⁺ mature neutrophils. In various embodiments, the neutrophil progenitor comprises an early neutrophil progenitor (e.g., a neutrophil progenitor that is upstream of preNeu and other neutrophil precursors in neutrophil lineage). In various embodiments, the neutrophil progenitor has a high proliferative capacity (e.g., higher proliferative capacity than preNeu and other neutrophil precursors).

The neutrophil progenitor may be that of an animal or a human. In some embodiments, the neutrophil progenitor comprises the neutrophil progenitor of a mammal (e.g., humans, non-human primates, canine, murine (e.g., mouse, rat, rabbit etc.) and the like). In some embodiments, the neutrophil progenitor comprises a mouse neutrophil progenitor. In some embodiments, the neutrophil progenitor comprises a human neutrophil progenitor.

In various embodiments, there is provided a method of identifying a neutrophil progenitor, the method comprising: determining an expression of at least about one, at least about two, at least about three, at least about four, at least about five or at least about six, at least about seven, at least about eight, at least about nine, at least about ten, at least about 11, at least about 12, at least about 13, at least about 14 or at least about 15 biomarker(s) selected from the group consisting of: CD71, LOX-1, CD164, CD112, CD181, TAC-STD2, Ly6C, CD115, CD11b, CD34, CD81, CD49a, CD49d, CD106 and CD63 in a cell. In various embodiments, there is provided a method of identifying a neutrophil progenitor, the method comprising: determining an expression of at least about one, at least about two, at least about three, at least about four, at least about five, at least about six, at least about seven or at least about eight biomarker(s) selected from the group consisting of: CD71 (transferrin receptor protein 1), LOX-1 (lectin-type oxidized low-density lipoprotein (LDL) receptor-1), CD164 (sialomucin core protein 24 or endolyn or cluster of differentiation 164), CD112 (poliovirus receptor-related 2 (PVRL2) or nectin-2), CD181 (Interleukin 8 receptor alpha or cluster of differentiation 181), TACSTD2 (Tumor Associated Calcium Signal Transducer 2), CD11b (Integrin alpha M or cluster of differentiation molecule 11 b) and CD49d (Integrin α4) in a cell. The cell may be a GMP cell (e.g., a cell having one or more of the following expression profiles: Lin⁻, cKit⁺, Sca-1⁻, CD34$^{hi/+}$, and CD16/32$^{hi}$) a bone marrow cell (e.g., a fetal bone marrow cell) or a cord blood cell. The cell may be an animal cell or a human cell. In various embodiments, where the cell is determined to be CD71$^{hi/+}$, LOX-1$^{int/lo/-}$, CD164$^{hi/+}$, CD112$^{hi/+}$, CD181$^{int/lo/-}$, TACSTD2$^{hi/+}$, CD11b$^{lo/-}$ and/or CD49d$^{int/hi/+}$, the cell is identified to be a neutrophil progenitor. In various embodiments therefore, the method comprises: determining an expression of at least one biomarker selected from the group consisting of: CD71, LOX-1, CD164, CD112, CD181, TACSTD2, CD11b and CD49d in a cell; and identifying the cell as a neutrophil progenitor when it is determined to have at least about one, at least about two, at least about three, at least about four, at least about five, at least about six, at least about seven or at least about eight of the following expression profiles: $CD71^{hi/+}$, $LOX\text{-}1^{int/lo/-}$, $CD164^{hi/+}$, $CD112^{hi/+}$, $CD181^{int/lo/-}$, $TACSTD2^{hi/+}$, $CD11^{lo/-}$ and/or $CD49d^{int/hi/+}$. Advantageously, the biomarkers disclosed herein are found to be capable to distinguishing a neutrophil progenitor from cells of other types or from a heterogenous cell population (e.g., a GMP population). In other words, a neutrophil progenitor may be characterized or identified by the expression of one or more of these biomarkers.

In one embodiment, the biomarker comprises CD71. In one embodiment therefore, the cell is identified to be a neutrophil progenitor when it is determined to express CD71 or when it is determined to be $CD71^{hi/+}$. In various embodiments therefore, there is provided a method of identifying a neutrophil progenitor, the method comprising: determining an expression of CD71 in a cell; and identifying the cell as a neutrophil progenitor when it is determined express CD71. In some examples, CD71 is found to be exclusively expressed by neutrophil progenitors among total cord blood cells.

In some embodiments, the method may comprise determining an expression of a transcription factor in the cell. In some embodiments, the method may comprise determining an expression of at least about one, at least about two, at least about three, at least about four, at least about five, at least about six, or at least about seven transcription factor(s) selected from the group consisting of: Jag1, Sox13, Gfi1, Per3, Cebpe, Ets1 and Gata1 in the cell.

Among neutrophil progenitors (termed as proNeus), the inventors found two phenotypically distinct neutrophil progenitors (termed as proNeu1 and proNeu2). In various examples, proNeu1 was found to possess higher self-renewing potential/properties and/or enhanced colony forming potential than proNeu2. In various examples, transcriptomic pathway analysis supported the decrease in progenitor function of proNeu2, showing an exclusive enrichment in neutrophil effector functions, while proNeu1 was enriched in cellular components and cell survival. In various examples, proNeu1 increased in numbers while proNeu2 remained largely unchanged during the course of an infection in a sepsis/inflammation model. In various examples, proNeu2 is shown to be a bridging point between proNeu1 and preNeu. In various examples, proNeu1 is shown to give rise to proNeu2 and subsequent neutrophil subsets and proNeu2 is shown to specifically give rise to preNeus and immature Neus. In various examples, proNeu1 is shown to exclusively give rise to downstream neutrophil subsets through a C/EBPε-dependent proNeu2 development. In various examples, proNeu1 is shown to be an early committed neutrophil and proNeu2 is shown to be an intermediate neutrophil progenitor that is downstream in neutrophil lineage to proNeu1.

In various embodiments therefore, where the cell is identified as a neutrophil progenitor, the method further comprises determining a subtype of the neutrophil progenitor. Determining a subtype of the neutrophil progenitor may comprise determining/measuring an expression of further biomarker(s) in the cell and/or one or more physical property associated with the cell.

In various embodiments, determining/measuring an expression of further biomarker(s) in the cell comprises determining at least about one, at least about two, at least about three or at least about four biomarker(s) selected from the group consisting of: CD49d, CD34, CD106, CD11b in the cell. In various embodiments, the cell is identified as an early committed neutrophil when it is determined to have one or more of the following expression profiles: $CD49d^{hi/+}$, $CD34^{hi/+}$, $CD106^{lo/-}$ and $CD11b^{lo/-}$. In various embodiments, the cell is identified as an intermediate neutrophil progenitor that is downstream in neutrophil lineage to the early committed neutrophil progenitor when it is determined to have one or more of the following expression profiles: $CD49d^{int/lo/-}$, $CD34^{lo/-}$, $CD106^{hi/+}$ and $CD11b^{hi/+}$.

In various embodiments, determining/measuring one or more physical property associated with the cell comprises determining/measuring a granularity or complexity of the cell and/or a nucleus morphology of the cell. In various embodiments, the cell is identified as an early committed neutrophil when it is determined to have no or minimal hollowing of the nucleus that falls below a threshold diameter. In various embodiments, the cell is identified as an intermediate neutrophil progenitor that is downstream in neutrophil lineage to the early committed neutrophil progenitor when it is determined to have a hollowing of the nucleus that corresponds to or exceeds the threshold diameter. In various embodiments, the cell is identified as an early committed neutrophil when it is determined to have low granularity or complexity. In various embodiments, the cell is identified as an intermediate neutrophil progenitor that is downstream in neutrophil lineage to the early committed neutrophil progenitor when it is determined to have high granularity or complexity. Granularity or complexity may be determined/measured by, for example, by evaluating a side-scatter property in flow cytometry. In various embodiments therefore, the cell is identified as an early committed neutrophil when it is determined to have low side scatter. In various embodiments therefore, the cell is identified as an intermediate neutrophil progenitor that is downstream in neutrophil lineage to the early committed neutrophil progenitor when it is determined to have high side scatter.

In some embodiments, where the cell is identified as a neutrophil progenitor, the method further comprises determining an expression of a further biomarker selected from CD49d and/or a side-scatter property of the neutrophil progenitor; and identifying a subtype of the neutrophil progenitor based on the expression of the further biomarker and/or the side-scatter property. In various embodiments, where the cell is determined to have $CD49d^{hi/+}$ expression, the cell is identified as an early committed neutrophil progenitor. In various embodiments, where the cell is determined to have $CD49d^{int/lo/-}$ expression, the cell is identified as an intermediate neutrophil progenitor that is downstream in neutrophil lineage to the early committed neutrophil progenitor. In various embodiments, where the cell is determined to have low side scatter, the cell is identified as an early committed neutrophil progenitor. In various embodiments, where the cell is determined to have high side scatter, the cell is identified as an intermediate neutrophil progenitor that is downstream in neutrophil lineage to the early committed neutrophil progenitor. In various embodiments therefore, where the neutrophil progenitor is determined to be $CD49d^{hi/+}$ and/or $SSC^{lo}$, the neutrophil progenitor is identified as an early committed neutrophil progenitor, and wherein where the neutrophil progenitor is determined to be $CD49d^{int/lo/-}$ and/or $SSC^{hi}$, the neutrophil progenitor is identified as an intermediate neutrophil progenitor that is downstream in neutrophil lineage to the early committed neutrophil progenitor. Embodiments of the method may also be used to determine a stage of differentiation and/or development of a neutrophil progenitor. For example, a neutrophil progenitor that is determined to be CD49d$^{hi/+}$ and/or SSC$^{lo}$ may be identified as being in an earlier stage of differentiation and/or development than a neutrophil progenitor that is determined to be CD49d$^{int/lo/-}$ and/or SSC$^{hi}$.

The expression of the biomarker may be determined or measured by methods known in the art. In some embodiments, determining/measuring an expression of a biomarker in a cell comprises performing RNA sequencing such as single-cell RNA sequencing. In some embodiments, determining/measuring an expression of a biomarker in a cell comprises contacting/incubating the cell with an agent for detecting the biomarker, for example, a molecule capable of binding to the biomarker or having affinity for the biomarker. Examples of agents/molecules that may be employed include, but are not limited to, small molecules, peptides, proteins, antigen-binding proteins, antibodies, polynucleotides, aptamers, fragments thereof and the like. In some embodiments, determining/measuring an expression of a biomarker in a cell comprises contacting/incubating the cell with at least about one, at least about two, at least about three, at least about four, at least about five, at least about six, at least about seven, at least about eight, at least about nine or at least about ten agents/molecules. In some embodiments, determining/measuring an expression of a biomarker in a cell comprises contacting/incubating the cell with no more than about ten, no more than about nine, no more than about eight, no more than about seven, no more than about six, no more than about five, no more than about four, no more than about three, no more than two or not more than about one agent/molecule.

In various embodiments, the molecule comprises an antigen-binding molecule. Examples of antigen-binding molecules include, but are not limited to, antibodies and fragments thereof such as antigen binding fragments. Non-limiting examples of antigen binding fragments include one or more fragments or portions of an antibody that retain the ability to specifically bind to an antigen (e.g., CD71), or synthetic modifications of an antibody fragments that retain the desired binding ability to the antigen. In various embodiments, antigen binding fragments include single domain antibodies, further engineered molecules (such as, but is not limited to diabodies, triabodies, tetrabodies, minibodies, and the like), Fab fragments, Fab' fragments, F(ab')2 fragments, Fd fragments, Fv fragments, single-chain Fv (scFv) molecules, seFv molecules, scFv dimer, BsFv molecules, dsFv molecules, (dsFv)2 molecules, dsFv-dsFv' molecules, Fv fragments, dAb fragments, bispecific antibodies, ds diabodies, nanobodies, domain antibodies, bivalent domain antibodies, and minimal recognition units consisting of the amino acid residues that mimic the hypervariable region of an antibody (e.g. an isolated complementarity determining region (CDR)).

In various embodiments, determination of the expression of the biomarker comprises contacting the cell with one or more antibodies against the biomarker. In various embodiments, the antibody is coupled or conjugated to a label, for example, a fluorescent label such as a fluorescent dye. In various embodiments, flow cytometry is performed to determine the expression of the biomarker.

In various embodiments, there is provided a method of sorting and/or separating neutrophil progenitors from a cell population or a method of enriching neutrophil progenitors in a cell population, the method comprising: selecting for cells having/expressing one or more of the biomarkers as described herein. In various embodiments, there is provided a method of sorting and/or separating neutrophil progenitors from a cell population, the method comprising: selecting for cells having at least about one, at least about two, at least about three, at least about four, at least about five, at least about six, at least about seven or at least about eight of the following expression profiles: CD71$^{hi/+}$, LOX-1$^{int/lo/-}$, CD164$^{hi/+}$, CD112$^{hi/+}$, CD181$^{int/lo/-}$, TACSTD2$^{hi/+}$, CD11b$^{lo/-}$ and/or CD49d$^{int/hi/+}$. In some embodiments, the method comprises selecting for CD71-expressing cells or CD71$^{hi/+}$ cells.

In various embodiments, the cell population is derived from cord blood and/or bone marrow. In various embodiments, the cell population is derived from fetal bone marrow. In various embodiments therefore, the cell population comprises or consists of cord blood cells, bone marrow cells and/or fetal bone marrow cells.

In various embodiments, the cord blood and/or bone marrow is collected from a mammal, such as, but not limited to, humans, non-human primates, canine, murine (e.g., mouse, rat, rabbit, and the like) and the like. In some embodiments, the cord blood and/or bone marrow is collected from a mouse or a human. In some embodiments therefore, the cell population comprises at least one selected from the group consisting of: mouse cord blood cells, mouse bone marrow cells, mouse fetal bone marrow cells, human cord blood cells, human bone marrow cells and human fetal bone marrow cells. In some embodiments, the cell population consists of mouse cord blood cells, mouse bone marrow cells, mouse fetal bone marrow cells, human cord blood cells, human bone marrow cells and/or human fetal bone marrow cells. In various examples, there is provided a method isolating a subset of neutrophil progenitors (proNeus) from human biological samples such as human cord blood and fetal bone marrow comprising the use of CD71 as a selection marker.

In various embodiments, the method further comprises culturing the neutrophil progenitors to obtain proliferation and/or differentiation of the neutrophil progenitors, for example, to mature neutrophils. In various embodiments, the mature neutrophils comprise CD16$^+$CD10$^+$ mature neutrophils.

In various embodiments, the method further comprises administering the neutrophil progenitors and/or progenies thereof (e.g., progenies resulting from the proliferation of the neutrophil progenitors and/or differentiation of the neutrophil progenitors) to a subject in need thereof. Examples of a subject in need thereof include, but is not limited to, a neutropenic subject, a subject having cancer, a subject having an infection (e.g., bacterial and/or fungal infections), a subject undergoing chemotherapy and/or radiation therapy, a subject having disorder of the blood, a subject having disorder of the bone marrow, a subject having disorder of the immune system, a subject who is a candidate for hematopoietic stem cell transplantation, a subject who is a candidate for myeloablative therapy and a subject having one or more of the following conditions: multiple myeloma, leukemia, lymphomas, aplastic anemia, thalassemia, sickle cell disease, severe combined immune deficiency syndrome and the like. In one embodiment, the subject has neutropenia.

In some embodiments, the cell population (i.e., the cell population which neutrophil progenitors is being separated from or in which neutrophil progenitors is being enriched in) is obtained/derived from the subject. In some embodiments therefore, the method further comprises a step of obtaining the cell population from the subject, for example, prior to a procedure such as hematopoietic stem cell transplantation or myeloablative therapy. In some embodiments, the cell population is obtained/derived from a donor.

In various embodiments, the selecting step comprises contacting/incubating the cell with agents for detecting the biomarker(s), for example, molecule(s) capable of binding to the biomarker(s) or having affinity for the biomarker(s) as described herein.

In some embodiments, the selecting step comprises contacting/incubating the cell with at least about one, at least about two, at least about three, at least about four, at least about five, at least about six, at least about seven, at least about eight, at least about nine or at least about ten agents/molecules. In some embodiments, the selecting step comprises contacting/incubating the cell with no more than about ten, no more than about nine, no more than about eight, no more than about seven, no more than about six, no more than about five, no more than about four, no more than about three, no more than two or not more than about one agent/molecule. In some embodiments, the molecule comprises an antibody. In various embodiments, the selecting step comprises contacting the cells with one or more antibodies against one or more of CD71, LOX-1, CD164, CD112, CD181, TACSTD2, CD11b and/or CD49d. The antibody may be coupled or conjugated to a label, for example, a fluorescent label such as a fluorescent dye. In various embodiments, flow cytometry is performed to select for neutrophil progenitors. In various embodiments, fluorescence-activated cell sorting (FACS) is used to select for neutrophil progenitors.

In various embodiments, the method further comprises washing the cells. In various embodiments, the method further comprises removing the antibodies bound to the biomarkers. For example, the REAlease Releasable Antibody technology (Miltenyl Biotech) may be utilized. A REAlease Release Reagent may be added to allow the spontaneous dissociation of the antibodies bound. In various embodiments, the method further comprises expanding the cells (e.g., in vitro) to dilute the bound antibodies. In various embodiments, the method further comprises expanding the cells, and subsequently removing those cells with antibodies bound thereto. Advantageously, dilution and/or removal of antibodies minimises or eliminates the problem of the antibodies interacting with the host immune system (e.g., the human immune system) when the cells (e.g., neutrophil progenitors and progenies thereof) are infused into the host, particularly when the antibodies are from a different species than the host (for example, when mouse-derived monoclonal antibodies are used to isolate neutrophil progenitors for infusion into a human).

As compared to using hematopoietic stem and progenitors (HSPCs) as the starting material and expanding neutrophils from these cells, embodiments of the method provide a more efficient way of producing neutrophils as the HSPCs may differentiate and expand into various cell lineages, resulting in lower yield and a longer processing time. The robust supply of neutrophils that may be produced by embodiments of the method may be advantageously harnessed for therapy or research (e.g., in vitro research).

Neutrophil progenitors may be used for large scale production of neutrophils for therapy (e.g., cell therapy) in, for example, myelo-ablated and neutropenic patients and for research. In various embodiments therefore, there is provided a composition that is enriched in neutrophil progenitors and/or progenies thereof, for example, neutrophil progenitors having at least about one, at least about two, at least about three, at least about four, at least about five, at least about six, at least about seven or at least about eight of the following expression profiles: CD71$^{hi/+}$, LOX-1$^{int/lo/-}$, CD164$^{hi/+}$, CD112$^{hi/+}$, CD181$^{int/lo/-}$, TACSTD2$^{hi/+}$, CD11b$^{lo/-}$ and/or CD49d$^{int/hi/+}$. In one embodiment, the composition is enriched in CD71-expressing or CD71$^{hi/+}$ neutrophil progenitors and/or progenies thereof. In various embodiments, the amount/concentration of neutrophil progenitors and/or progenies thereof contained in the enriched composition is higher than the amount/concentration of neutrophil progenitors and/or progenies thereof naturally found in an animal or a human biological sample such as blood and bone marrow. In various embodiments, the composition further comprises one or more components of blood such as red blood cells, white blood cells of various types and platelets. In various embodiments, the composition comprises one derived/obtained from the bone marrow and/or blood (e.g., cord blood, peripheral blood etc.) which is subsequently enriched. In various embodiments, the composition comprises one derived/obtained from human bone marrow and/or human blood.

In various embodiments, there is provided a composition consisting of neutrophil progenitors and/or progenies thereof, for example, neutrophil progenitors having at least about one, at least about two, at least about three, at least about four, at least about five, at least about six, at least about seven or at least about eight of the following expression profiles: CD71$^{hi/+}$, LOX-1$^{int/lo/-}$, CD164$^{hi/+}$, CD112$^{hi/+}$, CD181$^{int/lo/-}$, TACSTD2$^{hi/+}$, CD11b$^{lo/-}$ and/or CD49d$^{int/hi/+}$. In various embodiments, the composition consists of CD71-expressing neutrophil progenitors and/or CD71$^{hi/+}$ neutrophil progenitors and/or progenies thereof. In various embodiments, the composition consists of neutrophils derived from neutrophil progenitors, for example, neutrophil progenitors having at least about one, at least about two, at least about three, at least about four, at least about five, at least about six, at least about seven or at least about eight of the following expression profiles: CD71$^{hi/+}$, LOX-1$^{int/lo/-}$, CD164$^{hi/+}$, CD112$^{hi/+}$, CD181$^{int/lo/-}$, TACSTD2$^{hi/+}$, CD11b$^{lo/-}$ and/or CD49d$^{int/hi/+}$, or CD71-expressing neutrophil progenitors or CD71$^{hi/+}$ neutrophil progenitors.

In various embodiments, the composition comprises a therapeutic composition. In various embodiments, there is provided embodiments of the composition for use in therapy. In various embodiments, there is provided embodiments of the composition for use in cell therapy. In various embodiments, there is provided embodiments of the composition for use in treating a condition selected from the group consisting of: a blood disorder, a bone marrow disorder, an immune system disorder, cancer, blood cancer, an infection (e.g., bacterial and/or fungal infections), neutropenia, multiple myeloma, leukemia, lymphomas, aplastic anemia, thalassemia, sickle cell disease, severe combined immune deficiency syndrome and the like. In one embodiment, there is provided embodiments of the composition for use in treating neutropenia.

In various embodiments, there is provided use of embodiments of the composition in the manufacture of a medicament for treating a condition selected from the group consisting of: a blood disorder, a bone marrow disorder, an immune system disorder, cancer, blood cancer, an infection (e.g., bacterial and/or fungal infections), neutropenia, multiple myeloma, leukemia, lymphomas, aplastic anemia, thalassemia, sickle cell disease, severe combined immune deficiency syndrome and the like. In one embodiment, there is provided use of embodiments of the compositions in the manufacture of a medicament for treating neutropenia.

In various embodiments, there is provided a method of treating a condition selected from the group consisting of: a blood disorder, a bone marrow disorder, an immune system disorder, cancer, blood cancer, an infection (e.g., bacterial and/or fungal infections), neutropenia, multiple myeloma, leukemia, lymphomas, aplastic anemia, thalassemia, sickle cell disease, severe combined immune deficiency syndrome and the like in a subject, the method comprising administering to the subject embodiments of the composition. In some embodiments, the composition is derived from the subject (for example, prior to enrichment). In some embodiments, the composition is not derived from the subject. In some embodiments, the composition is derived from a donor. In some embodiments, the method comprises a method of treating neutropenia comprising the administration of CD71$^{hi/+}$ or CD71-expressing neutrophil progenitor (proNeus) to neutropenic patients.

In various embodiments, there is provided use of embodiments of the compositions in the manufacture of a transfusion composition, for example, for treating a condition selected from the group consisting of: a blood disorder, a bone marrow disorder, an immune system disorder, cancer, blood cancer, an infection (e.g., bacterial and/or fungal infections), neutropenia, multiple myeloma, leukemia, lymphomas, aplastic anemia, thalassemia, sickle cell disease, severe combined immune deficiency syndrome and the like. In one embodiment, there is provided use of embodiments of the compositions in the manufacture of a transfusion composition for treating neutropenia.

In various embodiments, there is provided a method of preparing a transfusion composition or a composition for transplantation e.g., for a subject such as a neutropenic subject, the method comprising: enriching a composition (or a starting composition) for neutrophil progenitors and/or progenies thereof, for example, neutrophil progenitors having at least one of the following expression profiles: CD71$^{hi/+}$, LOX-1$^{int/lo/-}$, CD164$^{hi/+}$, CD112$^{hi/+}$, CD181$^{int/lo/-}$, TACSTD2$^{hi/+}$, CD11$^{lo/-}$ and/or CD49d$^{int/hi/+}$. In various embodiments, the method comprises enriching the composition (or the starting composition) for CD71-expressing or CD71$^{hi/+}$ neutrophil progenitors and/or progenies thereof. In various embodiments, the composition (or the starting composition) is derived/obtained from the bone marrow and/or blood (e.g., cord blood, peripheral blood etc.). In various embodiments, the composition (or the starting composition) is derived/obtained from human bone marrow and/or blood. The composition (or the starting composition) may be derived/obtained from the subject or a donor. In some embodiments thereof, the method comprises obtaining the composition (or the starting composition) from the subject prior to enrichment.

In various embodiments, the enriching step comprises contacting the composition (or the staring composition) with one or more agents for detecting the biomarkers, e.g., molecules capable of binding to one or more of the biomarkers as described herein. In various embodiments, the enriching step comprises contacting the composition (or the staring composition) with one or more antibodies against one or more of CD71, LOX-1, CD164, CD112, CD181, TACSTD2, CD11b and/or CD49d.

In various embodiments, there is provided a method of producing mature neutrophils for use in transplantation comprising of the steps: isolating a subset of neutrophil progenitor (proNeus) from human biological samples such as human cord blood and fetal bone marrow comprising the use of CD71 as a selection marker; culturing the isolated neutrophil progenitor population, for example, for three days in serum-free media containing myeloid expansion supplement for expansion.

In various embodiments, there is provided a method of identifying an agent that is capable of increasing the amount/concentration of neutrophils and/or neutrophil progenitors in a composition or in a subject, the method comprising: determining the amount/concentration of neutrophils and/or neutrophil progenitors in a first sample obtained from the composition or the subject at a first timepoint before the administration/treatment of a candidate agent to the composition or the subject, determining the amount/concentration of neutrophils and/or neutrophil progenitors in a second sample obtained from the composition or the subject at a second timepoint after the administration/treatment of the candidate agent to the composition or the subject, and comparing the amount/concentration of neutrophils and/or neutrophil progenitors in the first sample and second sample. In various embodiments, the method further comprises concluding that the candidate agent is an agent capable of increasing the amount/concentration of neutrophils and/or neutrophil progenitors when the amount/concentration of neutrophils and/or neutrophil progenitors in the second sample is increased relative to the first sample and concluding that the candidate agent is not an agent capable of increasing the amount/concentration of neutrophils and/or neutrophil progenitors when the amount/concentration of neutrophil progenitors in the second sample is not increased relative to the first sample. In various embodiments, determining the amount/concentration of neutrophils and/or neutrophil progenitors in the first and/or second sample comprising determining the amount/concentration of cells having at least one of the following expression profiles: CD71$^{hi/+}$, LOX-1$^{int/lo/-}$, CD164$^{hi/+}$, CD112$^{hi/+}$, CD181$^{int/lo/-}$, TACSTD2$^{hi/+}$, CD11$^{lo/-}$ and/or CD49d$^{int/hi/+}$. In various embodiments, determining the amount/concentration of neutrophils and/or neutrophil progenitors in the first and/or second sample comprising determining the amount/concentration of CD71-expressing or CD71$^{hi/+}$ cells.

In various embodiments, there is provided a kit, optionally a kit for use in a method as described herein, the kit comprising an agent for detecting biomarker, for example, a molecule capable of binding to the biomarker or having affinity for the biomarker. In various embodiments, the kit comprises at least about one, at least about two, at least about three, at least about four, at least about five, at least about six, at least about seven, or at least about eight molecules capable of binding to at least about one, at least about two, at least about three, at least about four, at least about five, at least about six, at least about seven or at least about eight of the biomarkers as described herein. In various embodiments, the kit comprises molecule(s) for binding to at least about one, at least about two, at least about three, at least about four, at least about five, at least about six, at least about seven or at least about eight biomarker(s) selected from the group consisting of: CD71, LOX-1, CD164, CD112, CD18, TACSTD2, CD11b and CD49d. In various embodiments, the kit comprises antibody or a plurality of antibodies for binding to at least about one, at least about two, at least about three, at least about four, at least about five, at least about six, at least about seven or at least about eight biomarker(s) selected from the group consisting of: CD71, LOX-1, CD164, CD112, CD181, TACSTD2, CD11b and CD49d.

In various embodiments, there is provided a method or a product as described herein.

EXAMPLES

Figures 1D, 1E:
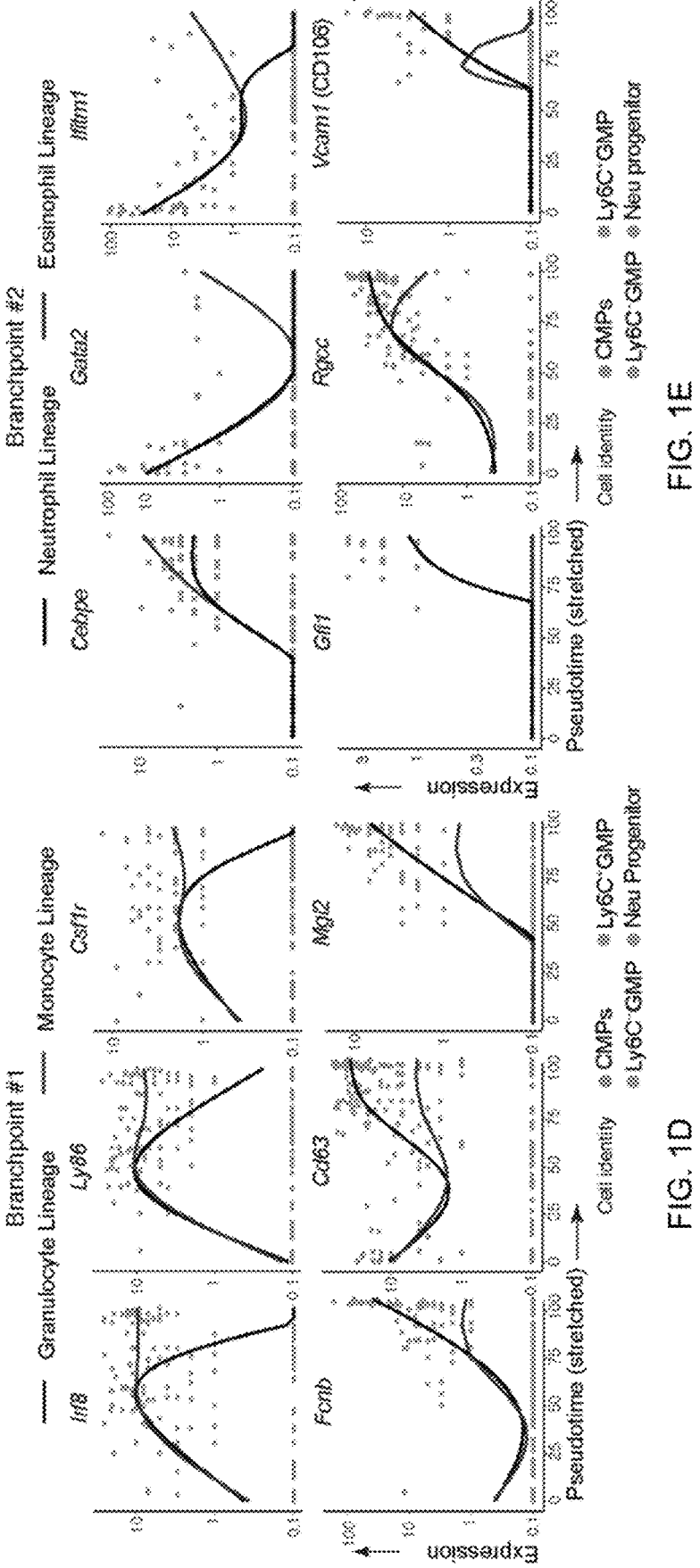
FIG. 1. Single-cell RNA sequencing analysis reveal GMPs as a heterogeneous group of progenitors. (A) Reanalysis of available and annotated single-cell datasets containing mouse BM GMPs. Normalised counts from each dataset were downloaded and analysed using Seurat package. Louvain clustering was performed and annotations were assigned based on key lineage-related genes. (B) Gating strategy containing mouse BM CMPs, Ly6C⁻GMPs and Ly6C⁺GMPs. Colored dots represent index-sorted cells used for Smart-Seq2 scRNA-Seq. (C) (top) Sequenced cells in (B) are subjected to Monocle2 trajectory prediction. Cells are aligned according to pseudotime from left to right. Branching points are indicated and (bottom) the description of each lineage is shown. (D) Branchpoint #1 analysis of lineage-related genes and their expression across pseudotime between granulocytes (black line) and monocytes (grey line) (See also FIG. 8D). (E) Branchpoint #2 analysis of lineage-related genes and their expression across pseudotime between neutrophils (black line) and eosinophils (grey line) (See also FIG. 8E). (F) Total transcripts of CMP and GMP subsets, and sorted downstream neutrophil (preNeus) and monocyte (TpMos) precursors, are subjected to a PCA projection. (G) Smart-Seq2 sequenced cells dataset was integrated with the 10× (Tabula Muris) whole mouse BM dataset using Seurat v3. Data integration quality is represented in the overlay plot and (H) respective plots of each dataset indicating cell identities and relative cluster localisations. (See also FIG. 8).

Example embodiments of the disclosure will be better understood and readily apparent to one of ordinary skill in the art from the following discussions and if applicable, in conjunction with the figures. It will be appreciated that the example embodiments are illustrative, and that various modifications may be made without deviating from the scope of the invention. Example embodiments are not necessarily mutually exclusive as some may be combined with one or more embodiments to form new exemplary embodiments.

The granulocyte-monocyte progenitor (GMP) is a Lin$^{neg}$cKit⁺CD34$^{hi}$CD16/32$^{hi}$ lineage-primed progeny derived from common myeloid progenitors (CMPs) that forms characteristic granulocyte-macrophage (GM) colonies in culture. GMPs are known for their potential to generate various myeloid progenies such as neutrophils and monocytes. Since GMPs generate both monocytes and neutrophils, their potential raises important questions during circumstances that demand conflicting needs of these two cell subsets.

In particular, neutrophils are produced in much larger quantities compared to monocytes and their lineage selection requires the repression of monocyte fate with Gfi1. Furthermore, kinetic labelling studies have demonstrated a much longer transit time of neutrophils in the bone marrow compared to monocytes. It thus remains unclear how GMPs adjust their functional output according to different demands, and whether the disparity in transit time between neutrophils and monocytes is due to distinctions between progenitor characteristics downstream or heterogeneity that already exists within GMPs.

To address these questions, recent advances in single cell transcriptomics have attempted to determine the developmental cell states of each cell, which has led to a discovery of heterogeneity in myeloid lineages and cell fate decisions. Specifically, it has been proposed that GMPs undergo a mixed-lineage state prior to granulocyte and monocyte specification. While these results provided insights into the lineage priming program within the GMP hierarchy, there is a lack of functional validation on how expression or suppression of lineage-affiliated genes will translate into cellular heterogeneity. Furthermore, although lineage heterogeneity within GMPs has been proposed, it is unclear if committed progenitors already exist among these progenitors and how they may behave differently during inflammation.

An attempt was made to resolve this heterogeneity with Ly6C and CD115 (CSF-1R) being utilized to subset GMPs into Ly6C⁻GMPs and Ly6C⁺CD115$^{hi}$ monocyte (MPs) and Ly6C⁺CD115$^{lo}$ granulocyte progenitors (GPs). However, these markers alone were not sufficient to fully resolve the strict lineage commitment of each progenitor subset, indicating that better markers are required to evaluate the heterogeneity of these progenitors. Particularly, better markers are required for identifying a neutrophil progenitor.

Neutrophils are important immune cells which provide protection against bacterial and fungal infections. Due to their short lifespan, neutrophils are continuously produced by specialised bone marrow progenitors to meet the daily demand of 100 million cells per day. Neutrophil development begins with long-lived hematopoietic stem cells, which give rise to highly proliferative progenitors that expand in numbers to generate an adequate supply of mature effector neutrophils for immune surveillance and protection against microbial threats. Despite their importance, the identity and characteristics of a committed neutrophil progenitor are yet to be found.

The inventors have previously reported the identification of neutrophil precursors known as preNeus. While these precursors developed into neutrophils, they were unable to form colonies in vitro, indicating that they are not the true progenitor cells for neutrophils.

In this disclosure, through a combination of single-cell transcriptomic and proteomic analyses, the inventors successfully identified an early committed progenitor within the GMPs responsible for the strict production of neutrophils, which they have termed as proNeu1. The comprehensive dissection of GMP hierarchy led to the further identification of a previously unknown intermediate proNeu2 population. Similar populations could be detected in human samples.

The early committed neutrophil progenitor, proNeu1, is already present within the heterogenous population of GMPs. ProNeu1 is shown to give rise to the intermediate progeny proNeu2, which subsequently differentiates into downstream populations. Importantly, it was found that proNeu1 but not proNeu2, expanded extensively and specifically in the early phase of septic inflammation at the expense of monocytic differentiation.

The two subsets of neutrophil progenitors, proNeu1 and proNeu2, which are responsible for the extensive production of neutrophils in humans, are characterised by distinct protein surface marker expression profiles such as CD71 expression. Based on these surface markers, the inventors were able to isolate these progenitors and demonstrate their development into mature CD16⁺CD10⁺ neutrophils in vitro.

Collectively, the findings complete the neutrophil maturation trajectory roadmap and call for a revision of the classical GMP nomenclature. The disclosure further exemplifies the importance of understanding progenitor identities to study their function in health and disease.

Results

GMPs Contain a Heterogeneous Group of Lineage-Committed Progenitors

Figure 8A:
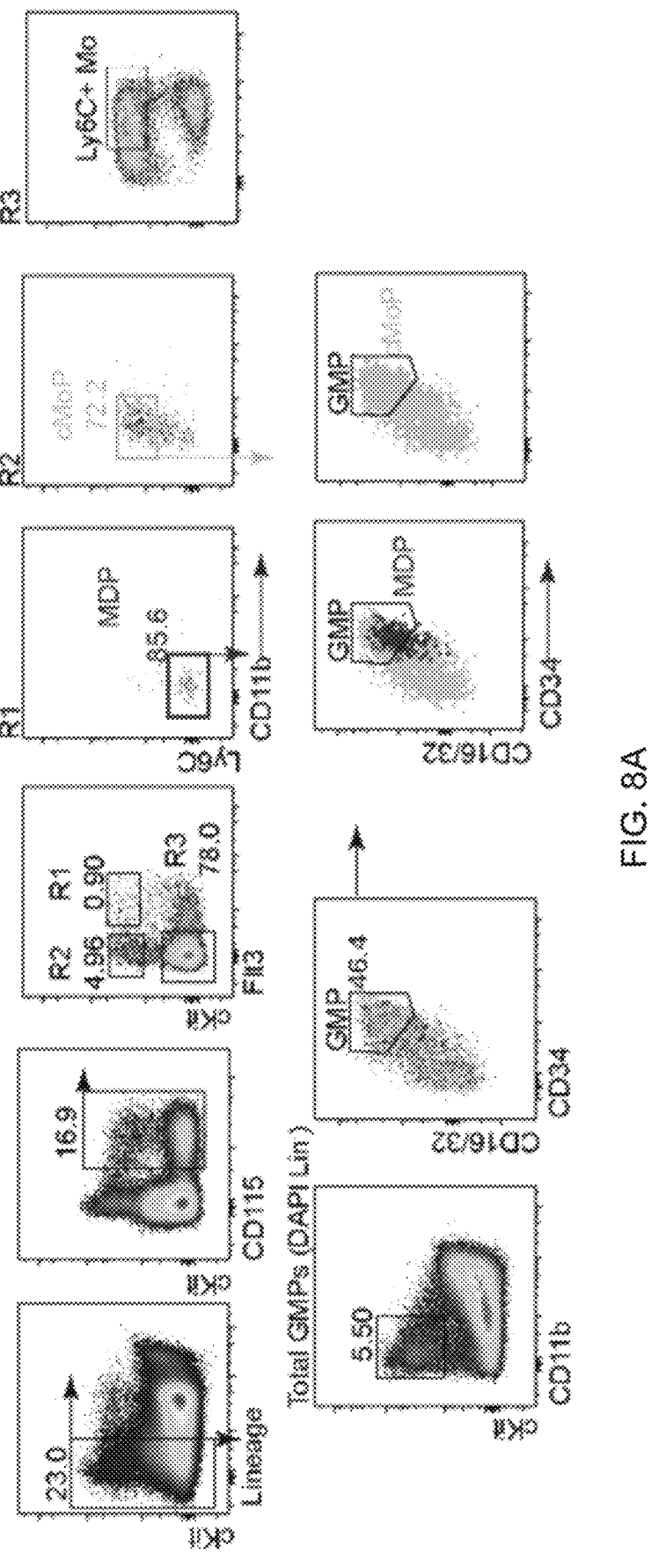
FIG. 8. GMPs are a heterogeneous group of progenitors including known monocyte progenitors. (A) (top) Gating strategy of MDPs (monocyte-dendritic cell progenitors) (in dark grey) and cMoPs (common monocyte progenitor) (in light grey) according to (Hettinger et al., 2013). (bottom) Back-gating and overlap of each population onto traditionally gated GMPs (granulocyte-monocyte progenitors) is shown. (B) (left) Gating strategy of BM progenitor populations according to (Liu et al., 2019) and (right) overlap of gated population with conventional GMP gating strategy. (C) Sorting strategy of preNeus and TpMo used for single-cell sequencing. (D-E) Branch expression analysis modelling (BEAM) of (D) branchpoint #1 and (E) branchpoint #2 using Monocle2. Gene expression is represented from low (light) to high (dark) levels. (F) Gene expression analysis of neutrophil-related genes in the indicated subsets. (G) mRNA and corresponding protein marker expression level plots of the index-sorted cells.
Figures 8B, 8C:
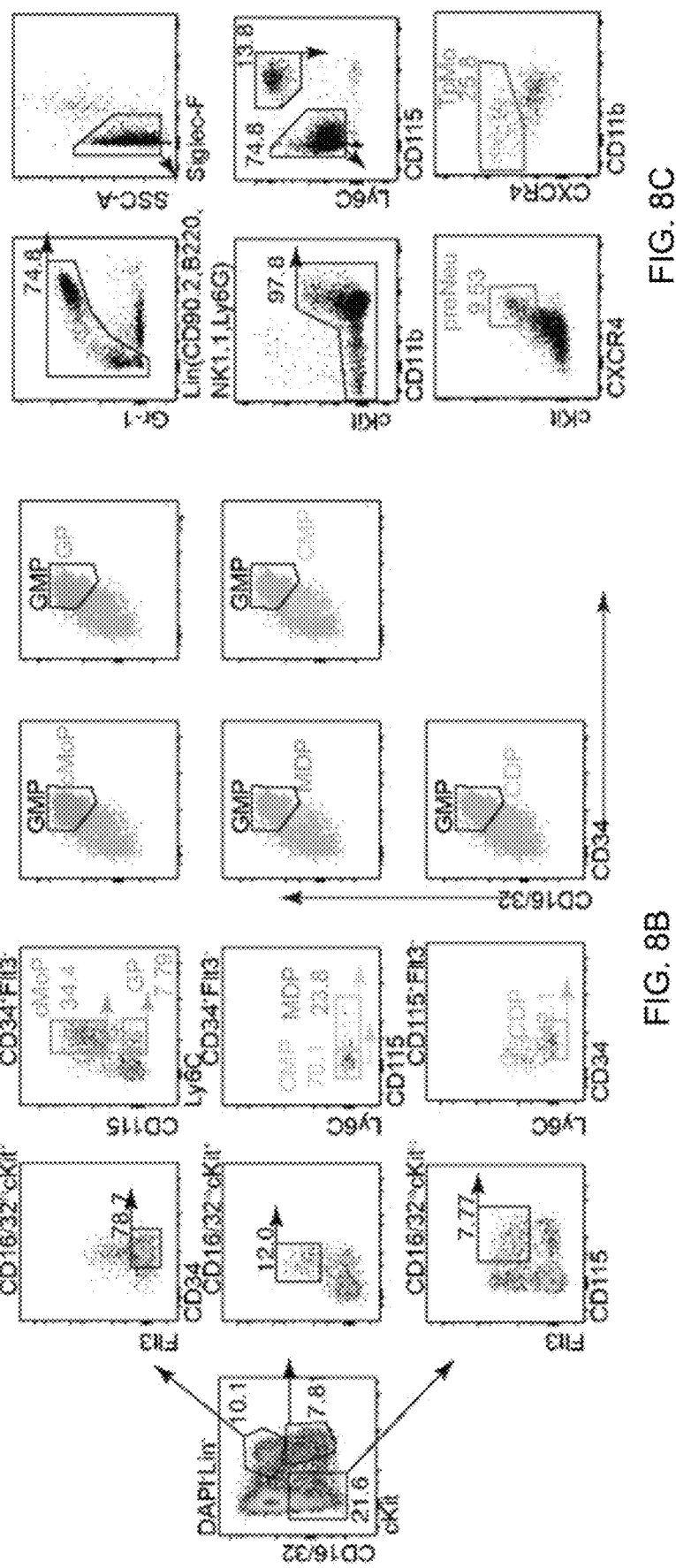

GMPs are known to give rise to granulocytes, such as neutrophils, and monocytes. As such, GMPs were commonly assumed to possess oligo-potent differentiation potential. However, contrary to this assumption, recent studies have suggested that the GMPs are instead, a heterogeneous mixture containing lineage-committed precursors. To resolve these two viewpoints and to provide a comprehensive understanding of the true hematopoietic potential of cells within this population of cells, the inventors investigated the GMP population by performing an analysis with published repositories of single-cell transcriptomic datasets (Giladi et al., 2018; Olsson et al., 2016). By extracting the annotated GMPs (based on Lin⁻cKit⁺Sca-1⁻CD34$^{hi}$CD16/32$^{hi}$), the inventors performed t-Distributed Stochastic Neighbour Embedding (t-SNE) (Maaten and Hinton, 2008) analysis and confirmed that GMPs contained a mixed population of monocytic, neutrophilic, eosinophilic and basophilic progenitor subsets (FIG. 1A). Notably, in addition to current published literature, the inventors further discovered multiple clusters pertaining to different granulocyte and monocyte lineages based on known lineage restricted genes. These multiple clusters possessed key monocytic genes like Irf8, Ly86 and Csf1r (FIG. 1A), and their gene expression correlated with the presence of common monocytic progenitors (cMoPs), monocyte progenitors (MPs) and monocyte-dendritic progenitors (MDPs) (FIGS. 8A and 8B). The inventors also observed a neutrophil-like cluster containing high expressions of neutrophil elastase (Elane) and ficollin (Fcnb), which are known genes of the neutrophil lineage. These analyses provide further insight into the heterogeneity of progenitors within GMPs and indications of their cell lineage commitment at the transcriptomic level.

To further look into the various GMP developmental and transitional states leading towards lineage commitment, single-cell RNA-Seq analysis was performed on index-sorted CMPs and total GMPs. The inventors also sorted late precursors, preNeus and TpMos (transitional pre-monocytes), as reference points for neutrophil and monocyte differentiation respectively (FIG. 8C). Back gating of the sorted GMP population showed the presence of Ly6C⁺ and Ly6C⁻ subsets (FIG. 1B). Monocle (Qiu et al., 2017) was then utilised to order the cells in pseudotime, from CMPs to fully specified progenitors, allowing for the understanding of the various developmental and trajectory states. Monocle then revealed two distinct branchpoints (FIG. 1C). Deeper analysis on these branchpoints showed key fate-determining genes that change over the course of development suggestive of a monocyte-granulocyte at point 1 (FIG. 1D) and a neutrophil-eosinophil determination point at point 2 (FIG. 1E). These analyses revealed an initial down-regulation of monocytic fate-determining genes (Ly86, Csf1r, Irf8), followed by a combinatorial and selective up-regulation of neutrophil-related genes (Gfi1, Rgcc, Vcam1) that are both important for initiating the neutrophil fate (FIGS. 8D and S8E).

Figure 8G:
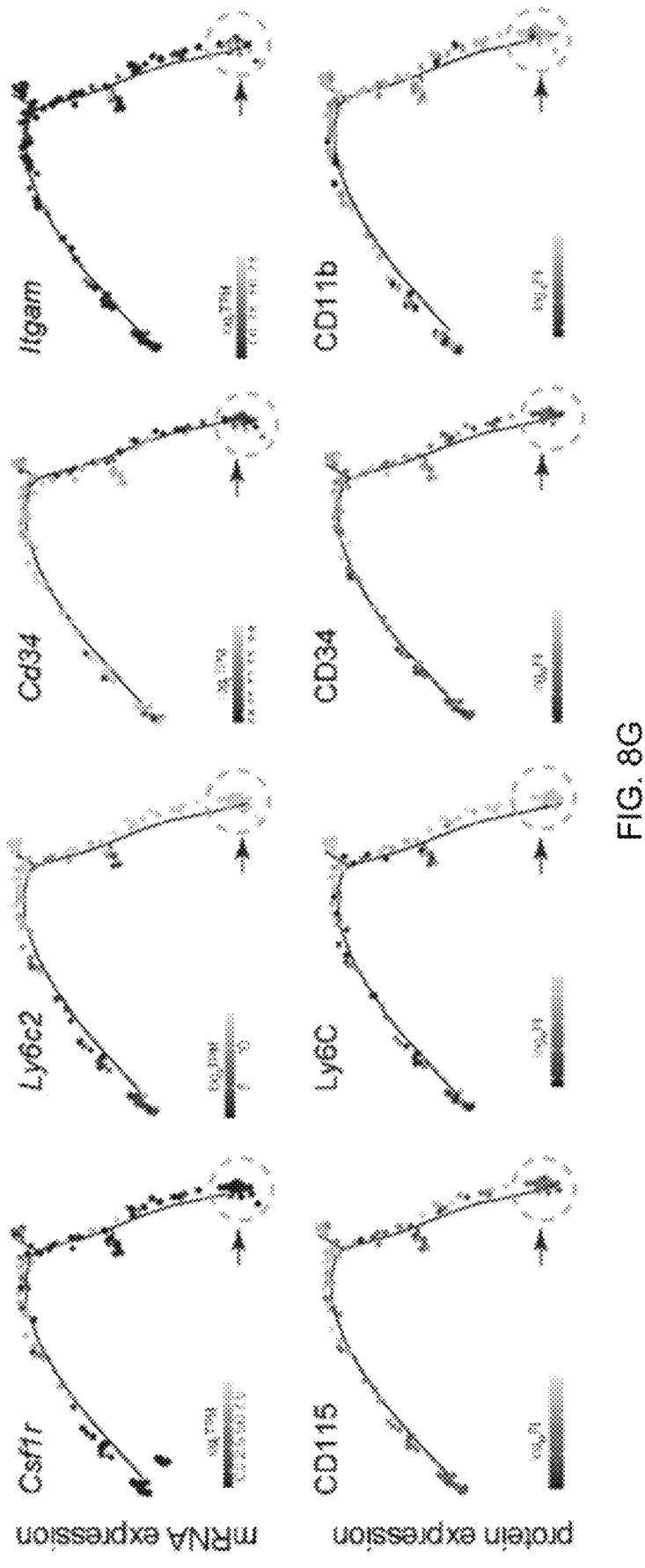

Upon further analysis with Monocle, the inventors noticed the presence of a specified progenitor population at the terminal end state of the neutrophil branchpoint within the Ly6C⁺ fraction of GMPs (FIG. 1C). These cells possessed the highest expression of known neutrophil-specific genes, such as Gfi1 and S100a8 among others (FIG. 8F). To determine if this population of cells could be putative neutrophil progenitors, these cells were mapped onto a principal component analysis (PCA) of total transcripts and it was discovered that they clustered closer to preNeus along PC2 away from TpMos (FIG. 1F). These putative neutrophil progenitors possessed low levels of CD115 and high levels of Ly6C, both at the mRNA and protein level (FIG. 8G). Furthermore, by performing single-cell data integration (Stuart et al., 2018) with the Tabula Muris™ BM dataset (Schaum et al., 2018), the inventors were able to confirm the cell identities from the dataset (FIG. 1G). Visualisation of the integration revealed a precise mapping of preNeus and TpMos to their respective lineages, while CMPs mapped towards the erythrocytic lineage as well as the dendritic cell lineage (FIG. 1H). Importantly, it was observed that the putative neutrophil progenitors associated with the initial neutrophil branch point, suggesting that this population can be the early progenitors for neutrophil development (FIG. 1H). Taken together, the data suggests a population of putative neutrophil progenitors exist within the GMP and are responsible for the generation of neutrophils.

InfinityFlow Resolves GMP Heterogeneity and Identifies Population Discriminating Surface Markers Although transcriptomic signatures provide a useful means in determining cell states, they do not confirm a cell's identity or allow further downstream analysis. Therefore, to validate the GMP heterogeneity on a proteomic level, the expression of 261 surface markers (LEGENDScreen™, Biolegend) (Table 1) on total mouse BM cells was evaluated by flow cytometry. The InfinityFlow (Dutertre et al., 2019) pipeline was then used to predict the co-expression of every surface marker tested and this predicted expression information was concatenated into a single analysis file (FIG. 2A). GMPs stained positively for 81 of these markers. The analysis was first restricted to these 81 markers, which were then used to perform a t-SNE analysis on GMPs only. With PhenoGraph (Levine et al., 2015), the inventors could subset GMPs into 10 subpopulations, confirming on a proteomic level that GMPs are a mix of progenitors (FIG. 2B). Using the top discriminating markers for each cluster, the inventors were able to ascertain the identities of the known monocyte (cluster 2, 6 and 7), eosinophil (cluster 5) and basophil (cluster 4) committed progenitors by the expression of lineage-specific surface markers (FIG. 2C) (Arinobu et al., 2005; Hettinger et al., 2013; Iwasaki et al., 2005). Neutrophils, however, lacked lineage-specific markers to allow for a proper characterisation of this dedicated progenitor.

Figures 2D, 2E, 2F:
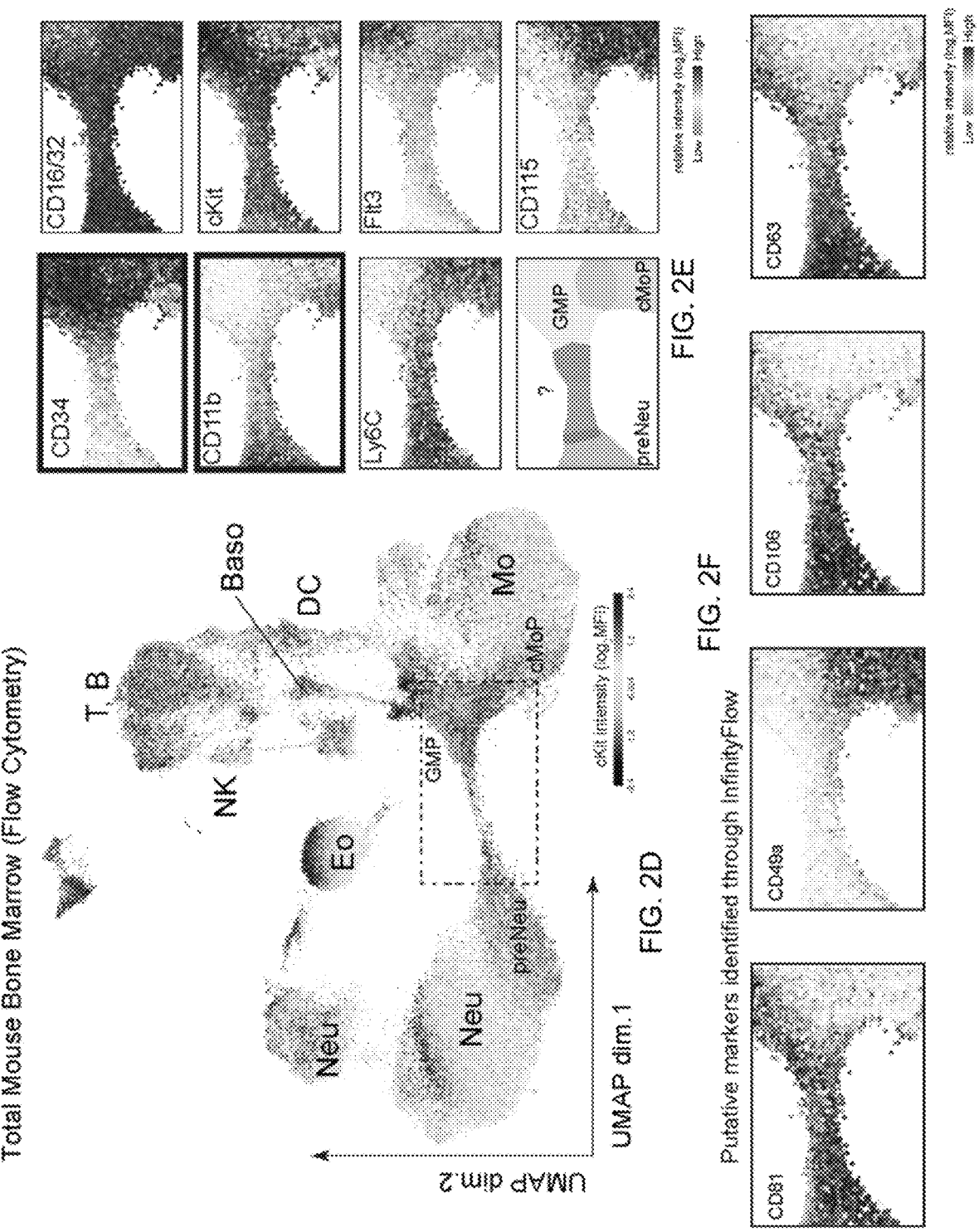
FIG. 2. InfinityFlow resolves GMP heterogeneity on a proteomic level. (A) InfinityFlow workflow. Whole mouse BM cells were stained with a backbone panel of lineage markers (see methods) to allow separation of each lineage for UMAP generation. Cells are then aliquoted into wells containing PE-conjugated antibodies. Each well information was then recorded by flow cytometry and processed using InfinityFlow pipeline. (B) t-SNE dimensional reduction analysis of 81 GMP-staining markers from InfinityFlow data. Phenograph clustering was performed and clusters are grouped to each myeloid lineage according to known lineage-restricted markers. (C) Analysis of the top discriminating markers for each cluster derived in (B). Black arrows (top) indicate known lineage-specific surface markers indicating GMP subset identity (right). Data is represented as a Z-score based on predicted Log₂ mean fluorescence intensity (MFI) from high (dark) to low (light). Importantly, each section of markers (demarcated by a space in between heatmaps) are the highly expressed markers that represent a certain progenitor subset of GMPs. (D) UMAP projection of total mouse BM cells, representing measured cKit expression levels from high (dark) to low (light) log ₂MFI. Neu=neutrophil, preNeu=pre-neutrophil, Eo=Eosinophil, T,B=T and B cells, NK=natural killer cells, Mo=monocytes, Baso=Basophil, DC=dendritic cell, cMoP=common monocyte progenitor, GMP=granulocyte-monocyte progenitor. (E) Zoomed-in expression level (Log₂MFI) plots of GMP area (dotted box in (D)), representing measured intensities of backbone markers. Expression continuity of CD34 and CD11b expression from GMP to preNeus is shown (highlighted boxes). Cell subset regions are denoted (bottom left), indicating bridge of progenitor cells. (F) Putative markers for GMP subset identification by InfinityFlow. Zoomed-in plots are represented as predicted intensities (Log₂MFI) from low (light) to high (dark) levels. (See also FIG. 9)
Figures 9A, 9B:
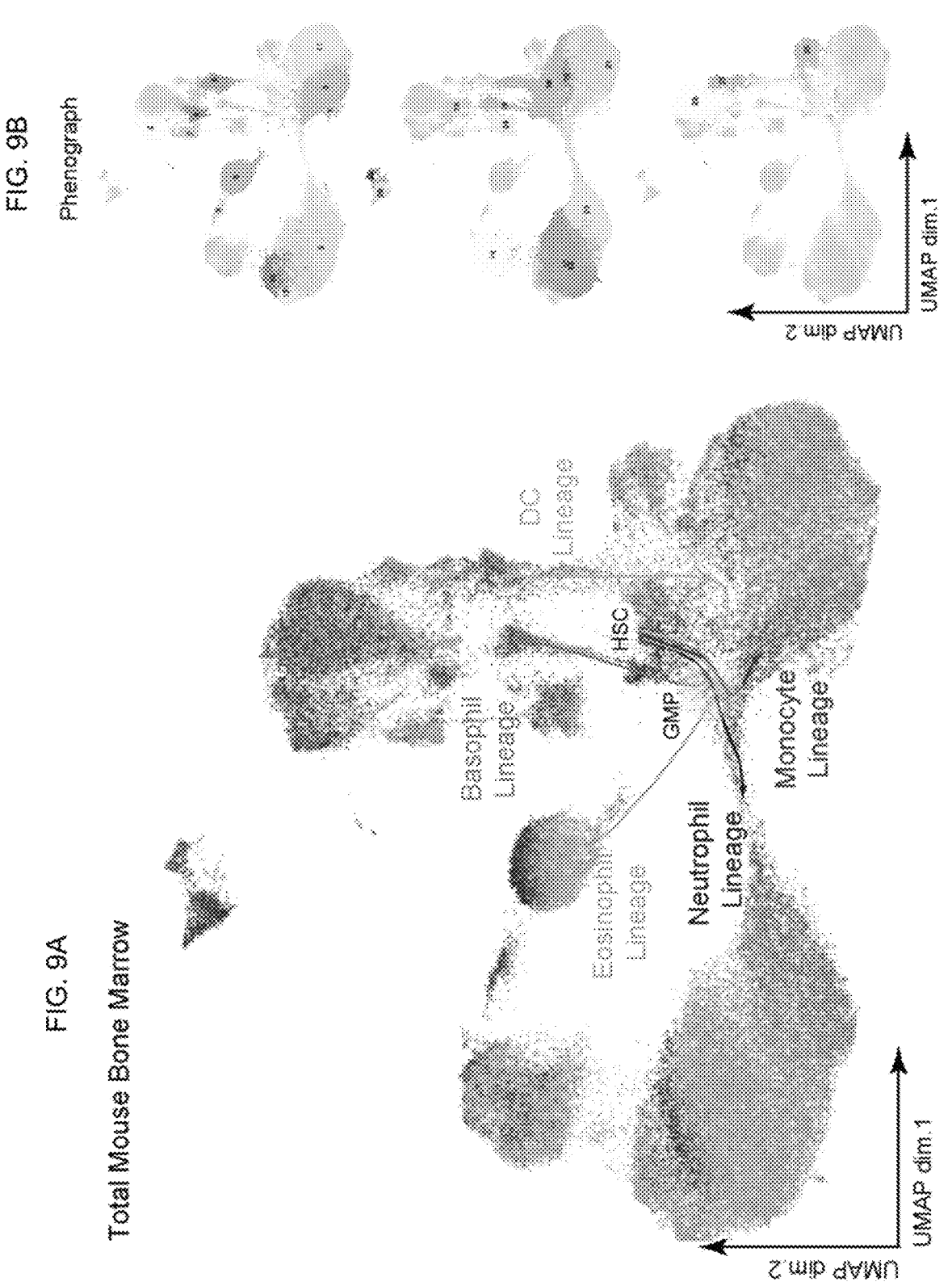
FIG. 9. UMAP, with InfinityFlow, reveals the expression continuity of the various BM lineages. (A) Developmental continuity of cell lineages of the various myeloid lineages expression. (B) Unbiased clustering with PhenoGraph of InfinityFlow dataset. Cluster identity is identified using typical lineage markers and is represented in Table 2. (C) UMAP plots of known lineage-restricted markers from low (light) to high (dark) expression levels, indicating each cell type.
Figure 9C:
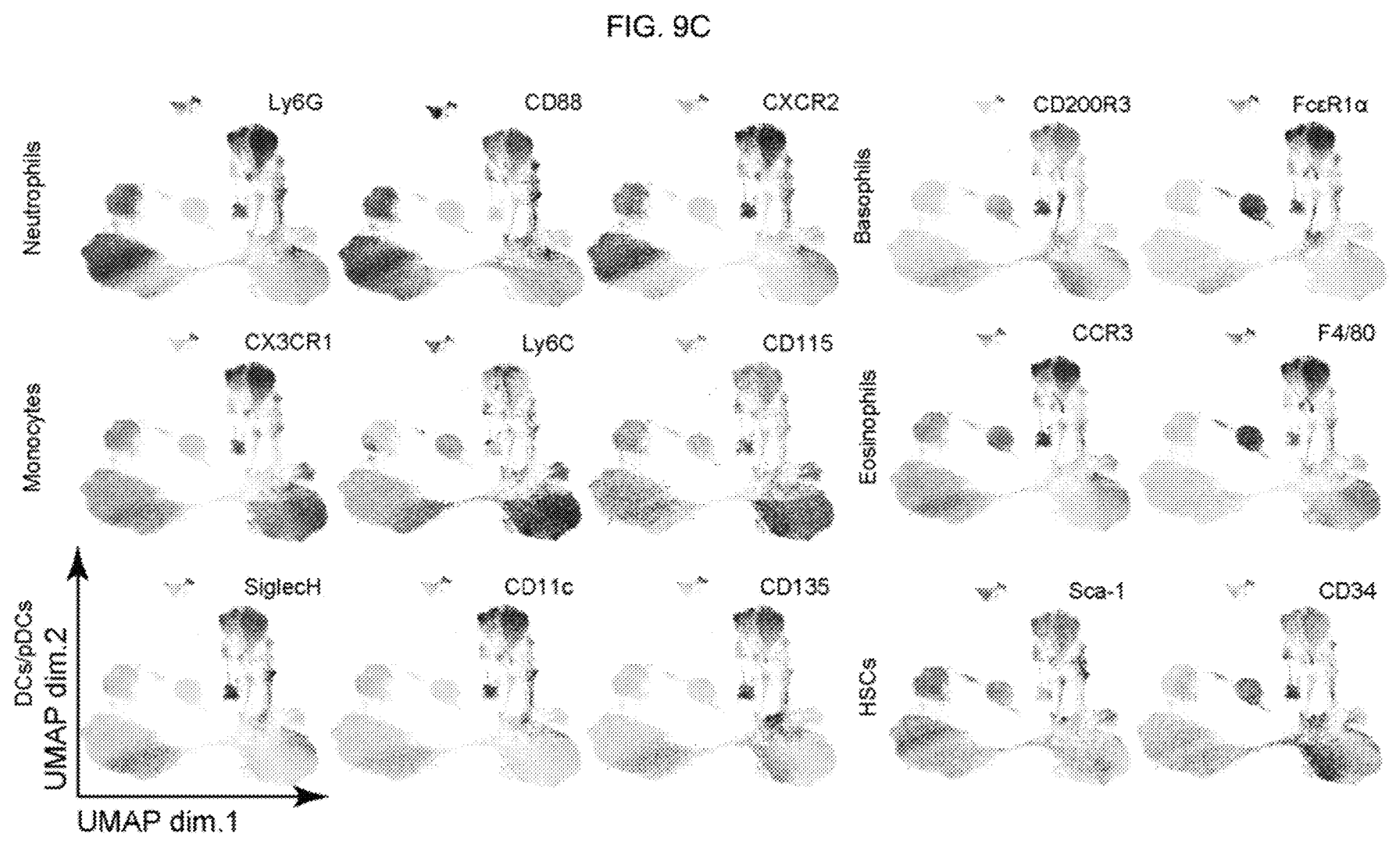

Therefore, to circumvent this challenge, UMAP analysis of the InfinityFlow dataset was performed to understand the developmental relationships between cell types in the BM based on their protein expression (Becht et al., 2018; McInnes et al., 2018). One major strength of UMAP is that it preserves the continuity of cell subsets, which allow for the identification of rare and/or transitional populations that would be masked in a t-SNE analysis (Becht et al., 2018). The UMAP analysis was expanded to total BM cells which discriminated the various cell lineages within the BM (FIG. 2D), and allowed for the observation of a clear developmental continuum of cells from early cKit⁺ progenitors to mature cKit⁻ cells of the basophil, eosinophil, monocyte and neutrophil lineages (FIGS. 2D and 9A). Utilising the markers from InfinityFlow, each cell type was identified and annotated through the co-localisation of each marker on the UMAP space (FIG. 9B, Table 1 and 9C). From the UMAP analysis, the inventors observed GMPs (cKit⁺Sca-1⁻CD34⁺ CD16/32$^{hi}$) with a gradual upregulation of Ly6C and a subsequent bifurcation into CD115⁻ and CD115⁺ cells, representing preNeus and cMoPs respectively (FIGS. 2D and 2E). While it is evident that cMoPs are a subset of the GMP, the branch connecting GMPs with preNeus revealed a progressive upregulation of CD11b and downregulation of CD34 expression along the developmental continuity from GMPs (FIG. 2E). This suggests that an early neutrophil progenitor exist within GMPs and extend along the developmental trajectory towards mature neutrophils. Closer inspection revealed several differentially expressed cell surface markers, including CD81, CD49a, CD106 and CD63, which highlight this branch point (FIG. 2F). These markers potentially serve as positive or exclusion markers to isolate and characterize the putative early neutrophil progenitor.

Identification of an Early Neutrophil Progenitor within the GMP

Figures 3A, 3B:
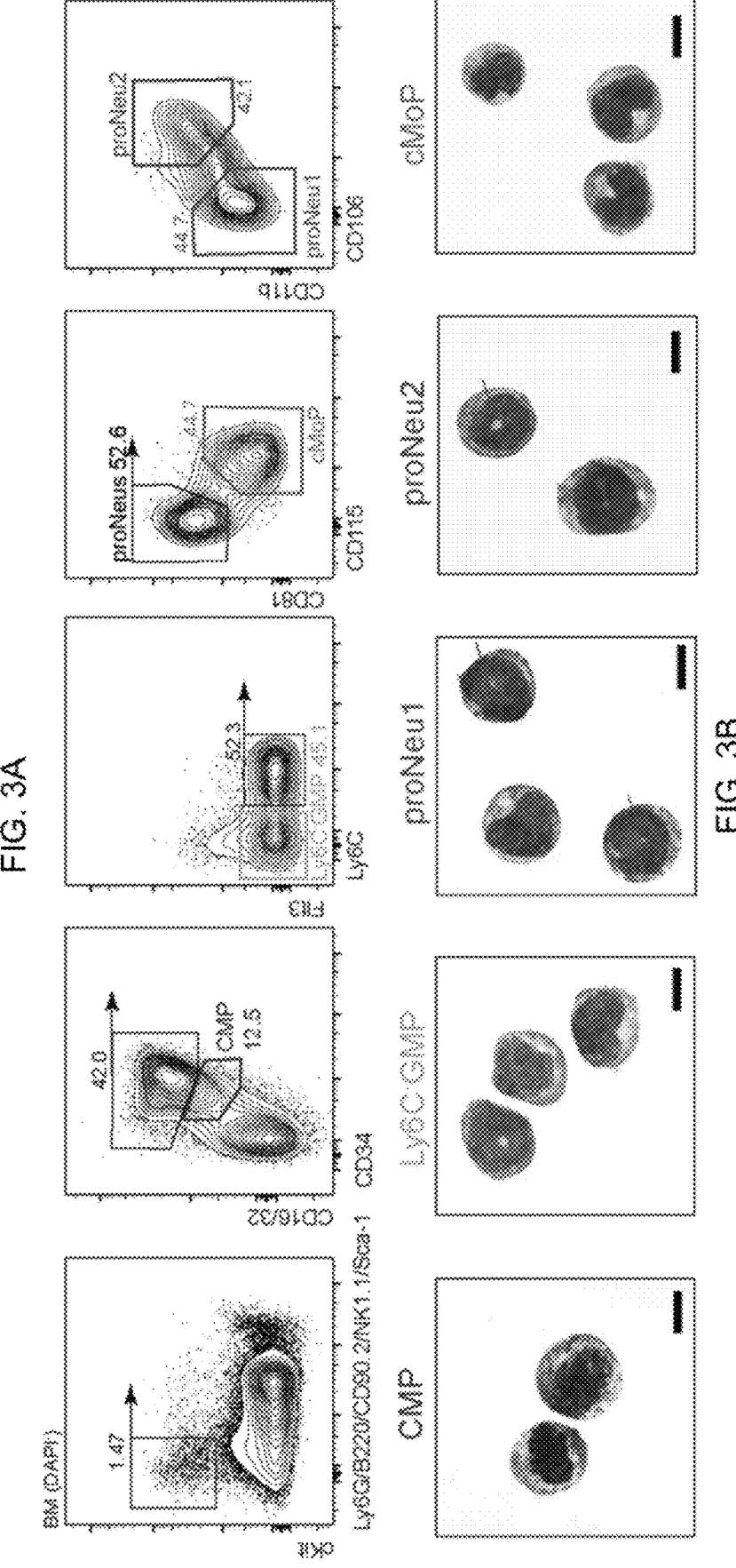
FIG. 3. Flow cytometric analysis of BM GMPs reveal a CD106⁻CD11bˡᵒ and a CD106⁺CD11bʰⁱ neutrophil progenitor population. (A) Gating and sorting strategy of mouse BM myeloid cell populations. CMP=common myeloid progenitor, cMoP=common monocyte progenitor. (B) Representative micrographs (n=3) of sorted populations indicated in (A). Scale bars=10 um. Grey arrows indicate hollowing. (C) PCA analysis using bulk RNA-seq data from sorted neutrophil and monocytic precursors according to gating strategy in (A). (D-E) Normalised expression comparing the various key monocyte (D) and neutrophil (E) transcription factors. Results are expressed as mean Log₂RPKM (n=3)±SD. (F) Heatmap of the top 5% most variable mouse transcription factors among indicated subsets. Known key factors are highlighted in bold. ProNeu-specific genes are highlighted as shown (black box). Data is represented as a Z-Score of expression (Log₂RPKM), calculated per gene from high (dark) to low (light) levels. Importantly, the critical differential genes of each lineage are indicated in bold on the right. (See also FIG. 10)
Figures 10A, 10B:
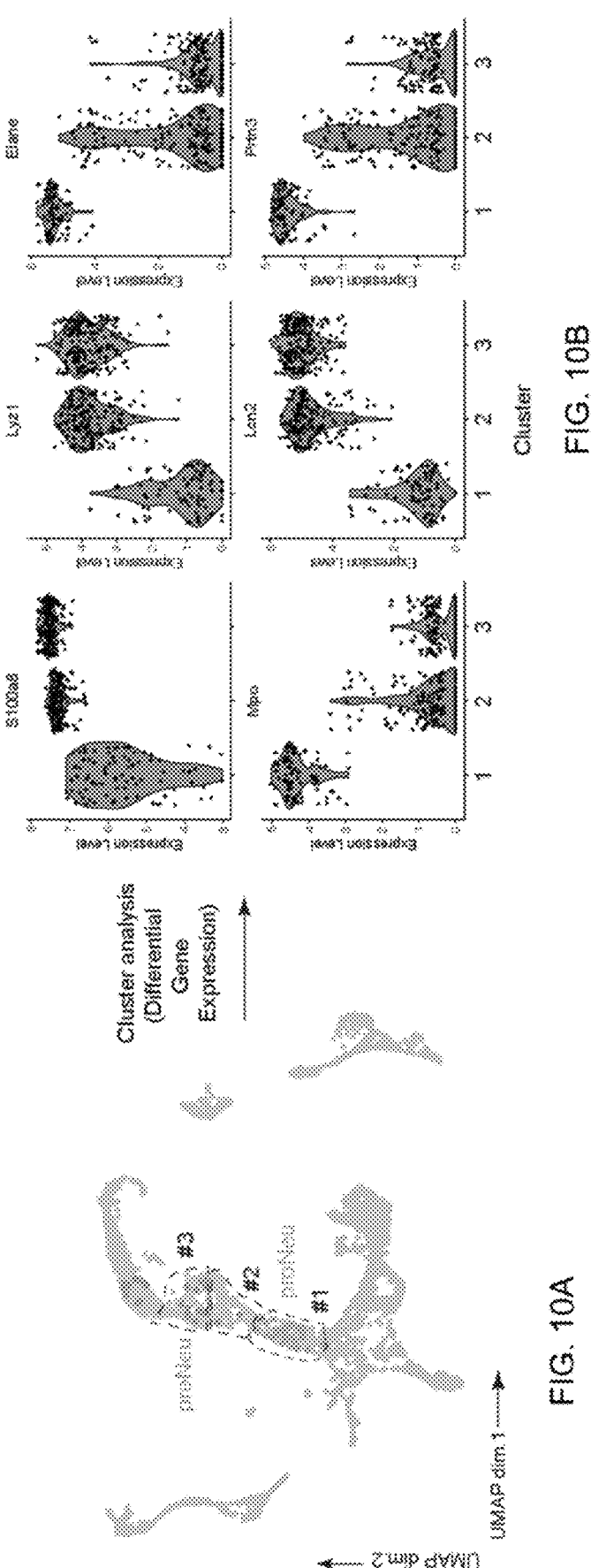
FIG. 10. proNeu2 are CD34$^{lo}$CD11b$^{hi}$ progenitors found outside the GMP phenotype. (A) Localisation of proNeu1 and preNeus in integrated dataset and (B) differential expression profile of clusters indicated. This expression data is only derived from the unintegrated *Tabula Muris* dataset. (C) GMP gating strategy without CD11b exclusion showing a CD11b$^{lo}$ and CD11b$^{hi}$ proNeus. (D) FACS plot of CD115 (CSF-1R) expression down-regulation with increased temperatures during tissue processing. Data is representative of at least three independent experiments. (E) Frequency and absolute counts of neutrophil progenitors in the mouse bone marrow. Data is expressed as mean±SD (n=5) and is representative of three experiments.

Using the newly identified markers CD81 and CD106, the inventors characterised two phenotypically distinct neutrophil progenitors (termed as proNeus). This included a CD34$^{hi}$CD106$^-$CD11b$^{lo}$ proNeu1 subset and a CD34$^{lo}$CD106$^+$CD11b$^{hi}$ proNeu2 subset (FIG. 3A). This observation is in line with the scRNA-seq data integration, which also unveiled a gap between the mapped neutrophil progenitor and preNeu cells (FIG. 10A), and cells within this gap expressed a continual progression of neutrophilic genes (FIG. 10B). This suggested that an intermediate subset exists within the developmental trajectory of neutrophil development and is absent from the currently defined GMP population. Indeed, proNeu2 escaped the GMP definition, as CD11b$^+$ cells are excluded from the GMPs (FIG. 10C). The inventors also utilized CD81 to exclude cMoPs as this marker allows for the circumvention of the technical concern of CD115 down-regulation during cell preparation (FIG. 10D). Similar to cMoPs, these neutrophil progenitors are rare and they account for 0.05-0.1% of total BM cells (FIG. 10E).

Morphological analysis revealed an initial hollowing of the nucleus in the proNeu1 stage, which increases in diameter in the proNeu2 stage (FIG. 3B) and subsequent maturation stages. Using the same sorting strategy for neutrophil progenitors in FIG. 3A, the inventors isolated these cells and performed bulk RNA-seq of myeloid progenitors, including Ly6C$^-$GMP, proNeu1, proNeu2, preNeu, cMoP and TpMo, to examine their differentiation and population inter-relationship. PCA analysis revealed a clear separation of the neutrophil and monocytic lineages (FIG. 3C). Deeper analysis of key neutrophilic and monocytic genes revealed similar expression levels of monocytic genes in Ly6C$^-$GMPs and proNeu1 (FIG. 3D). These genes were then upregulated in cMoPs, signifying their commitment to the monocyte fate. Interestingly, the expression level of key neutrophilic gens Gfi1 and Per3 in proNeu1 are also similar in Ly6C$^-$GMPs (FIG. 3E). The inventors further extended the knowledge of myeloid transcriptional regulation by selecting the top 20% variable transcription factors between these progenitor subsets and plotted them on a heatmap. The analysis featured groups of transcription factors solely expressed in cMoPs or Ly6C$^-$GMPs. Specifically, the data also suggests that Jag1 and Sox13 to be exclusive neutrophil lineage-committing factors (FIG. 3F). Jag1, in particular, was shown to be associated with G-CSF-mediated neutrophil differentiation.

Figure 4D:
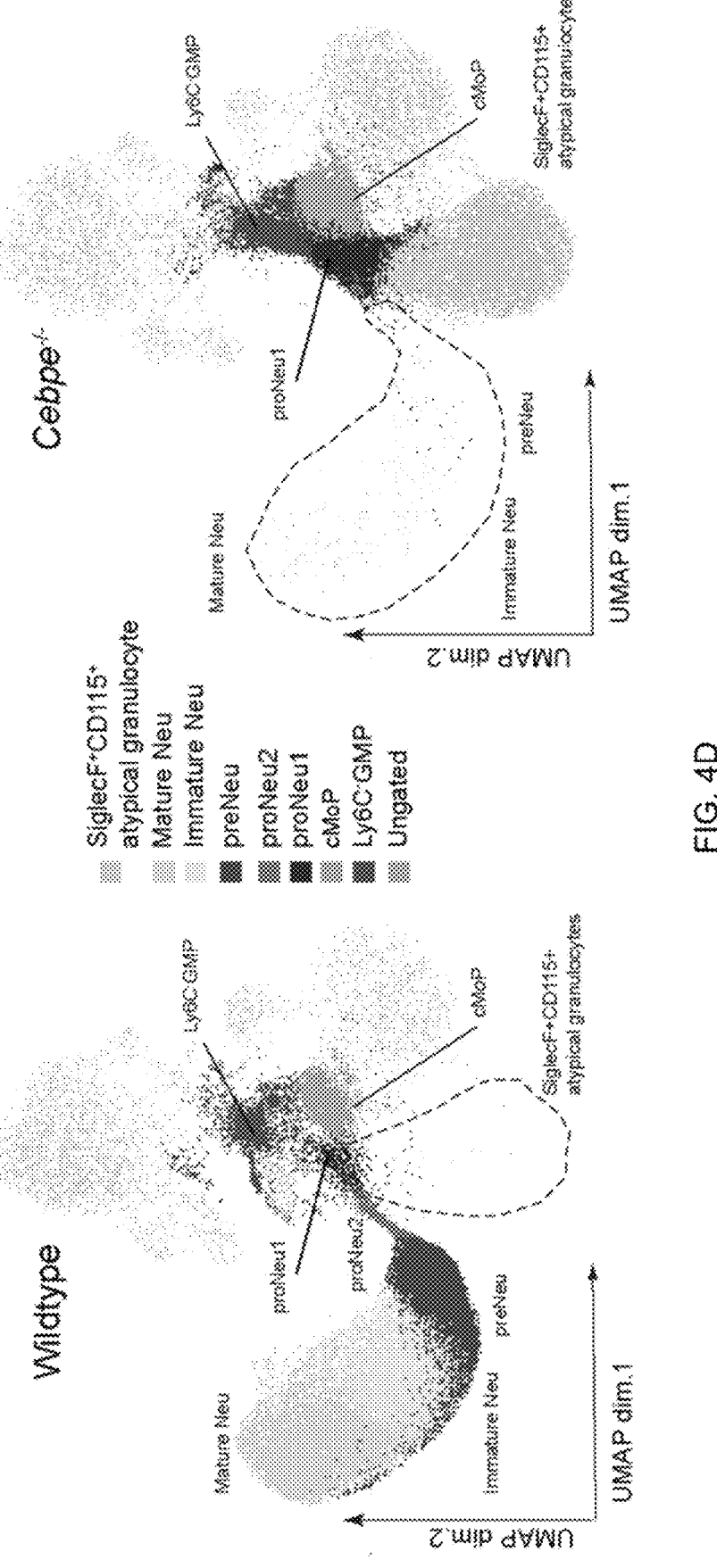
FIG. 4. Neutrophil development is dependent on two committed proNeu populations. (A) Representative FACS plot of gated proNeu1 and proNeu2 in WT and Cebpe⁻/⁻ mice. (B) Absolute counts of BM myeloid progenitors from WT and Cebpe⁻/⁻ mice. Data is expressed as mean±SD (n=5 per group) and is representative of two independent experiments=p<0.01, *=p<0.001, **=p<0.0001 (Student t-test). (C) BM chimeras were made by reconstituting irradiated mice with equal ratios of WT CD45.1⁺ and Cebpe⁻/⁻ CD45.2⁺ cells. The percentage contributions of various hematopoietic cells by WT CD45.1⁺ or Cebpe⁻/⁻ CD45.2⁺ cells are expressed as mean±SD (n=5) and are representative of two independent experiments. **=p<0.0001 (Student t-test). (D) UMAP analysis of total live BM cells from WT and Cepbe⁻/⁻ mice. Cells were manually gated and overlaid onto the UMAP plot, representing the localization of each subset on the UMAP space. (E) In vitro stimulation of sorted populations with CSF-1, quantified for F4/80⁺ macrophages at day 3 and 5. Results are represented as mean (n=4-5 per subset)±SD and are representative of three independent experiments. (F) (top) Experimental setup of (bottom) Intra-BM transfer of sorted uGFP⁺proNeu1, CD45.2⁺ proNeu2 and ROSAᵐᵀ/ᵐᴳ RFP⁺ preNeus into wildtype CD45.1⁺ recipients. Black dots represent transferred subset after 3 days. Data are representative of five recipient mice from two independent experiments. Mo=monocytes, Eo=eosinophils. (See also FIG. 11)
Figure 11A:
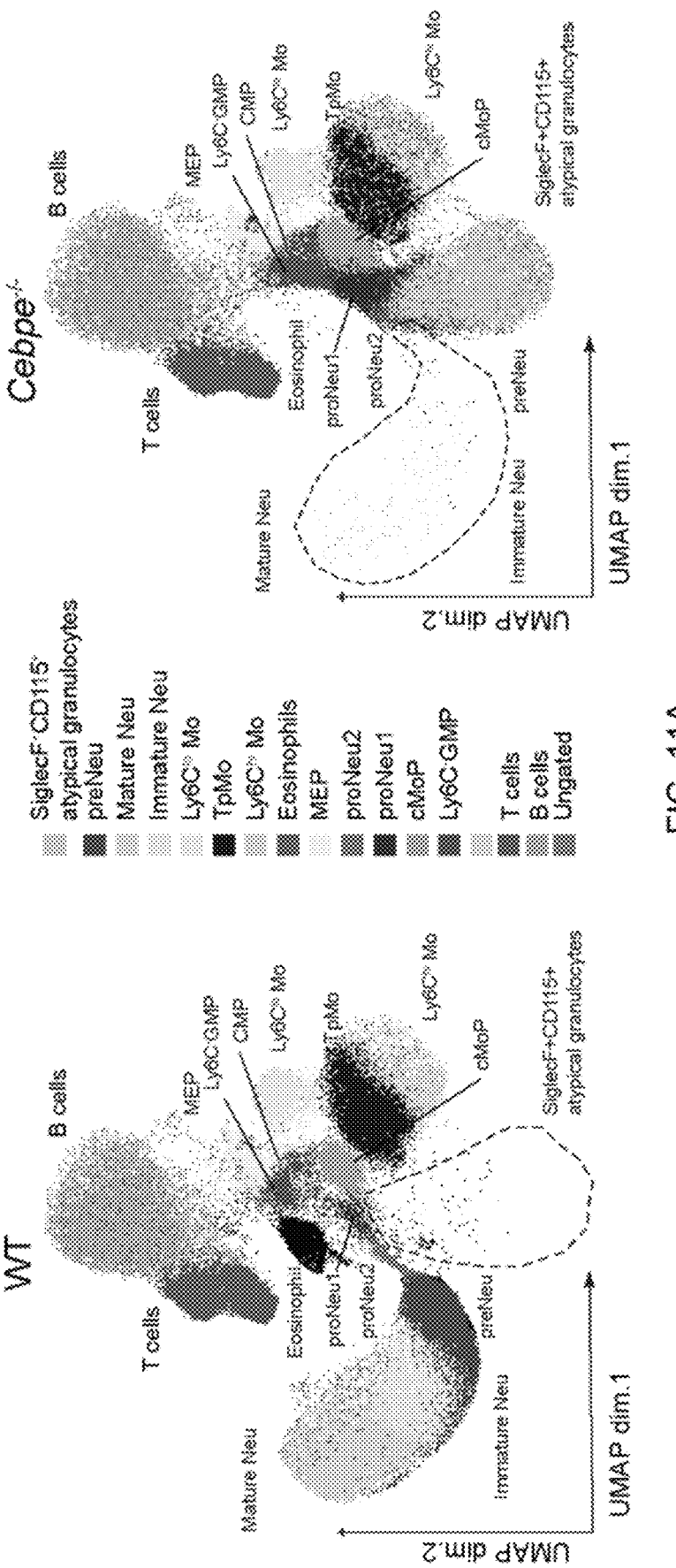
FIG. 11. Neutrophil development is dependent on two committed proNeu populations. (A) UMAP plot of total BM from WT (left) and Cebpe$^{-/-}$ (right) mice indicating the various cell lineages. Cells were manually gated and overlaid onto the UMAP plot to view each population's location and relationship with their adjacent cell types. (B) (top) UMAP expression plots of CD81 and CD106, indicating the localisation of proNeu2. (bottom) UMAP expression heatmap plots of CD115 and SiglecF indicating the atypical granulocyte population in Cebpe$^{-/-}$ BM cells. (C) In vitro stimulation of sorted populations with M-CSF, quantified for Ly6G$^+$ neutrophils at day 3 and 5. Results are represented as mean (n=3 per subset)±SD and are representative of three independent experiments. (D) Intra-BM transfer of sorted uGFP$^+$ Ly6C$^-$GMP, proNeu1 or proNeu2 into wildtype recipients. Results represent progeny of transferred proNeu1 subset after 1 day of transfer. (E) Composition of the progeny of each transferred subset was analyzed and represented in a bar graph. Data is expressed as mean±SD (n=4 per group) from two independent experiments.
Figure 11B:
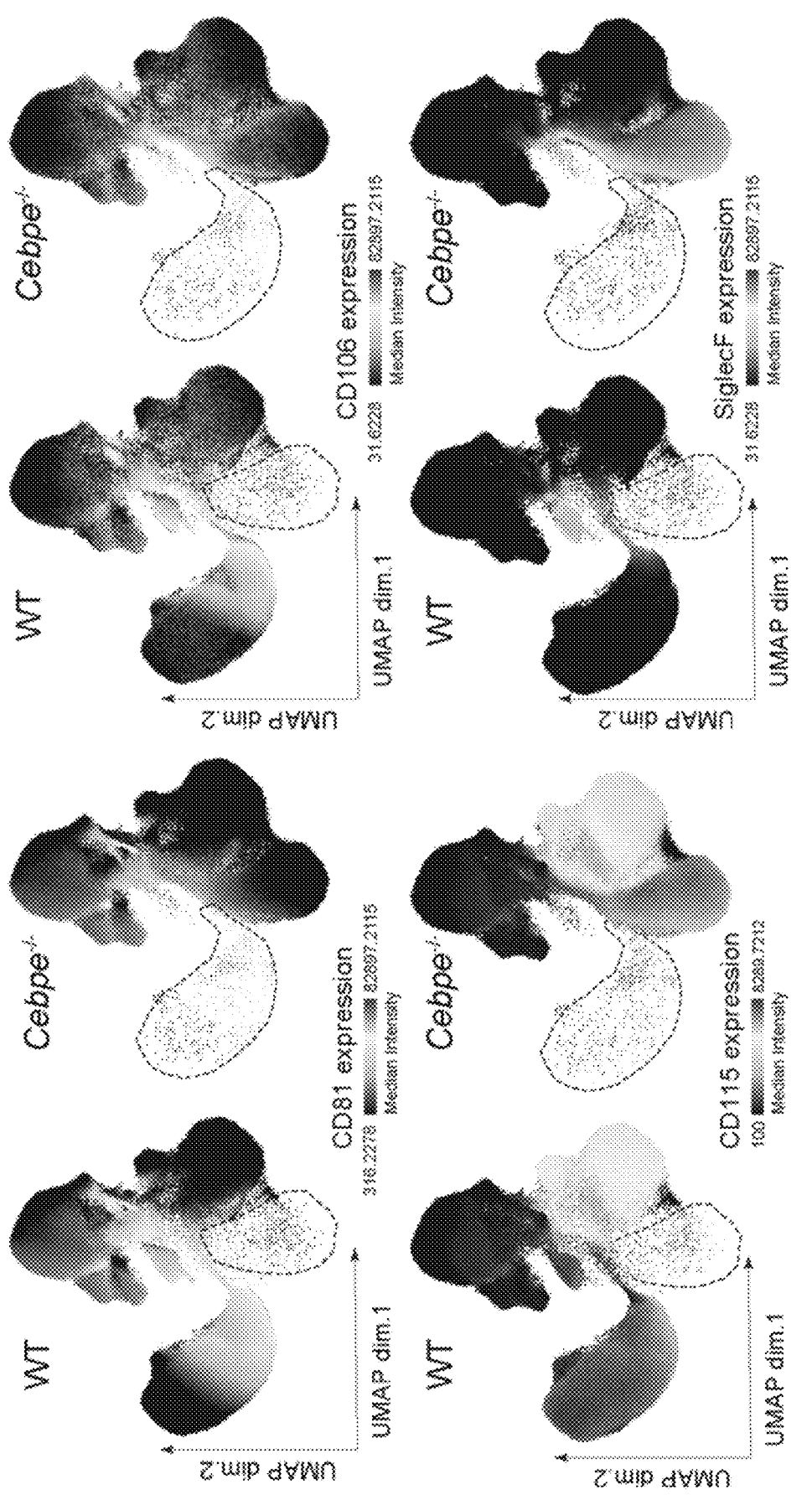

It has been shown that a deficiency in C/EBPs leads to a disruption in neutrophil development. Here, the RNA-Seq analysis showed an upregulation of Cebpe from proNeu1 to proNeu2, suggesting that C/EBPs could be critical for the development of early neutrophil progenitors (FIG. 3E). To test this, the BM of wildtype (WT) and Cebpe$^{-/-}$ mice was analysed. The analysis revealed that C/EBP$_\varepsilon$ is critical for proNeu2 development (FIG. 4A). Together with the loss of proNeu2, an accumulation of cMoPs was also observed, suggesting a block in neutrophil development resulted in a skewed differentiation towards the monocyte fate (FIG. 4B). These observations were further confirmed by generating BM chimeras with CD45.1$^+$ WT and CD45.2$^+$ Cebepe$^{-/-}$ BM cells in a 50:50 ratio. Analysis of these mice BM showed that proNeu2, and downstream populations, were mostly generated from WT CD45.1$^+$ cells (FIG. 4C). This suggests the importance of proNeu2 as a bridging point between proNeu1 and preNeu. UMAP further illustrates this, showing that proNeu2 acts as a bridge between proNeu1 and preNeu development, and the absence of these cells leads to an aberrant differentiation pathway generating atypical granulocytes that are SiglecF$^+$CD115$^+$ (FIGS. 4D and 11B).

Figures 4E, 4F:
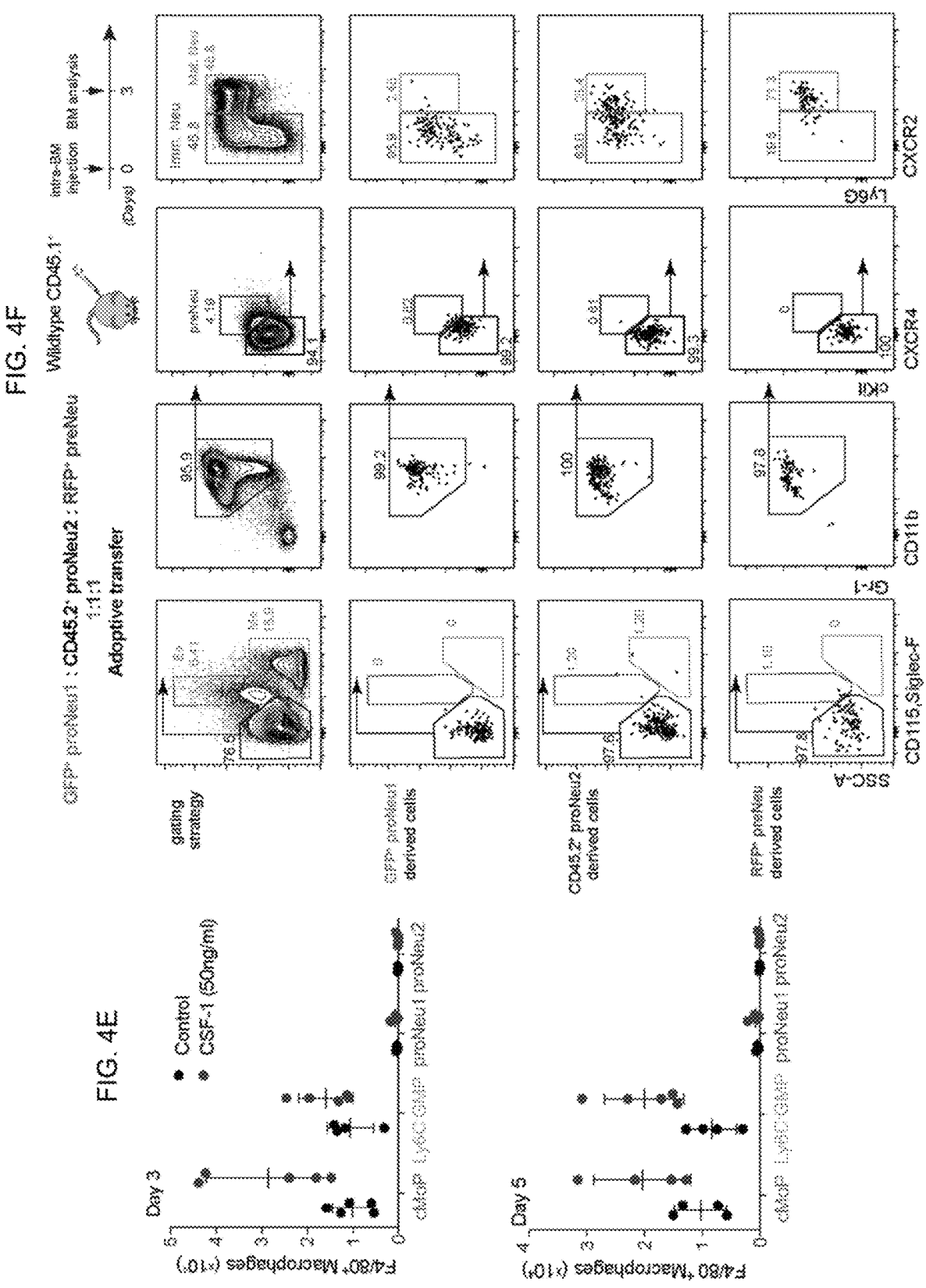
Figures 11C, 11D, 11E:
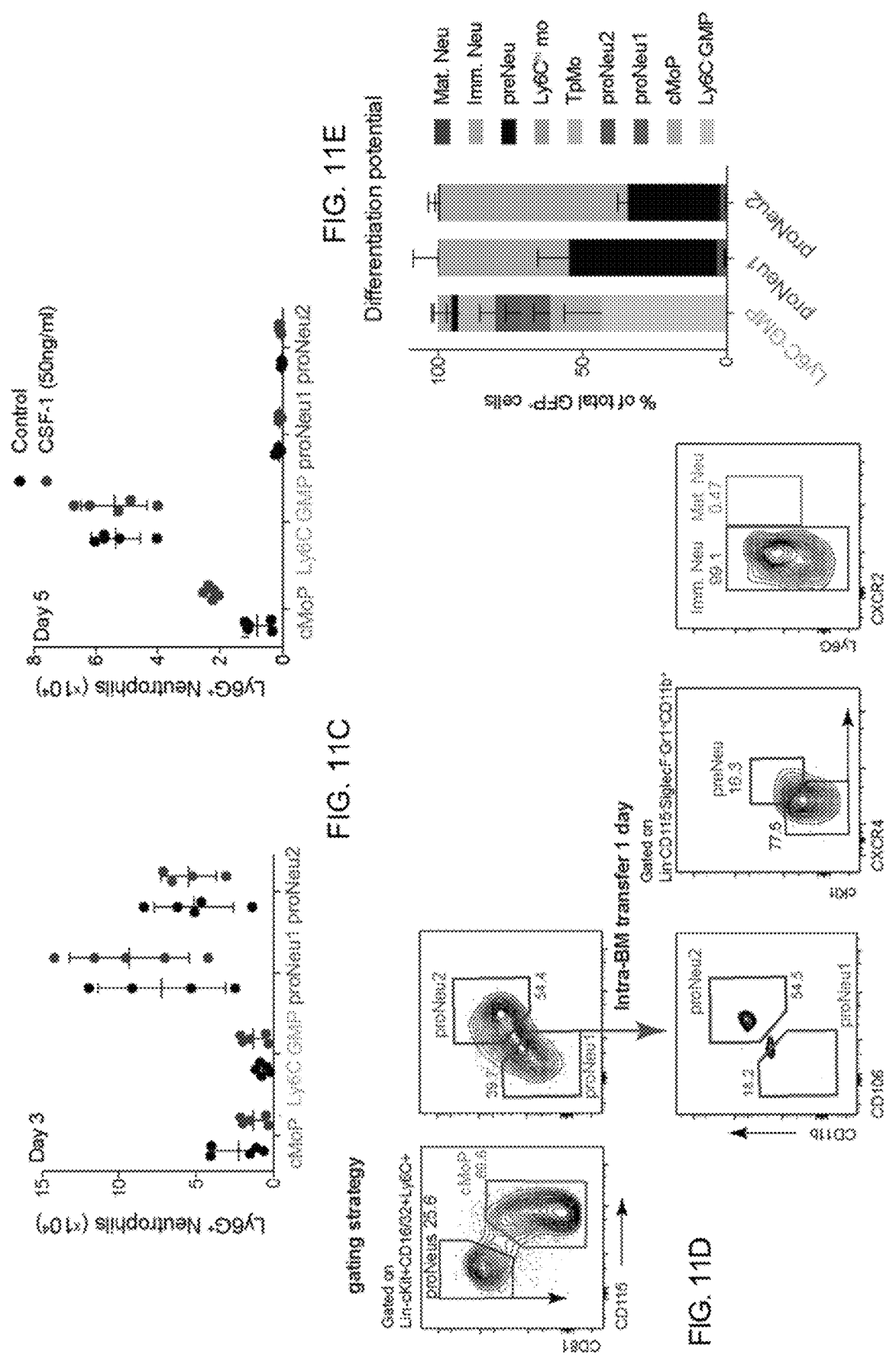

Since proNeu1 s possessed both monocytic and neutrophilic transcription factors (FIGS. 3D and 3E), it was hypothesized that proNeu1s may not be fully specified to neutrophil lineage and could give rise to monocytes depending on lineage cues. To assess the commitment fate of proNeus, the various sorted progenitor populations were cultured with CSF-1, which is known to skew differentiation towards the monocytic lineage. The results showed that both proNeu1 and proNeu2 gave rise to Ly6G$^+$ neutrophils and not macrophages with CSF-1 (FIG. 11C), while both cMoPs and Ly6C$^-$GMPs mostly gave rise to macrophages by day 5 of culture with CSF-1 (FIG. 4E). To further affirm the neutrophil commitment capacity of proNeu1 and proNeu2, the inventors adoptively transferred sorted Ly6C$^-$GMPs, proNeu1s, proNeu2s and tracked their differentiation potential. While Ly6C$^-$GMPs gave rise to both proNeu1s and cMoPs after 1 day, proNeu1 gave rise to proNeu2s and subsequent neutrophil subsets (FIG. 11D). ProNeu2s similarly only specifically gave rise to preNeus and immature Neus (FIG. 11E).

As these transfer experiments were performed in separate WT recipients, the inventors wanted to assess the differentiation potential of proNeus within the same microenvironment. To do this, the inventors co-transferred sorted and labelled proNeus (1 &2) and preNeus into WT recipients and tracked their development after three days. The results showed that both proNeu1 s and proNeu2s could only give rise to neutrophils with negligible monocytic differentiation potential (FIG. 4F). Moreover, from proNeu1s to preNeus, a step-wise differentiation progression with a sequential upregulation of Ly6G and CXCR2 was observed. Together, the data highlights a programmed neutrophil lineage commitment that exists within the GMP and this begins with proNeu1 s, which exclusively gives rise to downstream neutrophil subsets through a C/EBP$_\varepsilon$-dependent proNeu2 development.

ProNeu1 and proNeu2 are Functionally Distinct Early Neutrophil Progenitor Populations.

Figures 5A, 5B, 5C, 5D:
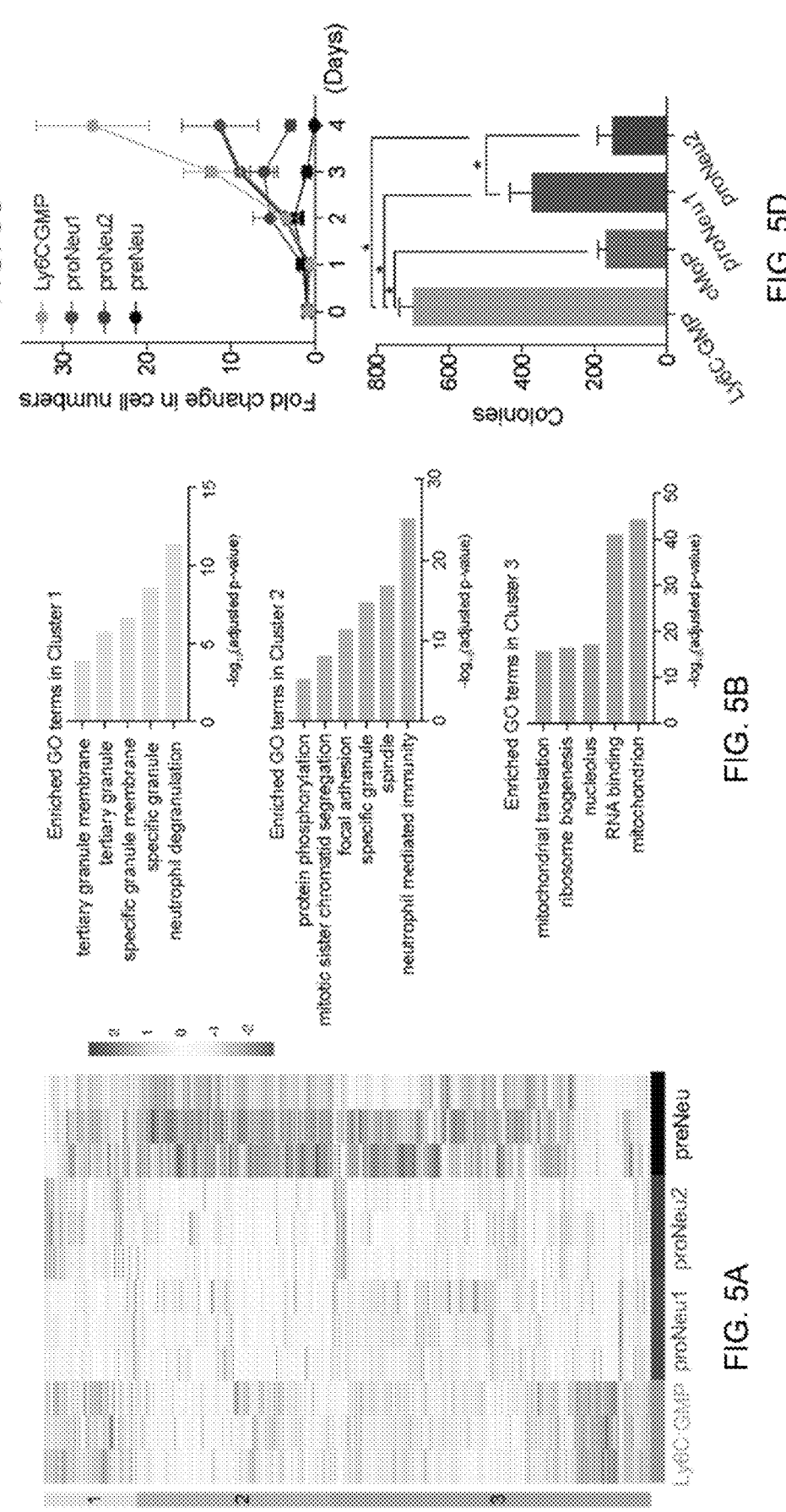
FIG. 5. proNeu1 and proNeu2 are functionally distinct progenitors. (A) Heatmap of total ANOVA-corrected variable genes from bulk RNA-Seq transcripts of sorted precursor subsets. Data is represented as a Z-Score, from low (light) to high (dark) expression. Gene clusters (1 to 3) were defined according to hierarchical clustering and exported for (B) gene ontology (GO) enrichment analysis showing the top GO terms (biological process, cellular component and molecular function) using EnrichR. (C) In vitro proliferation assay of sorted populations over 4 days in culture. Results are expressed as mean fold change (n=3 per subset)±SD and are representative of at least three independent experiments. (D) In vitro colony forming potential of sorted populations. Results are expressed as mean (n=3 per subset)±SD and are representative of at least three independent experiments. *=p<0.05 (Student t-test). (E) Percentage of cells in the proliferating S-G2-M phase of the cell cycle denoted by Fucci-S/G2/M positive cells. Data are representative of two independent experiments. (F) GO enrichment and biofunction enrichment analysis comparison of proNeu1 and proNeu2. Biofunction enrichment analysis was performed with Ingenuity Pathway Analysis (IPA) tool. (G) Volcano plot comparing BM proNeu1 and proNeu2. Selected DEGs corresponding to proNeu1 and proNeu2 function are labelled on the plot. (H) Experimental set-up of mid-grade cecal ligation and puncture (CLP) sepsis kinetics and analysis timepoints. (I) Absolute counts of total bone marrow GMPs (left) and GMP subsets based on Ly6C expression (right) at indicated timepoints. (J) FACS analysis of BM Ly6C$^+$GMP composition at the indicated timepoints. *=p<0.05 (One-way ANOVA). (K) Absolute counts of total BM GMPs (left) and Ly6C$^+$GMP subsets (right) at indicated timepoints. (H-K) Data are expressed as mean (n=4-9 per timepoint)±SD and are representative of two independent experiments. *=p<0.05 (One-way ANOVA). (See also FIG. 12)
Figure 12A:
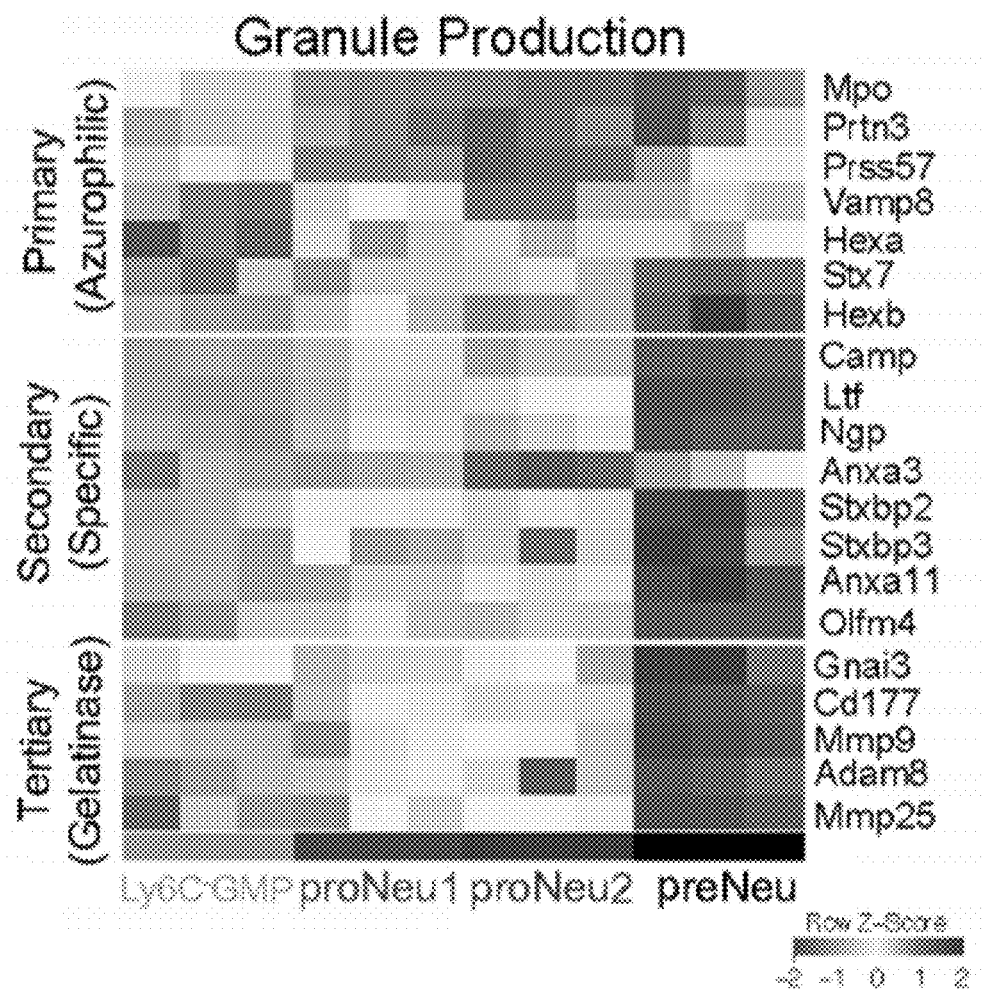
FIG. 12. Characterisation of two functionally distinct proNeu subsets. (A) Genes encoding for granules and (B) ATP metabolic processes among neutrophil precursor subsets are shown as heatmaps, expressed as normalised values (Z-score) from low (light) to high (dark) levels. Importantly, development from proNeu1 to proNeu2 to preNeu is associated with an increase in ATP metabolic processes. (C) Representative colonies of progenitor subsets at the indicated timepoints. Scale bars=50 μm. (D) mRNA and protein expression of various markers among cMoP and neutrophil precursor subsets are shown as heatmaps, expressed as normalised values (Z-score of log$_2$RPKM (for mRNA expression) or MFI (for protein expression)) from low (light) to high (dark) levels. (E) Representative FACS plots of BM Ly6C$^+$GMPs during mid-grade sepsis at the indicated time points. (F) Representative FACS plot showing Csf1r-GFP expression of BM Ly6C$^+$GMPs during sepsis. (G) Subset percentages within Ly6C$^+$GMPs at the indicated timepoints after sepsis onset. Data are expressed as mean (n=3 per timepoint)±SD and are representative of two independent experiments. *=p<0.05 (Student t-test). (H) Frequency of Csf1r-GFP cells three days after mid-grade sepsis onset. Data are expressed as mean (n=3)+SD and are representative of two independent experiments. *=p<0.05 (Student t-test).
Figure 12B:
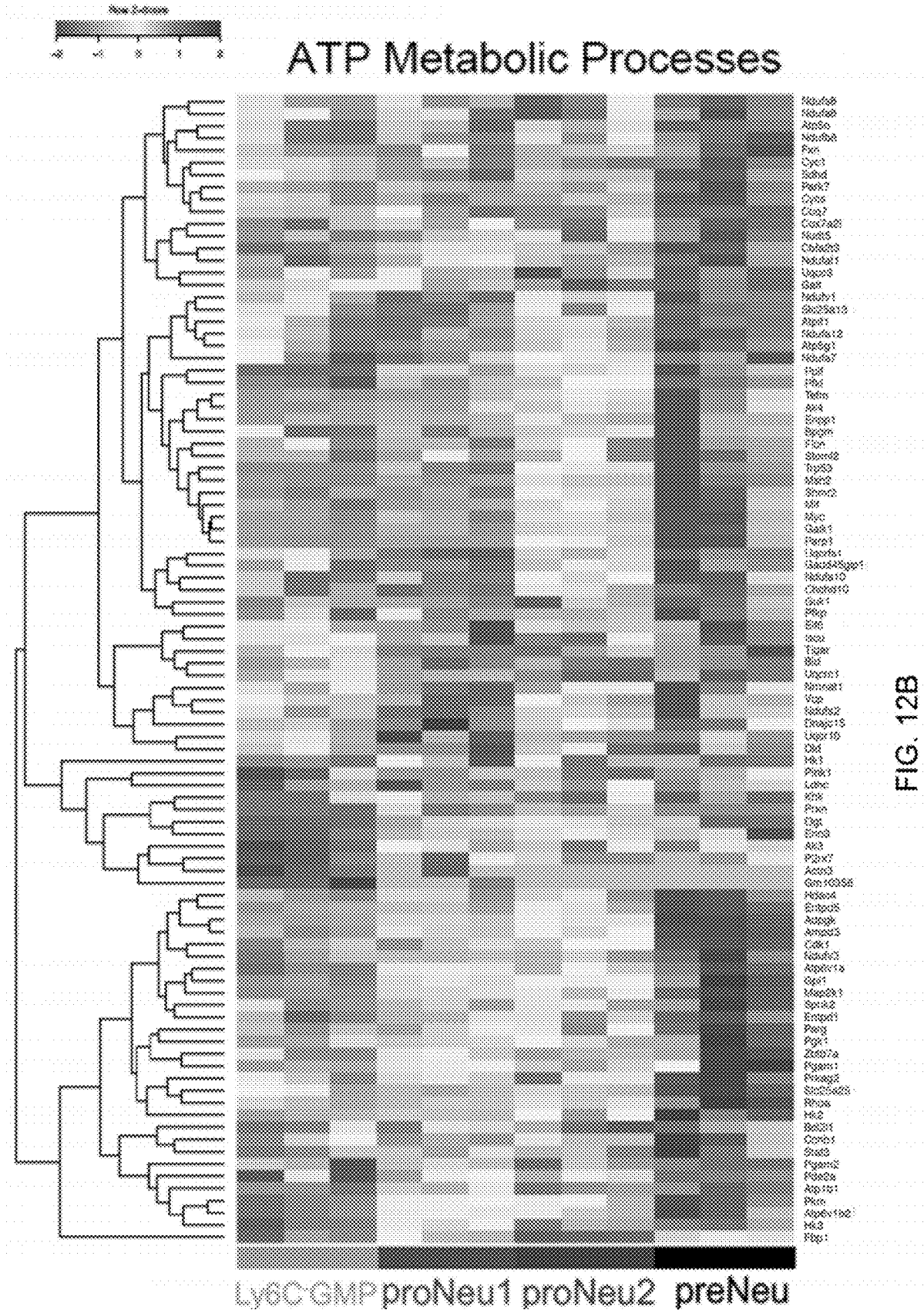

To dissect the functional heterogeneity and progression of these neutrophil progenitors, the transcriptomic signatures from Ly6C$^-$GMPs to preNeus was analyzed. By plotting the top variable genes among each subset, the inventors derived three distinct clusters of genes differentially regulated between each stage of neutrophil development (FIG. 5A). From the heatmap, the inventors observed a sequential increase in granule production (Cluster 1) (FIGS. 5B and 12A) and a concomitant loss of mitochondrial and ribosomal genes (Cluster 3), in line with their progressive acquisition of neutrophil functionality (FIG. 5B and FIG. 12B).

Figures 5E, 5F, 5G:
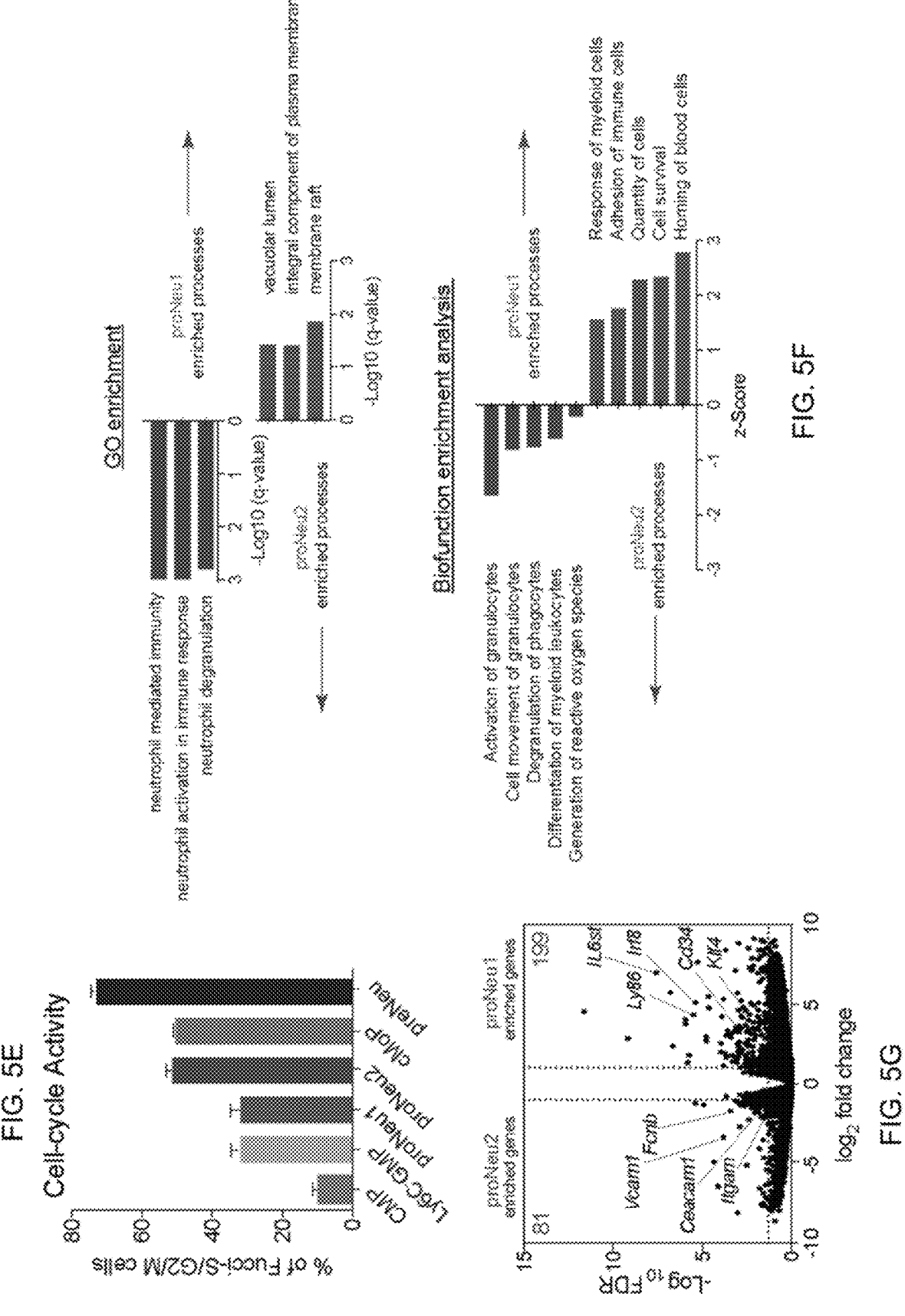
Figures 12C, 12D:
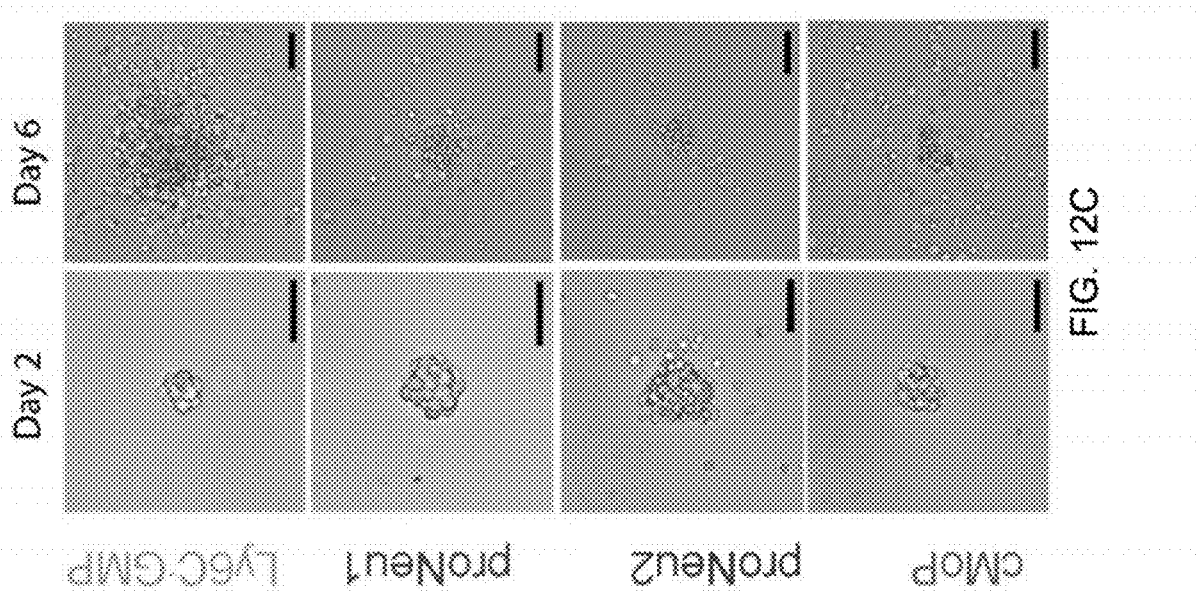

As CD34 is a known marker for hematopoietic progenitors, it was wondered if progenitor properties are lost in a CD34$^{lo}$ proNeu2 subset. To test this, the proliferative potential of proNeu1 and proNeu2 was evaluated. In vitro cultures showed that, unlike the minimal colony-forming activity of preNeus, both proNeu1 and proNeu2 possessed high proliferative potential (FIG. 5C). Notably, a lower proliferative capacity in proNeu2 compared to proNeu1 was observed, which is further supported by the fewer colonies generated in vitro (FIGS. 5D and 12C). ProNeu1, distinct from proNeu2, possessed enhanced colony forming potential with a cell cycle activity similar to uncommitted Ly6C⁻GMPs, as shown by the Fucci cell-cycle transgenic reporter line (Sakaue-Sawano et al., 2008) (FIG. 5E). This suggests that proNeu1 possess higher self-renewing properties, which is then exchanged for effector functions in proNeu2. Furthermore, transcriptomic pathway analyses support this decrease in progenitor function of proNeu2, showing an exclusive enrichment in neutrophil effector functions, while proNeu1 are enriched in cellular components and cell survival (FIG. 5F). Collectively, the data shows that proNeu1 and proNeu2 are two distinct progenitor subsets with unique function pertaining to the development of neutrophils. Similar to their surface marker expression, Cd34 was found to be upregulated in proNeu1 while genes encoding CD106 (Vcam1) and CD11b (Itgam) were significantly enriched in proNeu2 (FIG. 5G). These results hence confirm the scRNA-seq and UMAP (FIG. 10A) analysis that proNeu2 is downstream in the neutrophil lineage from proNeu1.

To understand how these progenitors might play differential roles in inflammatory states, the inventors utilized a model of sepsis and tracked the BM progenitor composition at various timepoints (FIG. 5H). Through the course of infection, the inventors observed an expansion of Ly6C⁺ GMPs but minimal changes in Ly6C-GMP numbers (FIG. 5I). Further analysis of Ly6C⁺GMPs revealed a skewed differentiation effect towards the neutrophil lineage on day 3, with a specific increase in proNeu1 frequency at the expense of cMoP numbers (FIG. 5J). Unlike proNeu1, proNeu2 remained largely unchanged during the course of infection, suggesting differential roles for each progenitor during sepsis. The inventors also showed that this skewing effect can be observed from day 1 of sepsis onset (FIGS. 12E and 12G), and confirmed that CD115 was not down-regulated during inflammation using a Csf1r-GFP MaFIA transgenic mouse (FIGS. 12F and 12H). The shift in myeloid progenitor potential then returns to physiological frequencies by day 9, together with a specific expansion of cMoPs (FIG. 5K), suggesting their importance during the resolution phase of sepsis. Importantly, this critical information would have been lost if total GMPs were analysed, exemplifying the need for the analysis of specific progenitor subsets to understand the dynamics of progenitor function in inflammatory conditions.

G-CSF-Mediated BM Skewing of Myeloid Progenitors can Modulate Neutrophil Expansion The ability of BM progenitors to replenish the circulating pool of immune cells is a critical step in infections and diseases when a large demand of mature cells is needed. In particular, neutralization of invading pathogens and microbial insults requires emergency granulopoiesis, which is a mechanism whereby the immune system adapts to produce and mobilize neutrophils in a prompt and efficient manner.

Figures 6A, 6B, 6C, 6D, 6E:
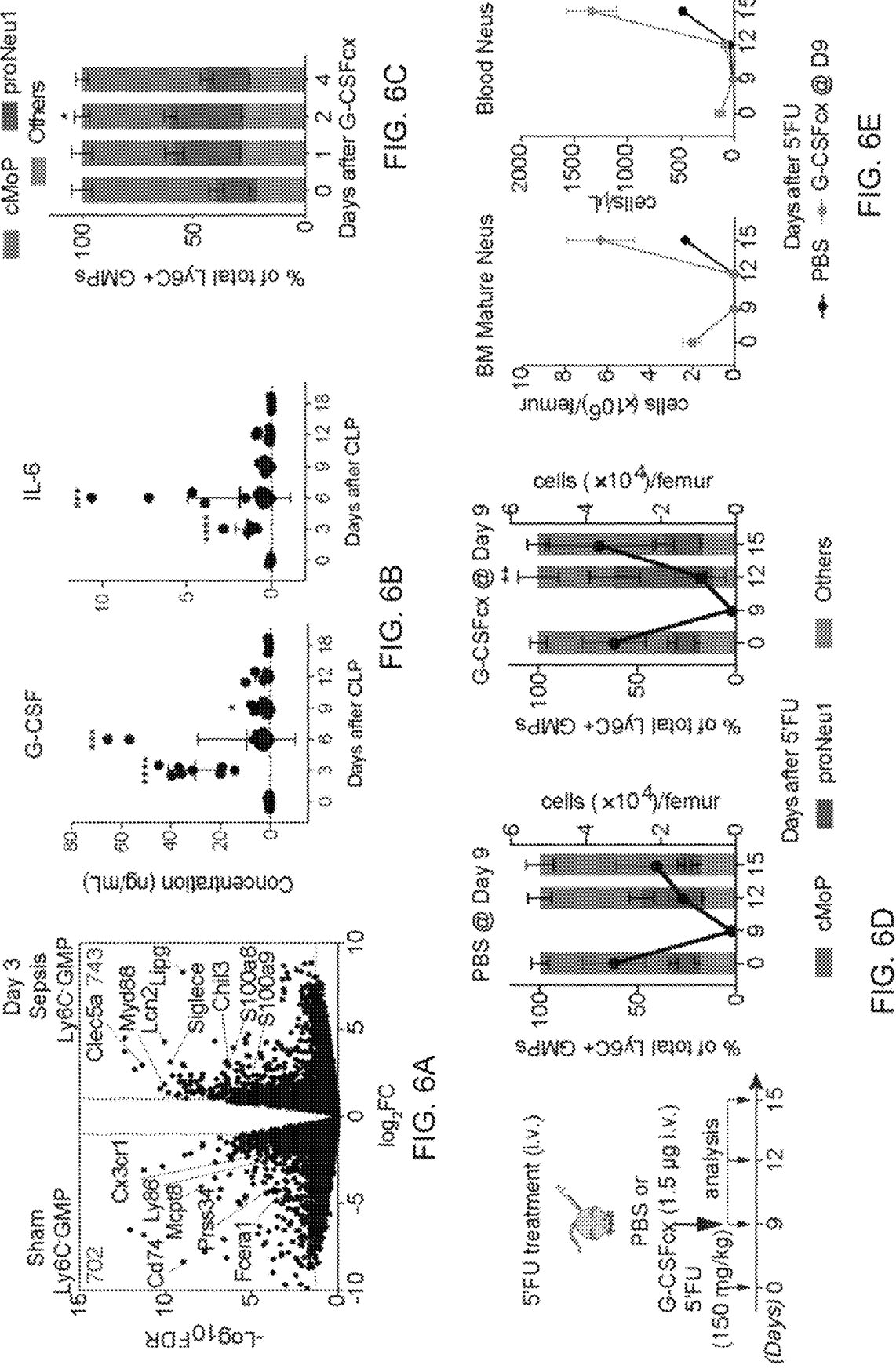
FIG. 6. Skewed specification of GMPs towards neutrophil commitment is directed by G-CSF during emergency granulopoiesis. (A) Transcriptomic comparison between day 3 septic BM Ly6C$^-$GMPs against WT sham control BM Ly6C-GMPs. Selected genes represent various genes critical for the various myeloid lineages. (B) Cytokine analysis of serum from mid-grade septic mice at various timepoints. Data is expressed as mean (n=4-9 per timepoint)±SD from two independent experiments. *=p<0.05, *=p<0.001, **=p<0.0001 (One-way ANOVA). (C) Analysis of Ly6C$^+$ GMP subsets after G-CSF complex (G-CSFcx) administration. Data are expressed as mean (n=5 per timepoint)±SD and are representative of two independent experiments. *=p<0.05 (One-way ANOVA) (D) Myeloablative treatment experimental plan (left) and (right) analysis of Ly6C$^+$GMP composition with or without G-CSFcx intervention at day 9 of 5'FU treatment. Lines represent absolute counts of total Ly6C$^+$GMPs at the indicated timepoints. (E) Absolute numbers of bone marrow mature neutrophils and blood neutrophils at the indicated timepoints. (D-E) Data are expressed as mean (n=5 per timepoint)±SD and are representative of two independent experiments. **=p<0.01 (One-way ANOVA). (See also FIG. 13)

To determine if the increased proNeu1 frequencies during sepsis are pre-determined in early progenitors, transcriptomic analysis of Ly6C⁻GMPs was performed at day 3 of sepsis onset, revealing a down-regulation of multiple lineage associated genes, such as Mcpt8, Ly86, Prss34 and Fcera1. An up-regulation of granule protein genes such as S100a9, S100a8, Chil3 and Lcn2 was also observed (FIG. 6A). These results not only verify the importance of the proNeu findings, but further confirms the skewing effect of proNeu1 differentiation. Interestingly, at day 6 where variability of BM skewing is at its peak, the inventors observed a correlation of spleen size with the recovery of the skewed progenitor compartment (FIG. 13A), indicating a possible role of extra-medullary haematopoiesis in the resolution of sepsis.

Figures 13A, 13B:
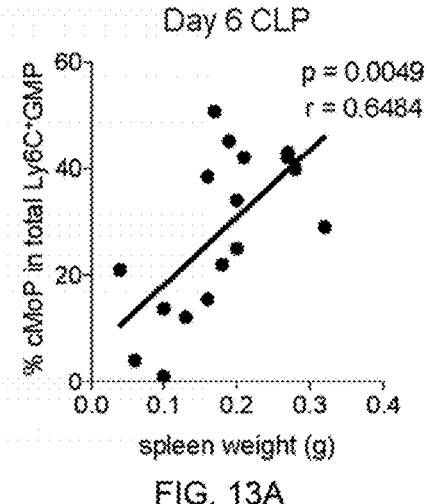
FIG. 13. Skewed specification of GMPs towards neutrophil commitment is directed by G-CSF during emergency granulopoiesis. (A) Pearson correlation of the percentage of cMoPs among Ly6C⁺GMPs against spleen sizes measured in grams. (B) Cytokine profile of septic mice at the in the indicated timepoints of sepsis onset. Results are expressed as relative concentrations (normalised per analyte) from low (light) to high (dark) levels.

To determine the factors and signals that enabled the expansion of proNeu1 and proNeu2, the inventors performed a screen of inflammatory analytes on mice serum at the various time points (FIG. 13B). Specifically, high levels of G-CSF and IL-6 were found at day 3, which may account for the skewed neutrophil potential (FIG. 6B). This is supported by a significant increase in proNeu frequencies through in vivo administration of G-CSF (FIG. 6C). To demonstrate this instructive skewing effect, myelo-ablated mice BM cells were analysed using a chemotherapeutic drug 5-Fluorouracil, and G-CSF was introduced during the recovery of the myeloid compartment. Introduction of G-CSF at day 9 showed a marked increase in proNeu1 frequency at day 12 after myeloablation (FIG. 6D), and this translated into much higher neutrophil production on day 15 (FIG. 6E). Taken together, the data highlights the relevance of the proNeu findings by providing a framework to understand the biology of sepsis through the comprehension of progenitor skewing. Notably, the results support the G-CSF-mediated skewing effect of proNeu commitment in the early phase of the sepsis inflammatory phase, which is subsequently compensated by high monocyte production and commitment for effective resolution of sepsis.

InfinityFlow of Human Cord Blood Cells Reveal a proNeu1 and a proNeu2 Subset

To determine if such progenitors exist in human, the same workflow (i.e., the InfinityFlow pipeline) was applied to examine whole human cord blood cells to screen for differential surface markers that can help identify these progenitor cells.

Briefly, Red blood cells (RBC)-lysed cord blood cells are stained with a common backbone panel of surface markers that denote the various cell lineages present in the cord blood. Thereafter, cells are aliquoted into wells, each containing a unique PE-conjugated surface marker (LEGEND-Screen™). Samples are acquired and the expression profiles of each PE marker was processed with InfinityFlow, a machine learning application that predicts the co-expression profile of each marker with every tested marker. This allowed for the discovery of new subsets with high dimensional phenotypic characterisation.

Figures 7A, 7B:
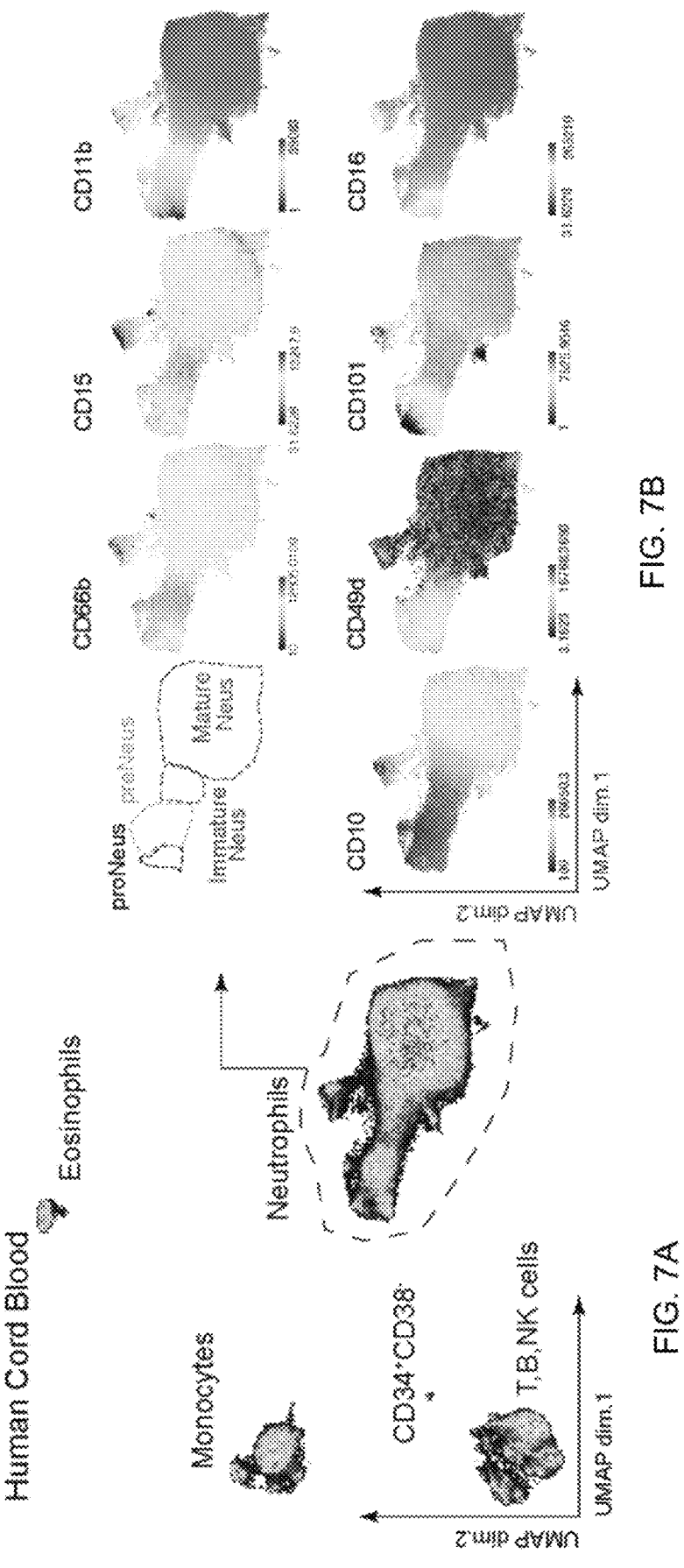
FIG. 7. InfinityFlow of human cord blood characterises 2 proNeu subsets. (A) UMAP of total (red blood cell lysed) umbilical cord blood cells. Each cluster is annotated according to their marker profiles. T,B,NK cells were clustered together as their markers were grouped together as lineage exclusion makers. (B) Expression plots of backbone markers denoting the various neutrophil subsets. Results are expressed as scaled fluorescence intensity. (C) InfinityFlow predicted expression levels of putative markers for proNeu identification. Results are expressed as scaled predicted fluorescence intensity from low (light) to high (dark) levels. (D) Gating of proNeus (left) reveals a rare SSC$^{lo}$CD49d$^+$ proNeu1 and SSC$^{hi}$ CD49d$^{int}$proNeu2 subset (right). As proNeu1 cells were rare, the FACS plot of proNeu subsets was generated from a concatenation of all LEGEND-Screen™ sample files. (E) Histogram plots of fluorescence intensities of proNeu subsets. (F) FACS analysis of neutrophil subsets from cord blood, peripheral blood and fetal bone marrow samples. (G) Taking the top-expressing markers from each subset (MFI>10$^3$), a side-by-side comparative heatmap was generated and plotted. Expression is represented as a Z-score of Log$_2$MFIs normalised per marker, from low (light) to high (dark) levels. (See also FIG. 14).
Figures 7C, 7D, 7E:
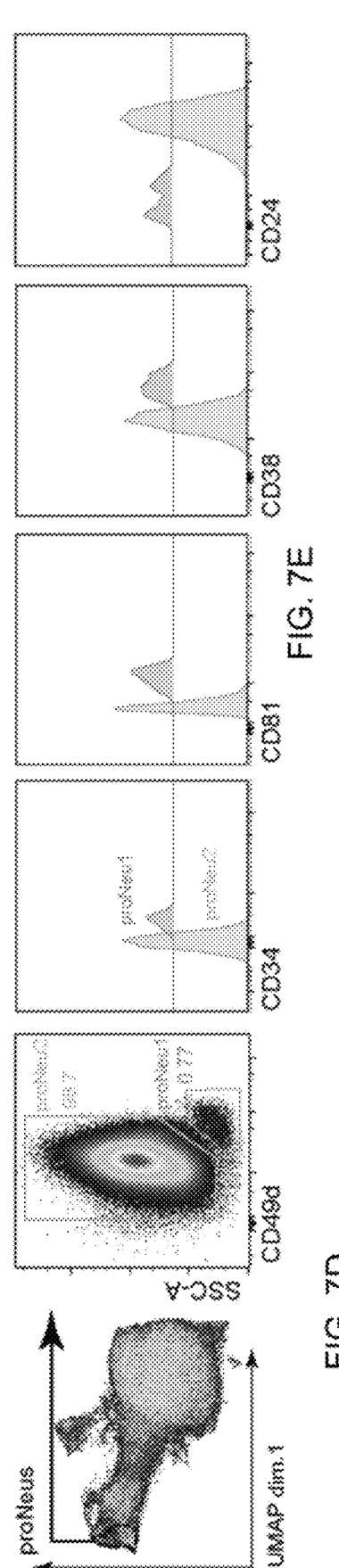

UMAP analysis of total cord blood cells showed distinct populations representing the various lineages (FIG. 7A). Deeper analysis into the neutrophil cluster revealed the previously identified three bone marrow neutrophil subsets, with similar protein expression profiles as described in mouse. Importantly, through UMAP, a putative proNeu population possessing low expression levels of CD11b and high levels of CD49d was identified (FIG. 7B). Mining on the InfinityFlow dataset, the inventors further identified several potential markers for human proNeu identification. These included CD71, LOX-1, CD164, CD112, CD181 and TACSTD2 (FIG. 7C). Validation of one of these markers, CD71, showed that it was exclusively expressed by proNeus among total RBC-lysed cord blood cells (FIG. 14A). This suggests a possible isolation strategy of proNeus (FIG. 14B). This strategy is an easy 2-step process, which utilizes large volumes of donor cord blood commonly available for clinical use. These cells are typically discarded after enrichment for CD34⁺ stem and progenitor cells which are used for cell therapeutic purposes.

Figures 7F, 7G:
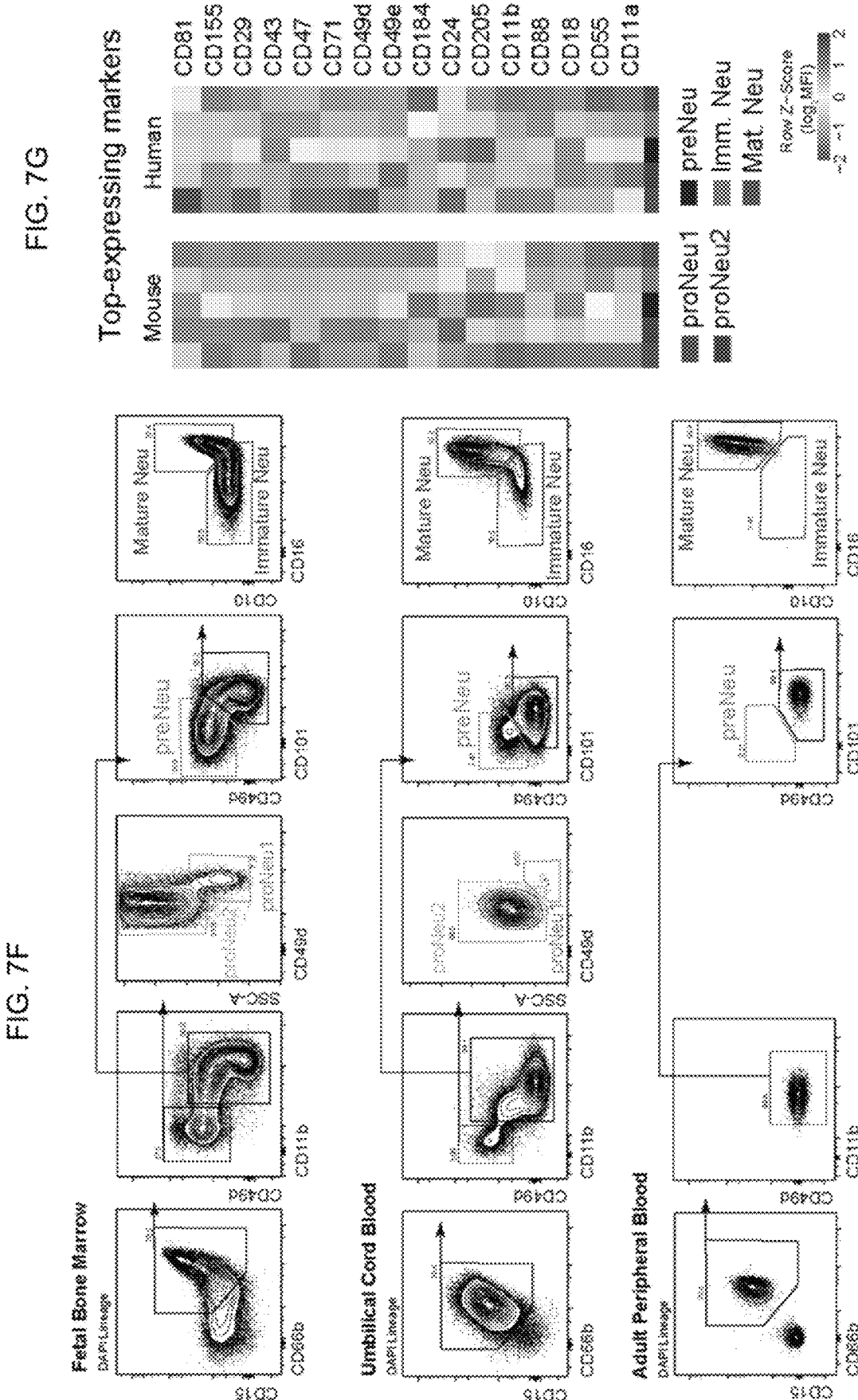

The inventors could further subset proNeus into proNeu1 and proNeu2 by their CD49d expression level and side-scatter properties (FIG. 7D). CD49d$^{hi}$SSC$^{lo}$ proNeu1 were rare cells as compared to CD49d$^{int}$SSC$^{hi}$ proNeu2, and they expressed higher levels of CD34, CD38 and CD81 (FIG. 7E). The expression of CD34 and CD38 suggests that proNeu1 cells exist within the human GMP nomenclature of Lin-CD34$^{+}$CD38$^{+}$CD45RA$^{+}$ cells. To validate the findings, cord and adult peripheral blood, as well as fetal bone marrow samples were analysed. From the analysis, the inventors were able detect proNeu1 and proNeu2 in cord blood donor samples but not in the peripheral blood. In the fetal bone marrow, the inventors could detect a higher frequency of proNeu1, along with higher frequencies of proNeu2, preNeus and immature Neus (FIG. 7F).

Figure 14C:
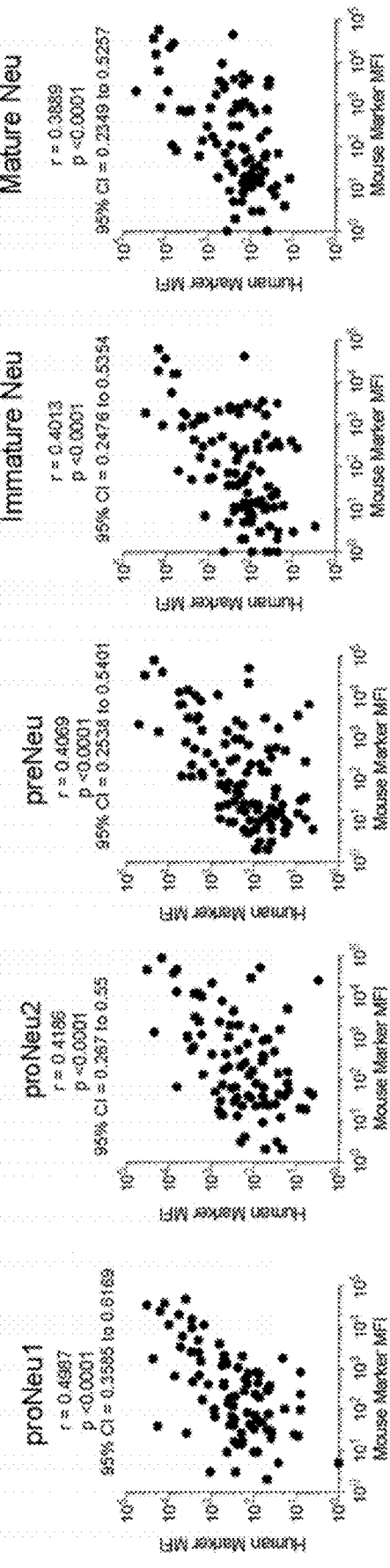
FIG. 14 (related to FIG. 7). CD71 specifically isolates proNeus from cord blood. (A) Expression plot of CD71 visualised on UMAP of total cord blood cells. Expression is represented as relative fluorescence intensity (predicted). (B) Flow cytometric validation of CD71 as putative marker for proNeu isolation. (C) Spearman rank correlation plots of mouse surface marker MFI against human surface marker MFI. Each dot represents a common surface marker expressed both in mouse and human (n=140).

The data suggest a similarity in neutrophil development between mouse and human with the identification of human equivalents of proNeu1 and proNeu2. To further show this correlation, the inventors utilized and compared the protein expression profiles of each neutrophil subset from both the mouse and human InfinityFlow datasets. The MFIs were extracted from each subset and it was observed that each subset had moderate correlation between the mouse and human equivalent neutrophil subset (FIG. 14C). Moreover, by comparing the top-expressing markers of each subset in both mouse and human, 16 markers that share similar expression progression from proNeu1 to mature neutrophils were identified (FIG. 7G). This further suggests a similar acquisition of function and maturation in both mice and human. Taken together, the data provides a complete analysis of the human neutrophil pathway, identifying the human equivalents of proNeu1 and proNeu2 with their associated surface marker expression profiles.

Figure 15:
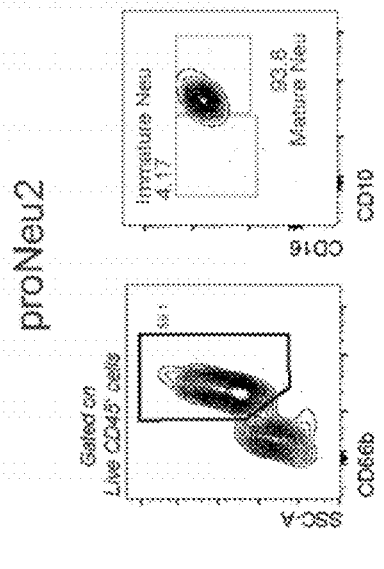
FIG. 15. In vitro differentiation capacity of proNeu subsets. Sorted cells of CD34$^{hi}$ (stem and progenitors), proNeu1 and proNeu2 were cultured for three days in serum-free media containing myeloid expansion supplement (Stem Cell Technologies). Cells were then harvested and analysed for mature neutrophil (CD66b⁺CD16⁺CD10⁺) progeny. Data is representative of 4 donor frozen fetal marrow samples.
Figure 15:
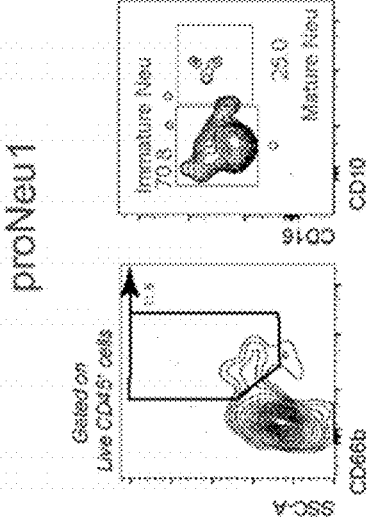
Figure 15:
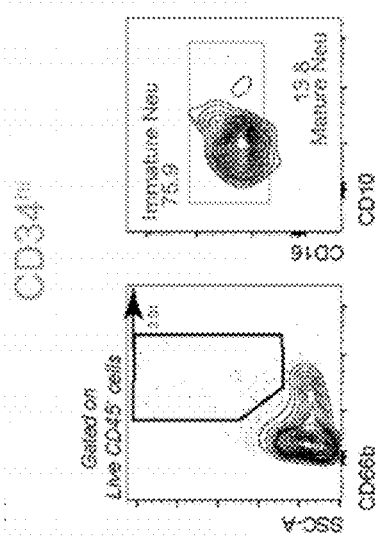

Finally, to show that the identified progenitors proNeu1 and proNeu2 have the potential to generate mature neutrophils, in vitro cultures of sorted proNeu1 and proNeu2 cells were performed. The data showed that both proNeu1 and proNeu2 were capable of generating CD16$^{+}$CD10$^{+}$ mature neutrophils (FIG. 15). This generation takes 3 days, which provides a quick supply of neutrophils if transferred into patients who undergo myeloablative treatments. This is observed in the CD34$^{hi}$ cultured cells, which generate very low numbers of mature neutrophils after 3 days of culture. This finding also allows for the further development of culture conditions that will allow for the extended proliferation and expansion of donor neutrophils for therapeutic purposes. Taken together, the data strongly supports the existence of two distinct neutrophil progenitors and the method to isolate these cells for therapeutic uses.

Discussion

The classical model of haematopoiesis is a hierarchical and step-wise differentiation program, led by instructive transcription factors that govern each cell's lineage fate. The generation of myeloid cells are through GMPs (Lin-cKit$^{+}$ Sca-1-CD34$^{+}$CD16/32$^{hi}$) as shown by the formation of both granulocytic and monocytic colonies in methylcellulose colony-forming assays (Akashi et al., 2000). Yet, whether GMPs are a bona fide homogenously multipotent subset or a heterogenous blend of lineage-restricted populations remains a long-standing question. To gain better insights into this, the inventors employed a combinatorial approach of transcriptomic, proteomic and bioinformatic tools to develop a phenotyping scheme for identifying putative progenitors within the GMP populations. By subjecting the currently defined GMPs through optimized subset-defining surface markers derived from InfinityFlow (Dutertre et al., 2019) and bioinformatic approaches, the inventors identified a population of neutrophil-committed progenitors (i.e. CD81$^{+}$CD106-proNeu1) that exist within GMP population. Furthermore, with deep surface marker phenotyping and RNA-Seq profiling, the inventors further characterized a downstream CD81$^{+}$CD106$^{+}$proNeu2 progenitor subset. Together, these data serve as a missing link in the early stages of the neutrophil developmental pathway, which allows for the mapping of their development from proNeu1→proNeu2→preNeu→immature neutrophil→mature neutrophil.

The ability to delineate early neutrophil progenitors from GMPs allows for the assessment of transcription factors that are involved in instructing myeloid progenitor lineage specification and commitment. Inspection of a list of TFs (Irf8, KIf4, Irf5, Gfi1, Cebpe and Per3) that are known to govern monocytic and granulocytic lineage commitment consistently showed that Ly6C-GMPs and proNeu1 express similar levels of these TFs, while differential expression of these TFs only became evident at the proNeu2 and cMoP stage. This indicates that a neutrophil-monocyte lineage bifurcation may occur at this hierarchical level. This raises the question about the extent of lineage commitment by proNeu1 population, i.e., whether this subset of progenitor is specified or committed towards the neutrophil lineage. The in vitro and in vivo functional studies revealed that proNeu1 is committed to the neutrophil lineage, as proNeu1 can only give rise to neutrophils even when they were cultured with a strong monocytic lineage promoting cytokine such as M-CSF. Additionally, the RNA-Seq data showed that cMoP, Ly6C-GMP, proNeu1 and proNeu2 possess distinct "TF signatures", providing an overview of putative TFs that could be important for lineage specification and commitment of these progenitors. For instance, the inventors observed increased levels of Jag1 and Sox13 expression specifically only in proNeu1, suggesting that these two TFs can be developed as markers for tagging proNeu1 and to be examined as key regulators for proNeu1 differentiation. Collectively, the data not only confirmed previous lineage-associated TFs, but also extended the list of putative TFs for myeloid lineage specification and commitment.

A previous in vivo tracking study demonstrated that granulocytes and monocytes are closely related in terms of their clonal origin. Here, the disclosure describes a transcriptionally and molecularly defined neutrophil progenitor in the GMP hierarchy, allowing for a better understanding of the lineage relationships and the dynamics of neutrophil/monocyte production. Given that myeloid progenitors can be sustained without the input from HSCs, it is conceivable that these progenitors are highly adaptable to varying inflammatory perturbations, according to the demands of the immune response. The study revealed that there is a selective expansion of proNeu1 and disappearance of cMoP during the acute phase of sepsis onset. This phenomenon could be a consequence of skewed differentiation potential of progenitor cells, conceivably at the Ly6C-GMP level, and a preferential proliferation of early neutrophil progenitors to meet the immediate requirements for neutrophils.

In summary, the disclosure provides new insight into the divergent pathways of myeloid progenitor development towards neutrophils and monocytes from GMPs, and how the balance between neutrophil/monocyte production is important for host homeostasis. Moreover, the identification of early neutrophil progenitors opens up new avenues for therapeutic strategy for the management of neutropenia in hematopoietic stem cell transplantation or high dose chemotherapy, by the infusion of an expanded proNeu subset.

This can serve a source for rapid neutrophil repopulation to help confer protection against infection during this critical period of need.

Materials and Methods

Mice

Eight to twelve-week-old C57BL/6 mice were bred and maintained under specific pathogen-free (SPF) conditions in the Biological Resource Centre (BRC) of A*STAR, Singapore. Both males and females were used for experiments, but animals were sex- and age-matched in each experiment as much as possible. uGFP (C57BL/6-Tg(UBC-GFP) 30Scha/J), CD45.1 (B6.SJL-Ptprc$^a$ Pepc$^b$/BoyJ), MaFIA (C57BL/6-Tg(Csf1 r-EGFP-NGFR/FKBP1A/TNFRSF6) 2Bck/J) and Rosa26$^{mT/mG}$ (STOCK Gt (ROSA)$^{26sotm4(AcTB-tdTomato,-EGFP)Luo}$/J mice were obtained from The Jackson Laboratory. Fucci-S/G2/M (#474) were obtained from the RIKEN BioResource Center (Ibaraki, Japan; (Tomura et al., 2013)). Cebpe$^{-/-}$ provided by P. Koeffler (Cancer Science Institute of Singapore, NUS, Singapore) (Yamanaka et al., 1997). All transgenic mice were maintained on a C57BL/6 background and experiments were performed under the approval of the Institutional Animal Care and Use Committee (IACUC), in accordance with the guidelines of the Agri-Food and Veterinary Authority (AVA) and the National Advisory Committee for Laboratory Animal Research (NACLAR) of Singapore.

Human Blood, Cord Blood and Fetal Bone Marrow

All samples were obtained in accordance with a favorable ethical opinion from SingHealth CIRB or A*STAR, the Singapore Immunology Network. Fresh (<24 hours from collection) human umbilical cord blood (UCB) units were collected through a collaboration with National Cancer Centre Singapore (NCCS). NCCS obtained the UCB units through Singapore Cord Blood Bank (SCBB), from research consented units failing to meet the criteria for public clinical banking. Usage of the samples were approved by the Centralized Institutional Review Board (CIRB) of Singapore Health Services (that covers NCCS) as well as the dedicated Research Advisory Ethics Committee of SCBB.

Treatments

For 5-Fluorouracil (5-FU) myeloablative treatment, mice were injected once intraperitoneally with 150 mg/kg 5-FU (Sigma-Aldrich) or PBS control. For G-CSF treatment, mice were injected once intraperitoneally with 1.5 µg of G-CSF/ anti-G-CSF antibody complex (G-CSFcx) as previously described (Rubinstein et al., 2013). Briefly, G-CSFcx were generated by incubating G-CSF (Neupogen) and anti-G-CSF (BVD11-37G10; Southern-Biotech) at 1:5 cytokine to antibody ratio for 20 min at 37° C., and were next diluted at least 10-fold in PBS before injection.

Tissue Preparation and Data Analysis for Flow Cytometry and Cell Sorting

Blood was obtained via an incision in the submandibular region and was then lysed in red blood cell lysis buffer (eBioscience). For BM cells, mice femurs were flushed using a 23-gauge needle in PBS containing 2 mM EDTA and 2% fetal bovine serum (FBS) and passed through a 70-µm nylon mesh sieve. Spleens were harvested and homogenized into single-cell suspensions using 70-µm nylon mesh sieves and syringe plungers. Antibodies were purchased from BD, Biolegend, eBioscience or R&D. For the identification of BM myeloid progenitor cell subsets, cells were stained with fluorophore-conjugated anti-mouse antibodies against CD34 (RAM34), CD11b (M1/70), CD16/32 (2.4G2), CD115 (AFS598), cKit (2B8), CXCR2 (SA044G4), CXCR4 (2B111), Gr1 (RB6-8C5), Ly6C (HK1.4) CD106 (429), CD81 (Eat-2), and Flt3 (A2F10), together with exclusion lineage markers that include Ly6G (1A8), CD90.2 (53-2.1), B220 (RA3-6B2), NK.1.1 (PK136), and Sca-1 (D7). After exclusion of cell doublets and dead cells with DAPI, proNeu1 were identified as (Lin/CD115/Flt3)-cKit$^{hi}$CD16/ 32$^{hi}$Ly6C$^+$ CD34$^{hi}$CD11b$^{lo}$CD106$^-$, proNeu2 were identified as (Lin/CD115/Flt3)$^-$cKit$^{hi}$CD16/32$^{hi}$Ly6C$^+$ CD34$^{hi}$CD11b$^{hi}$CD106$^+$, preNeus were identified as (Lin/ CD115/Siglec-F)$^-$Gr1$^+$CD11b$^+$CXCR4$^h$ $^i$ckit$^{int}$CXCR2$^-$, CMPs were identified as Lin$^-$cKit$^+$Sca-1$^-$CD16/ 32$^{int}$CD34$^{int}$, Ly6C$^-$GMPs were identified as Lin$^-$cKit$^+$Sca-1$^-$CD16/32$^{hi}$CD34hi, MDPs were identified as Lin$^-$cKit$^+$ Sca-1$^-$CD115$^+$Flt3$^+$Ly6C$^-$ or and cMoPs were identified as Lin$^-$cKit$^+$Sca-1$^-$CD115$^+$CD81$^-$Flt3$^-$Ly6C$^+$. Flow cytometry acquisition was performed on a 5-laser BD LSR II (BD) using FACSDiva software, and data was subsequently analyzed with FlowJo software (Tree Star). Cell numbers were quantified with count beads (CountBright; Life Technologies) according to the manufacturer's instructions. Sorting of BM neutrophil subsets were performed using a BD ARIAII (BD) to achieve >98% purity.

LEGENDScreen™ and InfinityFlow Pipeline

Mice femurs, tibias, pelvic bones, humeri and spinal bone marrow were harvested and crushed in PBS containing 2 mM EDTA and 2% foetal bovine serum (FBS) and passed through a 70-µm nylon mesh sieve. For human cord blood, RBC lysis was performed on one unit of cord blood donor sample for 10 min at room temperature. Cells were spun down at 400 g for 10 min. This process was repeated once to remove most RBC cells. Mouse cells were first stained with fixable live/dead for 30 min before staining with a backbone panel cocktail of mouse antibodies to define the various lineages in the BM. These markers include: CD34 (RAM34), CD11b (M1/70), CD16/32 (2.4G2), CD115 (AFS598), cKit (2B8), CXCR2 (SA044G4), Ly6C (HK1.4), Flt3 (A2F10), Sca-1 (D7). CD48 (HM48-1), CD43 (S11), CD62L (MEL-14) and FITC-conjugated lineage markers (Ly6G (1A8), CD90.2 (53-2.1), B220 (RA3-6B2), NK.1.1 (PK136)). After 90 min of staining at 4° C., cells were lysed in 1×RBC lysis (eBioscience) for 5 min, then spun down at 400 g for 5 min. Cells were then stained with secondary streptavidin for 30 min and washed as before. To enrich the BM for progenitor identification, mature neutrophils, B, T and NK cells were partially depleted using FITC selection kit (Stem Cell Technologies) according to the manufacturer protocol. For cord blood cells, cells were stained with a backbone panel of antibodies for 30 min at 4° C., including: CD3 (UCHT1), CD56 (HCD56), CD19 (HIB19), CD10 (H110a), CD49d (9F10), CD34 (581), CD66b (G10F5), cKit (104D2), CD38 (HIT2), CD15 (H198), CD14 (M5E2), CD101 (BB27), CD45 (H130), CD11b (ICRF44), CD16 (3G8). Cells were then counted and aliquoted into individual wells containing specific PE-conjugated marker. (Tables 1 and 3). After staining for 30 min, plates were washed and fixed before FACS acquisition was performed on a 5-laser BD LSR II (BD) using FACSDiva software, and data was subsequently processed through the InfinityFlow pipeline as described elsewhere (Dutertre et al., 2019).

Cytospin and Wright-Giemsa Staining

Sorted neutrophil subsets (5×10$^4$ cells each) were spun onto glass slides using Cytospin 4 Cytocentrifuge (Thermo scientific), dried for 10 minutes, fixed in methanol and stained with the Hema 3 manual staining system (Fisher Diagnostics) according to the manufacturer's protocol. Images were acquired with an Olympus BX43 equipped with a 100× oil immersion objected, and image brightness was adjusted with Photoshop (Adobe).

Transcriptomics

For single-cell transcriptomic analysis, BM CMPs, GMPs, preNeus and TpMos cells were sorted based on the gating strategy depicted in FIGS. 1B and 8C. Single cell cDNA libraries were using the SMARTSeq v2 protocol (Picelli et al., 2014) with the following modifications: 1. 1 mg/ml BSA Lysis buffer (Ambion® Thermo Fisher Scientific, Waltham, Mass., USA); 2. Use of 200 pg cDNA with 1/5 reaction of Illumina Nextera XT kit (Illumina, San Diego, CA, USA). The length distribution of the cDNA libraries was monitored using a DNA High Sensitivity Reagent Kit on the Perkin Elmer Labchip (Perkin Elmer, Waltham, MA, USA). All samples were subjected to an indexed paired-end sequencing run of 2×151 cycles on an Illumina HiSeq 4000 system (Illumina, San Diego, CA, USA) (250 samples/lane).

For total-mRNA bulk RNA-seq analysis, BM Ly6C-GMP, proNeu1, proNeu2 and cMoP were sorted based on the gating strategy of FIG. 4A. preNeus were sorted as described previously. Total RNA was extracted using Arcturus PicoPure RNA Isolation kit (Applied Biosystems™ Thermo Fisher Scientific) according to manufacturer's protocol. All human RNAs were analyzed on Agilent Bioanalyser for quality assessment with a median RNA Integrity Number (RIN) of 9.4. cDNA libraries were prepared using 2 ng of total RNA with 1 ul of 1:50,000 dilution of ERCC RNA Spike in Controls respectively (Ambion® Thermo Fisher Scientific) using the SMARTSeq v2 protocol (Picelli et al., 2014) with the following modifications: 1. Addition of 20 µM TSO; 2. Use of 200pg cDNA with 1/5 reaction of Illumina Nextera XT kit (Illumina, San Diego, CA, USA). The length distribution of the cDNA libraries was monitored using a DNA High Sensitivity Reagent Kit on the Perkin Elmer Labchip (Perkin Elmer, Waltham, MA, USA). All samples were subjected to an indexed paired-end sequencing run of 2×151 cycles on an Illumina HiSeq 4000 system (Illumina) (26 samples/lane). Raw reads were aligned to mouse genome build GRCm38 using STAR aligner. Read counts per gene were then calculated using the feature-Counts (part of the Subread package) based on GENCODE gene annotation version M20. Log 2 transformed reads per kilobase per million mapped reads (log 2 RPKM) normalization was done to account for transcript length and the total number of reads. Differentially expressed genes (DEGs) analysis was done using edgeR (Robinson et al., 2009) on protein coding genes only. DEGs with FDR (False Discovery Rate) less than 0.05 were selected as statistically significant.

In Vitro Cell Culture

Sorted cells (1×10⁴ for each subset) were plated onto 96-well plates in triplicates and cultured at 37° C., 5% $CO_2$ in StemSpan™ SFEM II (Stem Cell Technologies) containing penicillin (100 U/ml), streptomycin (100 ug/ml), a combination of cytokines (50 ng/ml SCF, 10 ng/ml LIF, 20 ng/ml IL-3, 20 ng/ml IL-6) and with or without 50 ng/ml CSF-1. For human fetal marrow cultures, frozen samples were thawed and sorted before plating in 96-well plates in StemSpan™ SFEM II containing penicillin (100 U/ml), streptomycin (100 ug/ml) and StemSpan™ myeloid expansion supplement (Stem Cell Technologies). For colony assays, sorted cells (3×10⁴) were cultured for in Iscove's modified Dulbecco's medium (Sigma) with 25 mM HEPES and L-Glutamine (Chemtron) containing 10% (vol/vol) FBS, 1 mM sodium pyruvate, penicillin (100 U/ml) and streptomycin (100 ug/ml), 1% (wt/vol) methylcellulose (MethoCult M3234, Stem Cell Technologies) and the same cytokine combination as above. Representative colony images were collected with an Olympus IX-81 microscope (Olympus). Image brightness was adjusted with Photoshop.

Adoptive Cell Transfer

Sorted uGFP⁺ proNeu1, RFP⁺ (Rosa26$^{mT/mG}$) proNeu2 and CD45.1 preNeus (5×10⁴ cells each) were transferred intra-BM into wildtype recipients as described previously (Chong et al., 2016). Briefly, recipient mice were anesthetized with ketamine (150 mg/kg)/xylazine (10 mg/kg), and had their right leg shaved to expose the kneecap. Sorted proNeu1, proNeu2 and preNeus were mixed and resuspended in 1×PBS in equal proportions and a volume of 10 µL was administered into the tibia through the kneecap using a 29-gauge insulin needle. For single population transfers, sorted uGFP⁺Ly6C-GMP, proNeu1 and proNeu2 (5×10⁴ cells) were used. After 24 hr or 72 hours after cell transfer, tibias were collected, stained and analyzed by flow cytometry.

CLP-Induced Sepsis

Cecal ligation and puncture was performed as described previously (Rittirsch et al., 2009). Briefly, the peritoneal cavity was exposed under ketamine/xylazine anesthesia and the cecum was exteriorized. 50% (mid-grade) or 80% (high-grade) of the cecum was ligated distal of the ileo-cecal valve using a non-absorbable 7-0 suture. A 26-gauge needle was used to perforate the distal end of the cecum, and a small drop of feces was extruded through the puncture before being relocated into the peritoneal cavity. The peritoneum was closed and mice were subsequently treated with saline and Buprenorphine (5-20 mg/kg) by subcutaneous injection. For sham-operated controls, the peritoneum was exposed and the cecum was exteriorized before closing the peritoneum as mentioned above. Mice were euthanized and harvested 2 weeks after the surgery.

Quantification and Statistical Analysis

Statistical analyses were done using Prism software (Graphpad). Student's t-test or one-way analysis of variance (ANOVA) with Bonferroni correction were performed.

Tables

TABLE 1

(Related to FIG. 2) List of surface markers
tested in mouse BM LEGENDScreen ™

| Location | Marker | Clone (Biolegend) | Isotype |
|---|---|---|---|
| Plate_1_A1_013 | Blank | | |
| Plate_1_A10_022 | CD103 | 2E7 | Armenian Hamster IgG |
| Plate_1_A11_023 | Delta_like 4 | HMD4-1 | Armenian Hamster IgG |
| Plate_1_A12_024 | CD195 | HM-CCR5 | Armenian Hamster IgG |
| Plate_1_A2_014 | Isotype_AHIgG | HTK888 | |
| Plate_1_A3_015 | CD3e | 145-2C11 | Armenian Hamster IgG |
| Plate_1_A4_016 | CD80 | 16-10A1 | Armenian Hamster IgG |

TABLE 1-continued (Related to FIG. 2) List of surface markers
tested in mouse BM LEGENDScreen ™

| Location | Marker | Clone (Biolegend) | Isotype |
|---|---|---|---|
| Plate_1_A5_017 | CD81 | Eat-2 | Armenian Hamster IgG |
| Plate_1_A6_018 | CD154 | MR1 | Armenian Hamster IgG |
| Plate_1_A7_019 | Notch 1 | HMN1-12 | Armenian Hamster IgG |
| Plate_1_A8_020 | CD30 | mCD30.1 | Armenian Hamster IgG |
| Plate_1_A9_021 | CD178 | MFL3 | Armenian Hamster IgG |
| Plate_1_B1_025 | Notch 4 | HMN4-14 | Armenian Hamster IgG |
| Plate_1_B10_034 | CD11c | N418 | Armenian Hamster IgG |
| Plate_1_B11_035 | Delta_like 1 | HMD1-3 | Armenian Hamster IgG |
| Plate_1_B12_036 | CD196 | 29-2L17 | Armenian Hamster IgG |
| Plate_1_B2_026 | CD229 | Ly9ab3 | Armenian Hamster IgG |
| Plate_1_B3_027 | CD69 | H1.2F3 | Armenian Hamster IgG |
| Plate_1_B4_028 | Notch 3 | HMN3-133 | Armenian Hamster IgG |
| Plate_1_B5_029 | JAML | 4E10 | Armenian Hamster IgG |
| Plate_1_B6_030 | Notch 2 | HMN2-35 | Armenian Hamster IgG |
| Plate_1_B7_031 | CD194 | 2G12 | Armenian Hamster IgG |
| Plate_1_B8_032 | CD152 | UC10-4B9 | Armenian Hamster IgG |
| Plate_1_B9_033 | CD120a | 55R-286 | Armenian Hamster IgG |
| Plate_1_C1_037 | CD29 | HMβ1-1 | Armenian Hamster IgG |
| Plate_1_C10_046 | CD16.2 | mDcR2-1 | Armenian Hamster IgG |
| Plate_1_C11_047 | CD36 | HM36 | Armenian Hamster IgG |
| Plate_1_C12_048 | DcTRAIL_R1 | mDcR1-3 | Armenian Hamster IgG |
| Plate_1_C2_038 | CD55 | RIKO-3 | Armenian Hamster IgG |
| Plate_1_C3_039 | Jagged 2 | HMJ2-1 | Armenian Hamster IgG |
| Plate_1_C4_040 | CD79b | HM79-12 | Armenian Hamster IgG |
| Plate_1_C5_041 | IFNgR b chain | MAR1-5A3 | Mouse IgG1, k |
| Plate_1_C6_042 | CD61 | 2C9.G2 (HMβ3-1) | Armenian Hamster IgG |
| Plate_1_C7_043 | CD121a | JAMA-147 | Armenian Hamster IgG |
| Plate_1_C8_044 | TCRb chain | GL3 | Hamster IgG |
| Plate_1_C9_045 | FceRIa | MAR-1 | Armenian Hamster IgG |
| Plate_1_D1_049 | CD84 | mCD84.7 | Armenian Hamster IgG |
| Plate_1_D10_058 | CD339 | HMJ1-29 | Armenian Hamster IgG |
| Plate_1_D11_059 | CD49a | HMa1 | Armenian Hamster IgG |
| Plate_1_D12_060 | PD1H | MH5A | Armenian Hamster IgG |
| Plate_1_D2_050 | CD48 | HM48-1 | Armenian Hamster IgG |
| Plate_1_D3_051 | CD49b | HMa2 | Armenian Hamster IgG |
| Plate_1_D4_052 | CD120b | TR75-89 | Armenian Hamster IgG |
| Plate_1_D5_053 | CD183 | CXCR3-173 | Armenian Hamster IgG |
| Plate_1_D6_054 | CD262 | MD5-1 | Armenian Hamster IgG |
| Plate_1_D7_055 | HVEM | HMHV-1B18 | Armenian Hamster IgG |
| Plate_1_D8_056 | TCR Vd1.1_1.2 | H57-597 | Armenian Hamster IgG |
| Plate_1_D9_057 | B7H4 | HMH4-5G1 | Armenian Hamster IgG |
| Plate_1_E1_061 | CD85k | H1.1 | Armenian Hamster IgG |
| Plate_1_E10_070 | Ly108 | 330-AJ | Mouse IgG2a, k |
| Plate_1_E11_071 | CD207 | 4C7 | Mouse IgG2a, k |
| Plate_1_E12_072 | CX3CR1 | SA011F11 | Mouse IgG2a, k |
| Plate_1_E2_062 | Plexin B2 | 3E7 | Armenian Hamster IgG |
| Plate_1_E3_063 | CD27 | LG.3A10 | Armenian Hamster IgG1, |
| Plate_1_E4_064 | DR3 | 4C12 | Armenian Hamster IgG1 |
| Plate_1_E5_065 | TCR gd | 4B2.9 | Armenian Hamster IgG |
| Plate_1_E6_066 | Isotype_mIgG2a | MOPC-173 | Mouse IgG2a, k |
| Plate_1_E7_067 | CD45.1 | A20 | Mouse (A.SW) IgG2a, k |
| Plate_1_E8_068 | CD45.2 | 104 | Mouse (SJL) IgG2a, k |
| Plate_1_E9_069 | NK1.1 | PK136 | Mouse IgG2a, k |
| Plate_1_F1_073 | Isotype_mIgG1 | MOPC-21 | Mouse IgG1, k |
| Plate_1_F10_082 | Trem_like 4 | 16E5 | Mouse IgG1, k |
| Plate_1_F11_083 | CD59a | mCD59.3 | Mouse IgG1, k |
| Plate_1_F12_084 | Ly49H | 3D10 | Mouse IgG1, k |
| Plate_1_F2_074 | CD66a | MAb-CC1 | Mouse IgG1, k |
| Plate_1_F3_075 | IFNAR1 | MOB-47 | Armenian Hamster IgG |
| Plate_1_F4_076 | Tim2 | F37-2C4 | Mouse IgG1, k |
| Plate_1_F5_077 | CD272 | 8F4 | Mouse IgG1, k |
| Plate_1_F6_078 | CD64 | X54-5/7.1 | Mouse IgG1, k |
| Plate_1_F7_079 | CD351 | TX61 | Mouse IgG1, k |
| Plate_1_F8_080 | LAP | TW7-20B9 | Mouse IgG1, k |
| Plate_1_F9_081 | TIGIT | 1G9 | Mouse IgG1, k |
| Plate_1_G1_085 | CD90.1 | OX-7 | Mouse IgG1, k |
| Plate_1_G10_094 | Siglec H | 551 | Rat IgG1, K |
| Plate_1_G11_095 | CD255 | MTW-1 | Rat IgG1, k |
| Plate_1_G12_096 | CD202b | TEK4 | Rat IgG1, k |
| Plate_1_G2_086 | Isotype_mIgG2b | MPC-11 | Mouse IgG2b, k |
| Plate_1_G3_087 | CD157 | BP-3 | Mouse IgG2b, k |
| Plate_1_G4_088 | CD159a | 16A11 | Mouse IgG2b, k |
| Plate_1_G5_089 | XCR1 | ZET | Mouse IgG2b, k |

TABLE 1-continued (Related to FIG. 2) List of surface markers
tested in mouse BM LEGENDScreen ™

| Location | Marker | Clone (Biolegend) | Isotype |
|---|---|---|---|
| Plate_1_G6_090 | Isotype_mIgM | MM-30 | Mouse IgM, k |
| Plate_1_G7_091 | SSEA_1 | MC-480 | Mouse IgM, k |
| Plate_1_G8_092 | Isotype_rIgG1 | RTK 2071 | Rat IgG1, k |
| Plate_1_G9_093 | Ig light chain κ | RMK-45 | Rat IgG |
| Plate_1_H1_097 | GITR Ligand | YGL 386 | Rat IgG1, k |
| Plate_1_H10_106 | Mac3 | M3/84 | Rat IgG1, k |
| Plate_1_H11_107 | CD223 | C9B7W | Rat IgG1, k |
| Plate_1_H12_109 | CD134 | OX-86 | Rat IgG1, k |
| Plate_1_H2_098 | CD147 | OX-114 | Rat IgG1, k |
| Plate_1_H3_099 | CD73 | TY/11.8 | Rat IgG1, k |
| Plate_1_H4_100 | CD51 | RMV-7 | Rat IgG1, k |
| Plate_1_H5_101 | NKG2D | CX5 | Rat IgG1, k |
| Plate_1_H6_102 | CD96 | 3.3 | Rat IgG1, k |
| Plate_1_H7_103 | Integrin b7 | FIB27 | Rat IgG1, k |
| Plate_1_H8_104 | CD210 | 1B1.3a | Rat IgG1, k |
| Plate_1_H9_105 | CD83 | Michel-19 | Rat IgG1, k |
| Plate_2_A12_119 | Isotype_rIgG2a | RTK2758 | Rat IgG2a, k |
| Plate_2_A2_111 | CD41 | MWReg30 | Rat IgG1, k |
| Plate_2_A3_112 | CD268 | 7H22-E16 | Rat IgG1, k |
| Plate_2_A4_113 | CD144 | BV13 | Rat IgG1, k |
| Plate_2_A5_114 | CD370 | 7H11 | Rat IgG1, k |
| Plate_2_A6_115 | CD369 | RH1 | Rat IgG1, k |
| Plate_2_A7_116 | PIR A/B | 6C1 | Rat IgG1, k |
| Plate_2_A8_117 | CD22 | OX-97 | Rat IgG1, k |
| Plate_2_A9_118 | E_Cadherin | DECMA-1 | Rat IgG1, k |
| Plate_2_B1_120 | MAIRV | TX70 | Rat IgG2a, k |
| Plate_2_B10_129 | CD197 | 4B12 | Rat IgG2a, k |
| Plate_2_B11_130 | CD47 | miap301 | Rat IgG2a, k |
| Plate_2_B12_131 | CD98 | RL388 | Rat IgG2a, k |
| Plate_2_B2_121 | CD146 | ME-9F1 | Rat IgG2a, k |
| Plate_2_B3_122 | VISTA | MIH63 | Rat IgG2a, k |
| Plate_2_B4_123 | CD8a | 53-6.7 | Rat IgG2a, k |
| Plate_2_B5_124 | CD275 | HK5.3 | Rat IgG2a, k |
| Plate_2_B6_125 | CD34MEC14.7 | MEC14.7 | Rat IgG2a, k |
| Plate_2_B7_126 | Sca_1 | D7 | Rat IgG2a, k |
| Plate_2_B8_127 | CD40 | 3/23 | Rat IgG2a, k |
| Plate_2_B9_128 | B220 | RA3-6B2 | Rat IgG2a, k |
| Plate_2_C1_132 | CD14 | Sa14-2 | Rat IgG2a, k |
| Plate_2_C10_141 | Tim4 | RMT4-54 | Rat IgG2a, k |
| Plate_2_C11_142 | CD71 | RI7217 | Rat IgG2a, k |
| Plate_2_C12_143 | H2 | M1/42 | Rat IgG2a, k |
| Plate_2_C2_133 | CD107a | 1D4B | Rat IgG2a, k |
| Plate_2_C3_134 | CD18 | M18/2 | Rat IgG2a, k |
| Plate_2_C4_135 | Ly6G | 1A8 | Rat IgG2a, k |
| Plate_2_C5_136 | CD21, CD35 | 7E9 | Rat IgG2a, k |
| Plate_2_C6_137 | Mac2 | M3/38 | Rat IgG2a, k |
| Plate_2_C7_138 | CD199 | 9B1 | Rat IgG2a, k |
| Plate_2_C8_139 | Ly51 | 6C3 | Rat IgG2a, k |
| Plate_2_C9_140 | IgD | 11-26c.2a | Rat IgG2a, k |
| Plate_2_D1_144 | CD45RB | C363-16A | Rat IgG2a, k |
| Plate_2_D10_153 | CD105 | MJ7/18 | Rat IgG2a, k |
| Plate_2_D12_154 | 4_1BB Ligand | TKS-1 | Rat IgG2a, k |
| Plate_2_D2_145 | CD326 | G8.8 | Rat IgG2a, k |
| Plate_2_D3_146 | IgM | RMM-1 | Rat IgG2a, k |
| Plate_2_D4_147 | CD155 | TX56 | Rat IgG2a, k |
| Plate_2_D5_148 | CD200R | OX-110 | Rat IgG2a, k |
| Plate_2_D6_149 | CD254 | IK22/5 | Rat IgG2a, k |
| Plate_2_D7_150 | IL21R | 4A9 | Rat IgG2a, k |
| Plate_2_D8_151 | CD276 | RTAA15 | Rat IgG2a, k |
| Plate_2_D9_152 | CD9 | MZ3 | Rat IgG2a, k |
| Plate_2_E1_155 | CD265 | R12-31 | Rat IgG2a, k |
| Plate_2_E10_164 | F4/80 | BM8 | Rat IgG2a, k |
| Plate_2_E11_165 | CD94 | 18d3 | Rat IgG2a, k |
| Plate_2_E12_166 | CD267 | 8F10 | Rat IgG2a, k |
| Plate_2_E2_156 | TLR4 | MTS510 | Rat IgG2a, k |
| Plate_2_E3_157 | CD19 | 6D5 | Rat IgG2a, k |
| Plate_2_E4_158 | LPAM_1 | DATK32 | Rat IgG2a, k |
| Plate_2_E5_159 | CD62L | MEL-14 | Rat IgG2a, k |
| Plate_2_E6_160 | CD23 | B3B4 | Rat IgG2a, k |
| Plate_2_E7_161 | CD5 | 53-7.3 | Rat IgG2a, k |
| Plate_2_E8_162 | CD273 | TY25 | Rat IgG2a, k |
| Plate_2_E9_163 | CD31 | 390 | Rat IgG2a, k |
| Plate_2_F1_167 | Ly_49A | YE1/48.10.6 | Rat IgG2a, k |
| Plate_2_F10_176 | PDC_TREM | 4A6 | Rat IgG2a, k |

TABLE 1-continued (Related to FIG. 2) List of surface markers
tested in mouse BM LEGENDScreen ™

| Location | Marker | Clone (Biolegend) | Isotype |
|---|---|---|---|
| Plate_2_F11_177 | CD135 | A2F10 | Rat IgG2a, k |
| Plate_2_F12_178 | CD127 | A7R34 | Rat IgG2a, k |
| Plate_2_F3_169 | CD11a | M17/4 | Rat IgG2a, k |
| Plate_2_F4_170 | LT beta R | 5G11 | Rat IgG2a, k |
| Plate_2_F6_172 | CD106 | 429 (MVCAM.A) | Rat IgG2a, k |
| Plate_2_F7_173 | CD365 | RMT1-4 | Rat IgG2a, k |
| Plate_2_F8_174 | CD115 | AFS98 | Rat IgG2a, k |
| Plate_2_F9_175 | CD140a | APA5 | Rat IgG2a, k |
| Plate_2_G1_179 | CD140b | APB5 | Rat IgG2a, k |
| Plate_2_G10_188 | CD200R3 | Ba13 | Rat IgG2a, k |
| Plate_2_G11_189 | MAIR_IV | TX69 | Rat IgG2a, k |
| Plate_2_G12_190 | Ly49D | 4E5 | Rat IgG2a, k |
| Plate_2_G2_180 | ESAM | 1G8/ESAM | Rat IgG2a, k |
| Plate_2_G3_181 | CD200 | OX-90 | Rat IgG2a, k |
| Plate_2_G4_182 | CD309 | Avas12 | Rat IgG2a, k |
| Plate_2_G5_183 | TLT_2 | MIH47 | Rat IgG2a, k |
| Plate_2_G6_184 | CD253 | N2B2 | Rat IgG2a, k |
| Plate_2_G7_185 | CD335 | 29A1.4 | Rat IgG2a, k |
| Plate_2_G8_186 | CD205 | NLDC-145 | Rat IgG2a, k |
| Plate_2_G9_187 | Galectin9 | 108A2 | Rat IgG2a, k |
| Plate_2_H1_191 | CD123 | 5B11 | Rat IgG2a, k |
| Plate_2_H10_200 | CD63 | NVG-2 | Rat IgG2a, k |
| Plate_2_H11_201 | CD49e | 5H10-27(MFR5) | Rat IgG2a, k |
| Plate_2_H12_202 | CD193 | J073E5 | Rat IgG2a, k |
| Plate_2_H2_192 | CD355 | 11-5/CRTAM | Rat IgG2a, k |
| Plate_2_H3_193 | CD169 | 3D6.112 | Rat IgG2a, k |
| Plate_2_H4_194 | CD138 | 281-2 | Rat IgG2a, k |
| Plate_2_H5_195 | CD160 | 7H1 | Rat IgG2a, k |
| Plate_2_H6_196 | CD39 | Duha59 | Rat IgG2a, k |
| Plate_2_H7_197 | GARP | F011-5 | Rat IgG2a, k |
| Plate_2_H8_198 | CD179a | R3 | Rat IgG2a, k |
| Plate_2_H9_199 | CD371 | 5D3/CLEC12A | Rat IgG2a, k |
| Plate_3_A10_212 | MAdCAM1 | MECA-367 | Rat IgG2a, k |
| Plate_3_A11_213 | MERTK | 2B10C42 | Rat IgG2a, k |
| Plate_3_A12_214 | CD226 | TX42.1 | Rat IgG2a, k |
| Plate_3_A2_204 | CD300LG | ZAQ5 | Rat IgG2a, k |
| Plate_3_A3_205 | CD301 | LOM-8.7 | Rat IgG2a, k |
| Plate_3_A4_206 | IL33Ra | DIH9 | Rat IgG2a, k |
| Plate_3_A5_207 | CD304 | 3E12 | Rat IgG2a, k |
| Plate_3_A6_208 | CD6 | OX-129 | Rat IgG2a, k |
| Plate_3_A7_209 | CD100 | BMA-12 | Rat IgG2a, k |
| Plate_3_A8_210 | CD104 | 346-11A | Rat IgG2a, k |
| Plate_3_A9_211 | CD182 | SA044G4 | Rat IgG2a, k |
| Plate_3_B1_215 | Ly6K | MK34 | Rat IgG2a, k |
| Plate_3_B10_224 | CD43 | S11 | Rat IgG2b, k |
| Plate_3_B11_225 | FR4 | 12A5 | Rat IgG2b, k |
| Plate_3_B12_226 | CD1d | 1B1 | Rat IgG2b, k |
| Plate_3_B2_216 | CD16/32 | 93 | Rat IgG2a, λ |
| Plate_3_B3_217 | CD150 | TC15-12F12.2 | Rat IgG2a, λ |
| Plate_3_B4_218 | CD25 | PC61 | Rat IgG2a, λ |
| Plate_3_B5_219 | CD38 | 90 | Rat IgG2a, λ |
| Plate_3_B6_220 | CD133 | 315-2C11 | Rat IgG2a, λ |
| Plate_3_B7_221 | CD301b | URA-1 | Rat IgG2a, λ |
| Plate_3_B8_222 | CD34_SA376A4 | SA376A4 | Rat IgG2a, λ |
| Plate_3_B9_223 | Isotype_rIgG2b | RTK4530 | Rat IgG2b, k |
| Plate_3_C1_227 | CD70 | FR70 | Rat IgG2b, k |
| Plate_3_C10_236 | CD24 | M1/69 | Rat IgG2b, k |
| Plate_3_C11_237 | Gr1 | RB6-8C5 | Rat IgG2b, k |
| Plate_3_C12_238 | CD86 | PO3 | Rat IgG2b, k |
| Plate_3_C2_228 | CD4 | GK1.5 | Rat IgG2b, k |
| Plate_3_C3_229 | IA/IE | M5/114.15.2 | Rat IgG2b, k |
| Plate_3_C4_230 | CD153 | RM153 | Rat IgG2b, k |
| Plate_3_C5_231 | CD54 | YN1/1.7.4 | Rat IgG2b, k |
| Plate_3_C6_232 | 33D1 | 33D1 | Rat IgG2b, k |
| Plate_3_C7_233 | CD90.2 | 30-H12 | Rat IgG2b, k |
| Plate_3_C8_234 | TER119 | TER-119 | Rat IgG2b, k |
| Plate_3_C9_235 | CD49d | R1-2 | Rat IgG2b, k |
| Plate_3_D1_239 | CD11b | M1/70 | Rat IgG2b, k |
| Plate_3_D10_248 | CD3 | 17A2 | Rat IgG2b, k |
| Plate_3_D11_249 | CD274 | 10F.9G2 | Rat IgG2b, k |
| Plate_3_D12_250 | CD117 | 2B8 | Rat IgG2b, k |
| Plate_3_D2_240 | CD45 | 30-F11 | Rat IgG2b, k |
| Plate_3_D3_241 | CD279 | RMP1-30 | Rat IgG2b, k |
| Plate_3_D4_242 | RAE1y | CX1 | Rat IgG2b, k |

TABLE 1-continued (Related to FIG. 2) List of surface markers
tested in mouse BM LEGENDScreen ™

| Location | Marker | Clone (Biolegend) | Isotype |
|---|---|---|---|
| Plate_3_D5_243 | CD8b | YTS156.7.7 | Rat IgG2b, k |
| Plate_3_D7_245 | CD126 | D7715A7 | Rat IgG2b, k |
| Plate_3_D8_246 | CD317 | 927 | Rat IgG2b, k |
| Plate_3_D9_247 | CD132 | TUGm2 | Rat IgG2b, k |
| Plate_3_E1_251 | CD88 | 20/70 | Rat IgG2b, k |
| Plate_3_E10_260 | CD130 | 4H1B35 | Rat IgG2b, k |
| Plate_3_E11_261 | CD198 | SA214G2 | Rat IgG2b, k |
| Plate_3_E12_262 | CD20 | SA275A11 | Rat IgG2b, k |
| Plate_3_E2_252 | CD93 | AA4.1 | Rat IgG2b, k |
| Plate_3_E3_253 | CD252 | RM134L | Rat IgG2b, k |
| Plate_3_E4_254 | MD1 | MD-113 | Rat IgG2b, k |
| Plate_3_E5_255 | CD357 | YGITR 765 | Rat IgG2b, k |
| Plate_3_E6_256 | CD185 | L138D7 | Rat IgG2b, k |
| Plate_3_E7_257 | CD37 | Duno85 | Rat IgG2b, k |
| Plate_3_E8_258 | CD300c/d | TX52 | Rat IgG2b, k |
| Plate_3_E9_259 | CD186 (CXCR6) | SA051D1 | Rat IgG2b, k |
| Plate_3_F1_263 | CD124 | I015F8 | Rat IgG2b, k |
| Plate_3_F10_272 | GL7 | GL7 | Rat IgM, k |
| Plate_3_F11_273 | Isotype_SHIgG | SHG-1 | Syrian Hamster IgG |
| Plate_3_F12_274 | CD28 | 37.51 | Syrian Hamster IgG |
| Plate_3_F2_264 | IL23R | 12B2B64 | Rat IgG2b, k |
| Plate_3_F3_265 | CD184 | L276F12 | Rat IgG2b, k |
| Plate_3_F4_266 | CD2 | RM2-5 | Rat IgG2b, λ |
| Plate_3_F5_267 | Isotype_rIgG2c | RTK4174 | Rat IgG2c, k |
| Plate_3_F6_268 | Ly6C | HK1.4 | Rat IgG2c, k |
| Plate_3_F7_269 | Ly6D | 49-H4 | Rat IgG2c, k |
| Plate_3_F8_270 | Isotype_rIgM | RTK2118 | Rat IgM, k |
| Plate_3_F9_271 | CD49b_IgM | DX5 | Rat IgM, k |
| Plate_3_G1_275 | Podoplanin | 8.1.1 | Syrian Hamster IgG |
| Plate_3_G2_276 | CD137 | 17B5 | Syrian Hamster IgG |
| Plate_3_G3_277 | CD278 | 15F9 | Syrian Hamster IgG |
| Plate_3_G4_278 | KLRG1 | 2F1/KLRG1 | Syrian Hamster IgG |
| Plate_3_G5_279 | Ly49CFIH | 14B11 | Syrian Hamster IgG |

35

TABLE 2

(related to FIG. 2). Cell type identification of PhenoGraph clusters

| Phenograph | Label | Markers |
|---|---|---|
| 1 | Transitional Pre-Monocytes (tpMo) | $CD184^{hi}$, $Ly6C^{hi}$, CD115, CX3CR1, $CD62L^{hi}$ |
| 2 | Pro B cells | B220, CD19, $CD16/32^{lo}$, $CD48^{lo}$ |
| 3 | cMoP, tpMo | CD34, Ly6C, CD115, CD62L |
| 4 | IgM+ B Cells | IgM, B220 |
| 5 | Dendritic Cells/preDCs | FLT3, CD11c, SiglecH, IFNAR1, CD317 |
| 6 | Eosinophils | SiglecF, F4/80, CD41 |
| 7 | NK, T cells, NKT cells | NK1.1, CD3, NKG2D |
| 8 | Megakaryocytes | CD41, CD61, $SSC^{hi}$ |
| 9 | Immature Neutrophils | CD371, CD63, Ly6G, CD81 |
| 10 | Mature Neutrophils | $CD182^{hi}$, Ly6G, Gr1, CD11b |
| 11 | Classical monocytes ($Ly6C^{hi}$ Monocytes) | CD115, Ly6C, CD11b |
| 12 | Mature Neutrophils | $CD182^{hi}$, Ly6G, Gr1, CD11b |
| 13 | Mature Neutrophils | $CD182^{hi}$, Ly6G, Gr1, CD11b |
| 14 | Recirculating/Aged Neutrophils | $CD43^{lo}$, Ly6G, $CD11b^{hi}$, $CD62L^{lo}$, $CD182^{lo}$ |
| 15 | Basophils, Mast cells | CD220R, CD49b, IL33R, $CD16/32^{hi}$, cKit, CD123 |
| 16 | $Ly6C^{hi}$ Monocytes downregulated in CD115 during harvest | CD115, Ly6C, CD11b |
| 17 | Mature Neutrophils | $CD182^{hi}$, Ly6G, Gr1, CD11b |
| 18 | HSPCs | cKit, Sca-1, Flt3, CD48, CD11b- |
| 19 | Pre-pro B Cells | $B220^{lo}$, CD2-, CD14, CD19-, CD103 |

TABLE 2-continued (related to FIG. 2). Cell type identification of PhenoGraph clusters

| Phenograph | Label | Markers |
|---|---|---|
| 20 | Stromal Cells | CD140a, CD140b, CD45−, CD144 |
| 21 | Transitional Pre-Monocytes (tpMo) | CD184$^{hi}$, Ly6C$^{hi}$, CD115, CX3CR1, CD62L$^{hi}$ |
| 22 | Red Blood Cells | CD147, Ter119 |
| 23 | pre-Neutrophils | cKit, Gr1, CD11b, CD43, Ly6C |
| 24 | Ly6C− Monocytes (non-classical monocytes) | CD43, CD115, CX3CR1, CD11c |
| 25 | Recirculating Ly6C$^{hi}$ Classical Monocytes | Ly6C, CX3CR1, CD62L, CD16/32, CD115 |
| 26 | pre B cells | CD16/32$^{hi}$, B220, CD19 |
| 27 | IgD+ B cells | IgD, B220 |

TABLE 3

(Related to FIG. 7). List of surface markers tested
in human cord blood LEGENDScreen ™.

| Location | Marker | Clone | Isotype |
|---|---|---|---|
| Plate_1_A1_001 | Blank | | |
| Plate_1_A10_009 | CD2 | RPA-2.10 | mouse IgG1, k |
| Plate_1_A12_011 | B7-H4 | MIH43 | mouse IgG1, k |
| Plate_1_A3_003 | CCR10 | 6588-5 | Armenian Hamster IgG |
| Plate_1_A4_004 | CD278 | C398.4A | Armenian Hamster IgG |
| Plate_1_A5_005 | IFN-γ R b chain | 2HUB-159 | Hamster IgG |
| Plate_1_A7_006 | CD46 | TRA-2-10 | Mouse IgG1 |
| Plate_1_A8_007 | CD70 | 113-16 | Mouse IgG1 |
| Plate_1_A9_008 | CD1a | HI149 | mouse IgG1, k |
| Plate_1_B1_012 | Cadherin 11 | 16G5 | mouse IgG1, k |
| Plate_1_B10_021 | CD111 | R1.302 | mouse IgG1, k |
| Plate_1_B11_022 | CD112 | TX31 | mouse IgG1, k |
| Plate_1_B12_023 | CD114 | LMM741 | mouse IgG1, k |
| Plate_1_B2_013 | CD10 | HI10a | mouse IgG1, k |
| Plate_1_B3_014 | CD100 | A8 | mouse IgG1, k |
| Plate_1_B4_015 | CD103 | Ber-ACT8 | mouse IgG1, k |
| Plate_1_B5_016 | CD105 (Endoglin) | SN6h | mouse IgG1, k |
| Plate_1_B6_017 | CD106 | STA | mouse IgG1, k |
| Plate_1_B7_018 | CD107a | H4A3 | mouse IgG1, k |
| Plate_1_B8_019 | CD107b | H4B4 | mouse IgG1, k |
| Plate_1_B9_020 | CD109 | W7C5 | mouse IgG1, k |
| Plate_1_C1_024 | CD116 | 4H1 | mouse IgG1, k |
| Plate_1_C10_033 | CD13 | WM15 | mouse IgG1, k |
| Plate_1_C11_034 | CD131 | 1C1 | mouse IgG1, k |
| Plate_1_C12_035 | CD134 | Ber-ACT35 (ACT35) | mouse IgG1, k |
| Plate_1_C2_025 | CD117 | 104D2 | mouse IgG1, k |
| Plate_1_C3_026 | CD119 | GIR-208 | mouse IgG1, k |
| Plate_1_C4_027 | CD11a | HI111 | mouse IgG1, k |
| Plate_1_C5_028 | CD11b | ICRF44 | mouse IgG1, k |
| Plate_1_C6_029 | CD122 | TU27 | mouse IgG1, k |
| Plate_1_C7_030 | CD123 | 6H6 | mouse IgG1, k |
| Plate_1_C8_031 | CD126 | UV4 | mouse IgG1, k |
| Plate_1_C9_032 | CD127 | A019D5 | mouse IgG1, k |
| Plate_1_D1_036 | CD135 | BV10A4H2 | mouse IgG1, k |
| Plate_1_D10_045 | CD143 | 5-369 | mouse IgG1, k |
| Plate_1_D11_046 | CD146 | P1H12 | mouse IgG1, k |
| Plate_1_D12_047 | CD148 | A3 | mouse IgG1, k |
| Plate_1_D2_037 | CD137 | 4B4-1 | mouse IgG1, k |
| Plate_1_D3_038 | 4-1BB Ligand | 5F4 | mouse IgG1, k |
| Plate_1_D4_039 | CD138 | MI15 | mouse IgG1, k |
| Plate_1_D5_041 | CD14 | 63D3 | mouse IgG1, k |
| Plate_1_D6_040 | CD140a | 16A1 | mouse IgG1, k |
| Plate_1_D7_042 | CD140b | 18A2 | mouse IgG1, k |
| Plate_1_D8_043 | CD141 | M80 | mouse IgG1, k |
| Plate_1_D9_044 | CD142 | NY2 | mouse IgG1, k |
| Plate_1_E1_048 | CD15 | W6D3 | mouse IgG1, k |
| Plate_1_E10_057 | CD163 | GHI/61 | mouse IgG1, k |
| Plate_1_E11_058 | CD164 | 67D2 | mouse IgG1, k |
| Plate_1_E12_059 | CD165 | SN2 (N6-D11) | mouse IgG1, k |
| Plate_1_E2_049 | CD150 | A12 (7D4) | mouse IgG1, k |
| Plate_1_E3_050 | CD151 | 50-6 | mouse IgG1, k |
| Plate_1_E4_051 | CD154 | 24-31 | mouse IgG1, k |
| Plate_1_E5_052 | CD156c | SHM14 | mouse IgG1, k |

TABLE 3-continued (Related to FIG. 7). List of surface markers tested
in human cord blood LEGENDScreen ™.

| Location | Marker | Clone | Isotype |
| --- | --- | --- | --- |
| Plate_1_E6_053 | CD158e1 | DX9 | mouse IgG1, k |
| Plate_1_E7_054 | CD16 | 3G8 | mouse IgG1, k |
| Plate_1_E8_055 | CD161 | HP-3G10 | mouse IgG1, k |
| Plate_1_E9_056 | CD162 | KPL-1 | mouse IgG1, k |
| Plate_1_F1_060 | CD166 | 3A6 | mouse IgG1, k |
| Plate_1_F10_069 | CD180 | MHR73-11 | mouse IgG1, k |
| Plate_1_F11_070 | CD182 | 5E8/CXCR2 | mouse IgG1, k |
| Plate_1_F12_071 | CD183 | G025H7 | mouse IgG1, k |
| Plate_1_F2_061 | CD169 | 7-239 | mouse IgG1, k |
| Plate_1_F3_062 | CD170 | 1A5 | mouse IgG1, k |
| Plate_1_F4_063 | CD172a/b (SIRPα/β) | SE5A5 | mouse IgG1, k |
| Plate_1_F5_064 | CD172g (SIRPγ) | LSB2.20 | mouse IgG1, k |
| Plate_1_F6_065 | CD178 | NOK-1 | mouse IgG1, k |
| Plate_1_F7_066 | CD179a | HSL96 | mouse IgG1, k |
| Plate_1_F8_067 | CD179b | HSL11 | mouse IgG1, k |
| Plate_1_F9_068 | CD18 | TS1/18 | mouse IgG1, k |
| Plate_1_G1_072 | CD185 | J252D4 | mouse IgG1, k |
| Plate_1_G10_081 | CD203c | NP4D6 | mouse IgG1, k |
| Plate_1_G11_082 | CD205 | HD83 | mouse IgG1, k |
| Plate_1_G12_083 | CD206 | 15-2 | mouse IgG1, k |
| Plate_1_G2_073 | CD19 | HIB19 | mouse IgG1, k |
| Plate_1_G3_074 | CD191 | 5F10B29 | mouse IgG1, k |
| Plate_1_G4_075 | CD194 | L291H4 | mouse IgG1, k |
| Plate_1_G5_076 | CD1b | SN13 (K5-1B8) | mouse IgG1, k |
| Plate_1_G6_077 | CD1c | L161 | mouse IgG1, k |
| Plate_1_G7_078 | CD200 | OX-104 | mouse IgG1, k |
| Plate_1_G8_079 | CD200R | OX-108 | mouse IgG1, k |
| Plate_1_G9_080 | CD202b | 33.1 (Ab33) | mouse IgG1, k |
| Plate_1_H10_093 | CD229 | HLy-9.1.25 | mouse IgG1, k |
| Plate_1_H11_094 | CD23 | EBVCS-5 | mouse IgG1, k |
| Plate_1_H2_085 | CD21 | Bu32 | mouse IgG1, k |
| Plate_1_H3_086 | CD213α1 | SS12B | mouse IgG1, k |
| Plate_1_H4_087 | CD213α2 | SHM38 | mouse IgG1, k |
| Plate_1_H5_088 | CD218a | H44 | mouse IgG1, k |
| Plate_1_H6_089 | CD221 | 1H7/CD221 | mouse IgG1, k |
| Plate_1_H7_090 | CD223 (LAG-3) | 11C3C65 | mouse IgG1, k |
| Plate_1_H8_091 | CD226 | 11A8 | mouse IgG1, k |
| Plate_1_H9_092 | CD227 | 16A | mouse IgG1, k |
| Plate_2_A10_009 | CD268 | 11C1 | mouse IgG1, k |
| Plate_2_A11_010 | CD27 | M-T271 | mouse IgG1, k |
| Plate_2_A2_001 | CD244 (2B4) | C1.7 | mouse IgG1, k |
| Plate_2_A3_002 | CD245 | DY12 | mouse IgG1, k |
| Plate_2_A4_003 | CD25 | M-A251 | mouse IgG1, k |
| Plate_2_A5_004 | CD252 | 11C3.1 | mouse IgG1, k |
| Plate_2_A6_005 | CD261 | DJR1 | mouse IgG1, k |
| Plate_2_A7_006 | CD262 | DJR2-4 (7-8) | mouse IgG1, k |
| Plate_2_A8_007 | CD263 | DJR3 | mouse IgG1, k |
| Plate_2_A9_008 | CD266 | ITEM-1 | mouse IgG1, k |
| Plate_2_B1_012 | CD275 | 9F.8A4 | mouse IgG1, k |
| Plate_2_B10_021 | CD30 | BY88 | mouse IgG1, k |
| Plate_2_B11_022 | CD300c | TX45 | mouse IgG1, k |
| Plate_2_B12_023 | CD309 | 7D4-6 | mouse IgG1, k |
| Plate_2_B2_013 | CD276 | MIH42 | mouse IgG1, k |
| Plate_2_B3_014 | CD277 | BT3.1 | mouse IgG1, k |
| Plate_2_B4_015 | CD279 | EH12.2H7 | mouse IgG1, k |
| Plate_2_B5_016 | CD28 | CD28.2 | mouse IgG1, k |
| Plate_2_B6_017 | CD29 | TS2/16 | mouse IgG1, k |
| Plate_2_B7_018 | CD290 | 3C10C5 | mouse IgG1, k |
| Plate_2_B8_019 | CD298 | LNH-94 | mouse IgG1, k |
| Plate_2_B9_020 | CD3 | UCHT1 | mouse IgG1, k |
| Plate_2_C1_024 | CD31 | WM59 | mouse IgG1, k |
| Plate_2_C10_033 | CD336 | P44-8 | mouse IgG1, k |
| Plate_2_C11_034 | CD337 | P30-15 | mouse IgG1, k |
| Plate_2_C12_035 | CD34 | 581 | mouse IgG1, k |
| Plate_2_C2_025 | CD314 | 1D11 | mouse IgG1, k |
| Plate_2_C3_026 | CD317 | RS38E | mouse IgG1, k |
| Plate_2_C4_027 | CD324 | 67A4 | mouse IgG1, k |
| Plate_2_C5_028 | CD325 | 8C11 | mouse IgG1, k |
| Plate_2_C6_029 | CD328 | 6-434 | mouse IgG1, k |
| Plate_2_C7_030 | CD33 | WM53 | mouse IgG1, k |
| Plate_2_C8_031 | CD334 | 4FR6D3 | mouse IgG1, k |
| Plate_2_C9_032 | CD335 | 9E2 | mouse IgG1, k |
| Plate_2_D1_036 | CD340 | 24D2 | mouse IgG1, k |
| Plate_2_D10_045 | CD38 | HIT2 | mouse IgG1, k |
| Plate_2_D11_046 | CD39 | A1 | mouse IgG1, k |

TABLE 3-continued (Related to FIG. 7). List of surface markers tested
in human cord blood LEGENDScreen ™.

| Location | Marker | Clone | Isotype |
| --- | --- | --- | --- |
| Plate_2_D12_047 | CD4 | RPA-T4 | mouse IgG1, k |
| Plate_2_D2_037 | CD344 | CH3A4A7 | mouse IgG1, k |
| Plate_2_D3_038 | CD35 | E11 | mouse IgG1, k |
| Plate_2_D4_039 | CD354 | TREM-26 | mouse IgG1, k |
| Plate_2_D5_040 | CD360 | 17A12 | mouse IgG1, k |
| Plate_2_D6_041 | CD365 | 1D12 | mouse IgG1, k |
| Plate_2_D7_042 | CD366 | F38-2E2 | mouse IgG1, k |
| Plate_2_D8_043 | CLEC4A | 9E8 | mouse IgG1, k |
| Plate_2_D9_044 | CD36L1 | m1b9 | mouse IgG1, k |
| Plate_2_E1_048 | CD40 | 5C3 | mouse IgG1, k |
| Plate_2_E10_057 | CD49b | P1E6-C5 | mouse IgG1, k |
| Plate_2_E11_058 | CD49c | ASC-1 | mouse IgG1, k |
| Plate_2_E12_059 | CD49d | 9F10 | mouse IgG1, k |
| Plate_2_E2_049 | CD41 | HIP8 | mouse IgG1, k |
| Plate_2_E3_050 | CD42b | HIP1 | mouse IgG1, k |
| Plate_2_E4_051 | CD43 | CD43-10G7 | mouse IgG1, k |
| Plate_2_E5_052 | CD44 | BJ18 | mouse IgG1, k |
| Plate_2_E6_053 | CD45 | HI30 | mouse IgG1, k |
| Plate_2_E7_054 | CD47 | CC2C6 | mouse IgG1, k |
| Plate_2_E8_055 | CD48 | BJ40 | mouse IgG1, k |
| Plate_2_E9_056 | CD49a | TS2/7 | mouse IgG1, k |
| Plate_2_F1_060 | CD5 | UCHT2 | mouse IgG1, k |
| Plate_2_F10_069 | CD62L | DREG-56 | mouse IgG1, k |
| Plate_2_F11_070 | CD62P | AK4 | mouse IgG1, k |
| Plate_2_F2_061 | CD50 | CBR-IC3/1 | mouse IgG1, k |
| Plate_2_F3_062 | CD54 | HA58 | mouse IgG1, k |
| Plate_2_F4_063 | CD55 | JS11 | mouse IgG1, k |
| Plate_2_F5_064 | CD56 (NCAM) | 5.1H11 | mouse IgG1, k |
| Plate_2_F6_065 | CD58 | TS2/9 | mouse IgG1, k |
| Plate_2_F7_066 | CD6 | BL-CD6 | mouse IgG1, k |
| Plate_2_F8_067 | CD61 | VI-PL2 | mouse IgG1, k |
| Plate_2_G10_081 | CD83 | HB15e | mouse IgG1, k |
| Plate_2_G11_082 | CD85 | 17G10.2 | mouse IgG1, k |
| Plate_2_G12_083 | CD85k | ZM4.1 | mouse IgG1, k |
| Plate_2_G2_073 | CD69 | FN50 | mouse IgG1, k |
| Plate_2_G4_075 | CD74 | LN2 | mouse IgG1, k |
| Plate_2_G5_076 | CD79b | CB3-1 | mouse IgG1, k |
| Plate_2_G6_077 | CD8a | SK1 | mouse IgG1, k |
| Plate_2_G7_078 | CD80 | 2D10 | mouse IgG1, k |
| Plate_2_G8_079 | CD81 | 5A6 | mouse IgG1, k |
| Plate_2_G9_080 | CD82 | ASL-24 | mouse IgG1, k |
| Plate_2_H1_084 | CD87 | VIM5 | mouse IgG1, k |
| Plate_2_H10_093 | CD97 | VIM3b | mouse IgG1, k |
| Plate_2_H11_094 | CD99 | 3B2/TA8 | mouse IgG1, k |
| Plate_2_H12_095 | CXCL16 | 22-19-12 | mouse IgG1, k |
| Plate_2_H2_085 | CD89 | A59 | mouse IgG1, k |
| Plate_2_H3_086 | CD8a | RPA-T8 | mouse IgG1, k |
| Plate_2_H4_087 | CD9 | HI9a | mouse IgG1, k |
| Plate_2_H5_088 | CD90 | 5E10 | mouse IgG1, k |
| Plate_2_H6_089 | CD93 | VIMD2 | mouse IgG1, k |
| Plate_2_H7_090 | CD94 | DX22 | mouse IgG1, k |
| Plate_2_H8_091 | CD95 | DX2 | mouse IgG1, k |
| Plate_2_H9_092 | CD96 | NK92.39 | mouse IgG1, k |
| Plate_3_A10_009 | HVEM | 122 | mouse IgG1, k |
| Plate_3_A11_010 | Ig light chain κ | MHK-49 | mouse IgG1, k |
| Plate_3_A12_011 | IgM | MHM-88 | mouse IgG1, k |
| Plate_3_A2_001 | DLL1 | MHD1-314 | mouse IgG1, k |
| Plate_3_A3_002 | DLL4 | MHD4-46 | mouse IgG1, k |
| Plate_3_A4_003 | DR3 | JD3 | mouse IgG1, k |
| Plate_3_A5_004 | EGFR | AY13 | mouse IgG1, k |
| Plate_3_A6_005 | CD357 | 108-17 | mouse IgG1, k |
| Plate_3_A7_006 | GPR19 | K152D10 | mouse IgG1, k |
| Plate_3_A8_007 | GPR56 | CG4 | mouse IgG1, k |
| Plate_3_A9_008 | HLA-E | 3D12 | mouse IgG1, k |
| Plate_3_B1_012 | CD360 | 2G1-K12 | mouse IgG1, k |
| Plate_3_B10_020 | TNAP | W8B2 | mouse IgG1, k |
| Plate_3_B11_021 | MUC-13 | TCC16 | mouse IgG1, k |
| Plate_3_B12_022 | NKp80 | 5D12 | mouse IgG1, k |
| Plate_3_B2_013 | Integrin α9β1 | Y9A2 | mouse IgG1, k |
| Plate_3_B3_014 | Jagged 2 | MHJ2-523 | mouse IgG1, k |
| Plate_3_B4_015 | Ksp37 | TDA3 | mouse IgG1, k |
| Plate_3_B5_016 | LAP | TW4-2F8 | mouse IgG1, k |
| Plate_3_B6_017 | LY6G6D | 13.8 | mouse IgG1, k |
| Plate_3_B7_018 | MERTK | 590H11G1E3 | mouse IgG1, k |
| Plate_3_B8_019 | MSC | W7C6 | mouse IgG1, k |

TABLE 3-continued (Related to FIG. 7). List of surface markers tested
in human cord blood LEGENDScreen ™.

| Location | Marker | Clone | Isotype |
|---|---|---|---|
| Plate_3_C1_023 | Notch 1 | MHN1-519 | mouse IgG1, k |
| Plate_3_C10_032 | Siglec-8 | 7C9 | mouse IgG1, k |
| Plate_3_C11_033 | Siglec-9 | K8 | mouse IgG1, k |
| Plate_3_C12_034 | SSEA-5 | 8E11 | mouse IgG1, k |
| Plate_3_C2_024 | Notch3 | MHN3-21 | mouse IgG1, k |
| Plate_3_C3_025 | Notch 4 | MHN4-2 | mouse IgG1, k |
| Plate_3_C4_026 | NPC | 57D2 | mouse IgG1, k |
| Plate_3_C5_027 | CD352 | NT-7 | mouse IgG1, k |
| Plate_3_C6_028 | PSMA | LNI-17 | mouse IgG1, k |
| Plate_3_C8_030 | Siglec-10 | 5G6 | mouse IgG1, k |
| Plate_3_C9_031 | CD328 | S7.7 | mouse IgG1, k |
| Plate_3_D1_035 | SUSD2 | W5C5 | mouse IgG1, k |
| Plate_3_D10_044 | VEGFR-3 | 9D9F9 | mouse IgG1, k |
| Plate_3_D12_045 | APCDD1 | 7.13 | mouse IgG2a, k |
| Plate_3_D2_036 | TCR α/β | IP26 | mouse IgG1, k |
| Plate_3_D4_038 | Tim-4 | 9F4 | mouse IgG1, k |
| Plate_3_D5_039 | TLT-2 | MIH61 | mouse IgG1, k |
| Plate_3_D6_040 | TM4SF20 | C9 | mouse IgG1, k |
| Plate_3_D7_041 | TRA-2-49 | TRA-2-49/6E | mouse IgG1, k |
| Plate_3_D8_042 | TRA-2-54 | TRA-2-54/2J | mouse IgG1, k |
| Plate_3_D9_043 | TSLPR | 1B4 | mouse IgG1, k |
| Plate_3_E1_046 | CD272 | MIH26 | mouse IgG2a, k |
| Plate_3_E10_055 | CD155 | TX24 | mouse IgG2a, k |
| Plate_3_E11_056 | CD158b | DX27 | mouse IgG2a, k |
| Plate_3_E12_057 | CD184 | 12G5 | mouse IgG2a, k |
| Plate_3_E2_047 | CD198 | L263G8 | mouse IgG2a, k |
| Plate_3_E3_048 | CCRL2 | K097F7 | mouse IgG2a, k |
| Plate_3_E4_049 | CD102 | CBR-IC2/2 | mouse IgG2a, k |
| Plate_3_E5_050 | CD104 | 58XB4 | mouse IgG2a, k |
| Plate_3_E6_051 | CD124 | G077F6 | mouse IgG2a, k |
| Plate_3_E7_052 | CD130 | 2E1B02 | mouse IgG2a, k |
| Plate_3_E8_053 | CD144 | BV9 | mouse IgG2a, k |
| Plate_3_E9_054 | CD152 (CTLA-4) | BNI3 | mouse IgG2a, k |
| Plate_3_F1_058 | CD186 | K041E5 | mouse IgG2a, k |
| Plate_3_F10_067 | CD26 | BA5b | mouse IgG2a, k |
| Plate_3_F11_068 | CD269 | 19F2 | mouse IgG2a, k |
| Plate_3_F12_069 | CD282 | TL2.1 | mouse IgG2a, k |
| Plate_3_F2_059 | CD192 | K036C2 | mouse IgG2a, k |
| Plate_3_F3_060 | CD197 | G043H7 | mouse IgG2a, k |
| Plate_3_F4_061 | CD199 | L053E8 | mouse IgG2a, k |
| Plate_3_F5_062 | CD209 | 9E9A8 | mouse IgG2a, k |
| Plate_3_F6_063 | CD217 | W15177A | mouse IgG2a, k |
| Plate_3_F7_064 | CD230 (Prion) | 3F4 | mouse IgG2a, k |
| Plate_3_F8_065 | CD24 | ML5 | mouse IgG2a, k |
| Plate_3_F9_066 | CD243 | UIC2 | mouse IgG2a, k |
| Plate_3_G1_070 | CD284 | HTA125 | mouse IgG2a, k |
| Plate_3_G10_078 | CD370 | 8F9 | mouse IgG2a, k |
| Plate_3_G11_079 | CD371 | 50C1 | mouse IgG2a, k |
| Plate_3_G12_080 | CD45RO | UCHL1 | mouse IgG2a, k |
| Plate_3_G2_071 | CD301 | H037G3 | mouse IgG2a, k |
| Plate_3_G3_072 | CD303 | 201A | mouse IgG2a, k |
| Plate_3_G4_073 | CD304 | 12C2 | mouse IgG2a, k |
| Plate_3_G5_074 | CD307e | 509f6 | mouse IgG2a, k |
| Plate_3_G6_093 | CD323 | SHM33 | mouse IgG2a, k |
| Plate_3_G7_075 | CD357 | 108-17 | mouse IgG2a, k |
| Plate_3_G8_076 | CD36 | 5-271 | mouse IgG2a, k |
| Plate_3_G9_077 | CD369 | 15E2 | mouse IgG2a, k |
| Plate_3_H1_081 | CD51 | NKI-M9 | mouse IgG2a, k |
| Plate_3_H10_090 | Ganglioside GD2 | 14G2a | mouse IgG2a, k |
| Plate_3_H11_091 | GPR83 | K07JP05 | mouse IgG2a, k |
| Plate_3_H12_092 | HLA-A, B, C | W6/32 | mouse IgG2a, k |
| Plate_3_H2_082 | CD59 | p282 (H19) | mouse IgG2a, k |
| Plate_3_H3_083 | CD7 | CD7-6B7 | mouse IgG2a, k |
| Plate_3_H4_084 | CD71 | CY1G4 | mouse IgG2a, k |
| Plate_3_H5_085 | CD84 | CD84.1.21 | mouse IgG2a, k |
| Plate_3_H6_086 | CD88 | S5/1 | mouse IgG2a, k |
| Plate_3_H7_087 | CD355 | Cr24.1 | mouse IgG2a, k |
| Plate_3_H8_088 | erbB3 | 1B4C3 | mouse IgG2a, k |
| Plate_3_H9_089 | FPR3 | K102B9 | mouse IgG2a, k |
| Plate_4_A10_010 | SUSD2 | W3D5 | mouse IgG2a, k |
| Plate_4_A11_011 | Notch 2 | MHN2-25 | mouse IgG2a, k |
| Plate_4_A12_012 | TACSTD2 | NY18 | mouse IgG2a, k |
| Plate_4_A2_002 | HLA-DR | L243 | mouse IgG2a, k |
| Plate_4_A3_003 | Ig light chain λ | MHL-38 | mouse IgG2a, k |
| Plate_4_A4_004 | IgD | IA6-2 | mouse IgG2a, k |

TABLE 3-continued (Related to FIG. 7). List of surface markers tested
in human cord blood LEGENDScreen ™.

| Location | Marker | Clone | Isotype |
|---|---|---|---|
| Plate_4_A5_005 | IL-28RA | MHLICR2a | mouse IgG2a, k |
| Plate_4_A6_006 | integrin β5 | AST-3T | mouse IgG2a, k |
| Plate_4_A7_007 | KLRG1 | SA231A2 | mouse IgG2a, k |
| Plate_4_A8_008 | LOX-1 | 15C4 | mouse IgG2a, k |
| Plate_4_A9_009 | MICA/MICB | 6D4 | mouse IgG2a, k |
| Plate_4_B1_013 | TIGIT (VSTM3) | A15153G | mouse IgG2a, k |
| Plate_4_B10_021 | CD196 | G034E3 | mouse IgG2b, k |
| Plate_4_B11_022 | CD1d | 51.1 | mouse IgG2b, k |
| Plate_4_B12_023 | CD20 | 2H7 | mouse IgG2b, k |
| Plate_4_B3_014 | C3aR | hC3aRZ8 | mouse IgG2b, k |
| Plate_4_B4_015 | CCX-CKR (CCRL1) | 13E11 | mouse IgG2b, k |
| Plate_4_B5_016 | CD11c | S-HCL-3 | mouse IgG2b, k |
| Plate_4_B6_017 | CD129 | AH9R7 | mouse IgG2b, k |
| Plate_4_B7_018 | CD158 | HP-MA4 | mouse IgG2b, k |
| Plate_4_B8_019 | CD181 | 8F1/CXCR1 | mouse IgG2b, k |
| Plate_4_B9_020 | CD193 | 5E8 | mouse IgG2b, k |
| Plate_4_C1_024 | CD22 | S-HCL-1 | mouse IgG2b, k |
| Plate_4_C10_033 | CD368 | 9B9 | mouse IgG2b, k |
| Plate_4_C11_034 | CD45RA | HI100 | mouse IgG2b, k |
| Plate_4_C12_035 | CD45RB | MEM-55 | mouse IgG2b, k |
| Plate_4_C2_025 | CD220 | B6.220 | mouse IgG2b, k |
| Plate_4_C3_026 | CD235ab | HIR2 | mouse IgG2b, k |
| Plate_4_C4_027 | CD258 | T5-39 | mouse IgG2b, k |
| Plate_4_C5_028 | CD274 | 29E.2A3 | mouse IgG2b, k |
| Plate_4_C6_029 | CD319 | 162.1 | mouse IgG2b, k |
| Plate_4_C7_030 | CD32 | FUN-2 | mouse IgG2b, k |
| Plate_4_C8_031 | CD326 | 9C4 | mouse IgG2b, k |
| Plate_4_C9_032 | CD338 | 5D3 | mouse IgG2b, k |
| Plate_4_D1_036 | CD49e | NKI-SAM-1 | mouse IgG2b, k |
| Plate_4_D10_045 | Dopamine Receptor D1 (DRD1) | L205G1 | mouse IgG2b, k |
| Plate_4_D11_046 | EphA2 | SHM16 | mouse IgG2b, k |
| Plate_4_D12_047 | FcεRIα | AER-37 (CRA-1) | mouse IgG2b, k |
| Plate_4_D2_037 | CD52 | HI186 | mouse IgG2b, k |
| Plate_4_D3_038 | CD66a/c/e | ASL-32 | mouse IgG2b, k |
| Plate_4_D4_039 | CD85h | 24 | mouse IgG2b, k |
| Plate_4_D5_040 | CD85 | GHI/75 | mouse IgG2b, k |
| Plate_4_D6_041 | CD86 | IT2.2 | mouse IgG2b, k |
| Plate_4_D7_042 | CD92 | VIM15b | mouse IgG2b, k |
| Plate_4_D8_043 | CXCR7 | 8F11-M16 | mouse IgG2b, k |
| Plate_4_D9_044 | Delta Opioid Receptor | DOR7D2A4 | mouse IgG2b, k |
| Plate_4_E1_048 | GARP | 7B11 | mouse IgG2b, k |
| Plate_4_E10_056 | SSEA-4 | MC-813-70 | Mouse IgG3, k |
| Plate_4_E12_057 | Sialyl Lewis X (dimeric) | FH6 | Mouse IgM, k |
| Plate_4_E2_049 | CD215 | JM7A4 | mouse IgG2b, k |
| Plate_4_E3_050 | Lymphotoxin β Receptor | 31G4D8 | mouse IgG2b, k |
| Plate_4_E4_051 | MRGX2 | K125H4 | mouse IgG2b, k |
| Plate_4_E5_052 | TMEM8A | SA065C3 | mouse IgG2b, k |
| Plate_4_E6_053 | CD254 | MIH24 | mouse IgG2b, k |
| Plate_4_E7_054 | CD318 | CUB1 | mouse IgG2b, k |
| Plate_4_E9_055 | CD255 | CARL-1 | Mouse IgG3, k |
| Plate_4_F1_058 | TRA-1-81 | TRA-1-81 | Mouse IgM, k |
| Plate_4_F10_066 | CD120b | 3G7A02 | Rat IgG2a, k |
| Plate_4_F11_067 | CD210 | 3F9 | Rat IgG2a, k |
| Plate_4_F12_068 | CD267 | 1A1 | Rat IgG2a, k |
| Plate_4_F2_059 | CD160 | BY55 | Mouse IgM, k |
| Plate_4_F3_060 | CD57 | HNK-1 | Mouse IgM, k |
| Plate_4_F4_061 | CD66b | G10F5 | Mouse IgM, k |
| Plate_4_F5_062 | TRA-1-60-R | TRA-1-60-R | Mouse IgM, k |
| Plate_4_F7_063 | CD115 | 9-4D2-1E4 | Rat IgG1, k |
| Plate_4_F8_064 | CD201 | RCR-401 | Rat IgG1, k |
| Plate_4_G1_069 | CD294 | BM16 | Rat IgG2a, k |
| Plate_4_G10_077 | CD132 | TUGh4 | Rat IgG2b, k |
| Plate_4_G11_078 | CD195 | J418F1 | Rat IgG2b, k |
| Plate_4_G12_079 | CX3CR1 | 2A9-1 | Rat IgG2b, k |
| Plate_4_G2_070 | CD49f | GoH3 | Rat IgG2a, k |
| Plate_4_G3_071 | CD85 | MKT5.1 | Rat IgG2a, k |
| Plate_4_G4_072 | CD85d | 42D1 | Rat IgG2a, k |
| Plate_4_G5_073 | IgG Fc | M1310G05 | Rat IgG2a, k |
| Plate_4_G6_074 | Integrin β7 | FIB504 | Rat IgG2a, k |
| Plate_4_G7_075 | XCR1 | S15046E | Rat IgG2a, k |
| Plate_4_G8_076 | Podoplanin | NC-08 | Rat IgG2a, l |
| Plate_4_H2_080 | SSEA-3 | MC-631 | Rat IgM, k |

TABLE 4

| REAGENT | SOURCE | IDENTIFIER |
|---|---|---|
| | | Antibodies |
| B220 (Clone RA3-6B2) | Thermo Fisher | Cat# 25-0452; RRID: AB_2341160 |
| CD81 (Clone Eat-2) | Biolegend | Cat# 104906, RRID: AB_2076266 |
| CD106 (Clone 429 (MVCAM.A)) | Biolegend | Cat# 105716, RRID: AB_1595489 |
| cKit (Clone 2B8) | Thermo Fisher | Cat# 62-1171-82, RRID: AB_2637141 |
| CD11b (Clone M1/70) | Thermo Fisher | Cat# 63-0112-80, RRID: AB_2637407 |
| CD115 (Clone AFS98) | Biolegend | Cat# 135510, RRID: AB_2085221 |
| Flt3 (Clone A2F10) | Biolegend | Cat# 135308, RRID: AB_1953267 |
| NK1.1 (Clone PK136) | Thermo Fisher | Cat# 13-5941-81, RRID: AB_466803 |
| B220 (Clone RA3-6B2) | Thermo Fisher | Cat# 13-0452-82, RRID: AB_466449 |
| CD90.2 (Clone 53-2.1) | Biolegend | Cat# 140314, RRID: AB_10643274 |
| F4/80 (Clone BM8) | Biolegend | Cat# 123118, RRID: AB_893477 |
| CD16/32 (Clone 2.4G2) | BD Horizon | Cat# 565502, RRID: AB_2739269 |
| CD34 (Clone RAM34) | Thermo Fisher | Cat# 13-0341-81, RRID: AB_466424 |
| Gr1 (Clone RB6-8C5) | Thermo Fisher | Cat# 45-5931-80; RRID: AB_906247 |
| Ly6C (Clone HK1.4) | Biolegend | Cat# 128026; RRID: AB_10640120 |
| Ly6G (Clone 1A8) | Biolegend | Cat# 127618; RRID: AB_1877261 |
| Sca-1 (Clone D7) | Biolegend | Cat# 108114; RRID: AB_493596 |
| Siglec-F (Clone E50-2440) | BD Biosciences | Cat# 562757; RRID: AB_394341 |
| CXCR2 (Clone SA044G4) | Biolegend | Cat# 149306; RRID: AB_2565694 |
| CXCR4 (Clone 2B11) | Thermo Fisher | Cat# 13-9991-82; RRID: AB_10609202 |
| CD45.1 (Clone A20) | Biolegend | Cat#110707; RRID: AB_313496 |
| CD45.2 (Clone 104) | Biolegend | Cat#109807; RRID: AB_313444 |
| CD3 (Clone UCHT1) | Biolegend | Cat#300440; RRID: AB_2562046 |
| CD10 (Clone HI10a) | Biolegend | Cat#312208; RRID: AB_314919 |
| CD19 (Clone HIB19) | Biolegend | Cat#302205; RRID: AB_314235 |
| CD56 (Clone HCD56) | Biolegend | Cat#318304; RRID: AB_604100 |
| CD14 (Clone M5E2) | Biolegend | Cat#301838; RRID: AB_2562909 |
| CD15 (Clone HI98) | BD Biosciences | Cat#564232; RRID: AB_2738686 |
| CD49d (Clone 9F10) | BD Biosciences | Cat#563645; RRID: AB_2738344 |
| CD66b (Clone G105F) | BD Biosciences | Cat#305111; RRID: AB_2563293 |
| CD101 (Clone BB27) | Biolegend | Cat#331007; RRID: AB_2121761 |
| CD16 (Clone 3G8) | BD Biosciences | Cat#560248; RRID: AB_1645467 |
| CD34 (Clone 581) | Biolegend | Cat#343515; RRID: AB_1877252 |
| CD117 (Clone 104D2) | Thermo Fisher | Cat#64-1178-42; RRID: AB_2734860 |
| CD45 (Clone 2D1) | Biolegend | Cat368515; RRID: AB_2566375 |
| CD11b (ICRF44) | BD Biosciences | Cat#563839; RRID: AB_2716869 |
| CD38 (S17015F) | Biolegend | Cat#303531; RRID: AB_2561527 |
| CD71 (CY1G4) | Biolegend | Cat#334106; RRID: AB_2201481 |
| Chemicals, Peptides, and Recombinant Proteins | | |
| 1X RBC Lysis Buffer | eBioscience | Cat# 00-4333-57 |
| 5-Fluorouracil | Sigma-Aldrich | Cat# F6627 |
| CountBright Absolute Counting Beads | Life Technologies | Cat# C36950 |
| DAPI | Life Technologies | Cat# D1306 |
| Hema 3 Manual Staining System | Thermo Fisher | Cat# 22-122911 |
| EQ Four Element Calibration Beads | Fluidigm | Cat# 201078 |
| Human G-CSF (Neupogen) | Amgen | Cat# 100696800 |
| MethoCult ™ M3234 | Stem Cell Technologies | Cat# 03234 |
| StemSpan ™ SFEM II | Stem Cell Technologies | Cat# 09655 |
| Critical Commercial Assays | | |
| ERCC RNA Spike-In Mix | Thermo Fisher | Cat# 4456740 |
| MILLIPLEX MAP Mouse Cytokine/Chemokine Magnetic Bead Panel - Premixed 32 Plex - Immunology Multiplex Assay | Merck | Cat# MCYTMAG-70K-PX32 |
| LEGENDScreen ™ Human Kit | Biolegend | Cat# 700007 |

TABLE 4-continued

Key resources table

| REAGENT | SOURCE | IDENTIFIER |
|---|---|---|
| | | Antibodies |
| LEGENDScreen ™ Mouse Kit | Biolegend | Cat# 70000 |
| Arcturus PicoPure RNA isolation kit Deposited Data | Thermo Fisher | Cat# KIT0214 |
| Bulk RNA-seq of myeloid progenitor populations | This disclosure | GEO: |
| Smart-Seq2 Single-cell Dataset of myeloid precursors | This disclosure | GEO: |
| Tabula Muris BM 10× single-cell RNA-seq dataset | (Schaum et al., 2018) | GEO: GSE109774 |
| Single-cell RNA-seq of BM GMPs Experimental Models: Organisms/Strains | (Olsson et al., 2016) | GEO: GSE70240 |
| Mouse: C57BL/6J | The Jackson Laboratory | Stock No: 000664 |
| Mouse: Rosa26$^{mT/mG}$:STOCK Gt(ROSA)$^{26Sortm4(ACTB-tdTomato, -EGFP)Luo}$/J | The Jackson Laboratory | Stock No: 007676 |
| Mouse: Fucci-S/G2/M (#474) | RIKEN BRC, Ibaraki, Japan | Stock No: RBRC02704 |
| Mouse: C57BL/6-Tg(UBC-GFP)30Scha/J; UBI-GFP | The Jackson Laboratory | Stock No: 04353 |
| Mouse: B6.SJL-Ptprc$^a$ Pepc$^b$/BoyJ; B6 Cd45.1 | The Jackson Laboratory | Stock No: 002014 |
| Mouse: Cebpe$^{-/-}$ Software and Algorithms | H. P. Koeffler | (Kyme et al., 2012) |
| GraphPad Prism 7 | GraphPad Software | http://www.graphpad.com |
| FlowJo 10 | TreeStar | http://flowjo.com/ |
| t-SNE | (Van Der Maaten and Hinton, 2008) | https://cran.r-project.org/web/packages/Rtsne/index.html |
| edgeR | (Robinson et al., 2009) | https://bioconductor.org/packages/release/bioc/html/edgeR.html |
| pheatmap | R package | https://cran.r-project.org/web/packages/pheatmap/index.html |
| Enrichr | (Chen et al., 2013) | http://amp.pharm.mssm.edu/Enrichr/ |
| Monocle 2 | (Qiu et al., 2017) | http://cole-trapnell-lab.github.io/monocle-release/docs/ |
| Seurat v3 | (Stuart et al., 2018) | https://github.com/satijalab/seurat |
| UMAP | (McInnes et al., 2018) | https://umap-learn.readthedocs.io/en/latest/ |
| SVM regression used in InfinityFlow | The R foundation | https://cran.r-project.org/web/packages/e1071/ |
| R 3.6 | The R foundation | https://www.r-project.org/ |

REFERENCES

Akashi, K., Traver, D., Miyamoto, T., and Weissman, I. L. (2000). A clonogenic common myeloid progenitor that gives rise to all myeloid lineages. Nature 404, 193-197.

Arinobu, Y., Iwasaki, H., Gurish, M. F., Mizuno, S. I., Shigematsu, H., Ozawa, H., Tenen, D. G., Austen, K. F., and Akashi, K. (2005). Developmental checkpoints of the basophil/mast cell lineages in adult murine hematopoiesis. Proc. Natl. Acad. Sci. U.S.A. 102, 18105-18110.

Becht, E., McInnes, L., Healy, J., Dutertre, C.-A. C.-A., Kwok, I. W. H. I. W. H., Ng, L. G. L. G., Ginhoux, F., and Newell, E. W. E. W. (2018). Dimensionality reduction for visualizing single-cell data using UMAP. Nat. Biotechnol. 37, 38-44.

Chen E Y, Tan C M, Kou Y, Duan O, Wang Z, Meirelles G V, et al. Enrichr: Interactive and collaborative HTML5 gene list enrichment analysis tool. BMC Bioinformatics. 2013 Apr.; 14.

Chong, S. Z., Evrard, M., Devi, S., Chen, J., Lim, J. Y., See, P., Zhang, Y., Adrover, J. M., Lee, B., Tan, L., et al. (2016). CXCR4 identifies transitional bone marrow premonocytes that replenish the mature monocyte pool for peripheral responses. J. Exp. Med. 213, 2293-2314.

Dutertre, C.-A., Becht, E., Erdal, S., Radstake, T., and Newell, E. W. (2019). Single-Cell Analysis of Human Mononuclear Phagocytes Reveals Subset-Defining Markers and Identifies Circulating Inflammatory Dendritic Cells CD14+/Å DC3s d Pro-inflammatory CD14+DC3 expansion correlates with disease activity in SLE patients. Immunity.

Giladi, A., Paul, F., Herzog, Y., Lubling, Y., Weiner, A., Yofe, I., Jaitin, D., Cabezas-Wallscheid, N., Dress, R., Ginhoux, F., et al. (2018). Single-cell characterization of haematopoietic progenitors and their trajectories in homeostasis and perturbed haematopoiesis. Nat. Cell Biol. 20.

Hettinger, J., Richards, D. M., Hansson, J., Barra, M. M., Joschko, A.-C., Krijgsveld, J., and Feuerer, M. (2013). Origin of monocytes and macrophages in a committed progenitor. Nat. Immunol. 14, 821-830.

Kyme P, Thoennissen N H, Tseng C W, Thoennissen G B, Wolf A J, Shimada K, et al. C/EBPE mediates nicotinamide-enhanced clearance of *Staphylococcus aureus* in mice. Journal of Clinical Investigation. 2012 September; 122(9):3316-29.

Iwasaki, H., Mizuno, S., Mayfield, R., Shigematsu, H., Arinobu, Y., Seed, B., Gurish, M. F., Takatsu, K., and Akashi, K. (2005). Identification of eosinophil lineage-committed progenitors in the murine bone marrow. J. Exp. Med. 201, 1891-1897.

Levine, J. H., Simonds, E. F., Bendall, S. C., Downing, J. R., Pe'er, D., and Correspondence, G. P. N. (2015). Data-Driven Phenotypic Dissection of AML Reveals Progenitor-like Cells that Correlate with Prognosis. Cell 162, 184-197.

Maaten, L., and Hinton, G. (2008). Visualizing data using t-SNE. J. Mach. Learn. Res.

McInnes, L., Healy, J., and Melville, J. (2018). UMAP: Uniform Manifold Approximation and Projection for Dimension Reduction.

Olsson, A., Venkatasubramanian, M., Chaudhri, V. K., Aronow, B. J., *Salomonis*, N., Singh, H., Grimes, H. L., and Leighton Grimes, H. (2016). Single-cell analysis of mixed-lineage states leading to a binary cell fate choice. Nature 537, 698-702.

Picelli, S., Faridani, O. R., Björklund, Å. K., Winberg, G., Sagasser, S., and Sandberg, R. (2014). Full-length RNA-seq from single cells using Smart-seq2. Nat. Protoc. 9, 171-181.

Qiu, X., Mao, Q., Tang, Y., Wang, L., Chawla, R., Pliner, H. A., and Trapnell, C. (2017). Reversed graph embedding resolves complex single-cell trajectories. Nat. Methods 14, 979-982.

Rittirsch, D., Huber-Lang, M. S., Flierl, M. A., and Ward, P. A. (2009). Immunodesign of experimental sepsis by cecal ligation and puncture. Nat. Protoc. 4, 31-36.

Robinson, M. D., McCarthy, D. J., and Smyth, G. K. (2009). edgeR: A Bioconductor package for differential expression analysis of digital gene expression data. Bioinformatics 26, 139-140.

Rubinstein, M. P., Salem, M. L., Doedens, A. L., Moore, C. J., Chiuzan, C., Rivell, G. L., Cole, D. J., and Goldrath, A. W. (2013). G-CSF/anti-G-CSF antibody complexes drive the potent recovery and expansion of CD11b+Gr-1+myeloid cells without compromising CD8+T cell immune responses. Journal of Hematology & Oncology 6, 75.

Sakaue-Sawano, A., Kurokawa, H., Morimura, T., Hanyu, A., Hama, H., Osawa, H., Kashiwagi, S., Fukami, K., Miyata, T., Miyoshi, H., et al. (2008). Visualizing Spatiotemporal Dynamics of Multicellular Cell-Cycle Progression. Cell 132, 487-498.

Schaum, N., Karkanias, J., Neff, N. F., May, A. P., Quake, S. R., Wyss-Coray, T., Darmanis, S., Batson, J., Botvinnik, O., Chen, M. B., et al. (2018). Single-cell transcriptomics of 20 mouse organs creates a *Tabula Muris* the *tabula Muris* consortium*.

Stuart, T., Butler, A., Hoffman, P., Hafemeister, C., Papalexi, E., Mauck III, W. M., Stoeckius, M., Smibert, P., and Satija, R. (2018). Comprehensive integration of single cell data. 1-24.

Tomura, M., Sakaue-Sawano, A., Mori, Y., Takase-Utsugi, M., Hata, A., Ohtawa, K., Kanagawa, O., and Miyawaki, A. (2013). Contrasting Quiescent G0 Phase with Mitotic Cell Cycling in the Mouse Immune System. PLoS One 8, e73801-10.

Van Der Maaten L, Hinton G. Visualizing data using t-SNE. Journal of Machine Learning Research. 2008; 9:2579-625.

Yamanaka, R., Barlow, C., Lekstrom-Himes, J., Castilla, L. H., Liu, P. P., Eckhaus, M., Decker, T., Wynshaw-Boris, A., and Xanthopoulos, K. G. (1997). Impaired granulopoiesis, myelodysplasia, and early lethality in CCAAT/enhancer binding protein ε-deficient mice. Proc. Natl. Acad. Sci. U.S.A 94, 13187-13192.

It will be appreciated by a person skilled in the art that other variations and/or modifications may be made to the embodiments disclosed herein without departing from the spirit or scope of the disclosure as broadly described. For example, in the description herein, features of different exemplary embodiments may be mixed, combined, interchanged, incorporated, adopted, modified, included etc. or the like across different exemplary embodiments. The present embodiments are, therefore, to be considered in all respects to be illustrative and not restrictive.

The invention claimed is:

1. A method of identifying neutrophil progenitors, the method comprising:

determining an expression of the following biomarkers: CD71, LOX-1, CD164, CD112, CD181, TACSTD2, CD11b and CD49d in a cell;

identifying the cell as an early neutrophil progenitor when it is determined to have the following expression profiles: CD71$^{hi/+}$, LOX-1$^{int/lo/-}$, CD164$^{hi/+}$, CD112$^{hi/+}$, CD181$^{int/lo/-}$ TACSTD2$^{hi/+}$, CD11b$^{lo/-}$ and CD49d$^{int/hi/+}$;

selecting the cell identified as the early neutrophil progenitor;

determining an expression of the selected cell of a further biomarker CD49d and a side-scatter (SSC) property of the neutrophil progenitor;

identifying the cell as an early committed neutrophil progenitor or an intermediate neutrophil progenitor subtype based on the expression of the further biomarker and the side-scatter property, wherein where the cell is determined to be CD71$^{hi/+}$, CD49d$^{hi/+}$ and SSC$^{lo}$, the cell is identified as an early committed neutrophil progenitor, and wherein where the cell is determined to be CD71$^{hi/+}$, CD49d$^{int/lo/-}$ and SSC$^{hi}$, the cell is identified as an intermediate neutrophil progenitor that is downstream in neutrophil lineage to the early committed neutrophil progenitor, wherein the method further comprising culturing the identified neutrophil progenitors to obtain proliferation and/or differentiation of the neutrophil progenitors to obtain progenies thereof, and administering the neutrophil progenitors and/or the progenies thereof to a subject in need thereof.

2. The method according to claim 1, wherein determination of the expression of the biomarkers and the further biomarker comprises contacting the cell with antibodies against the biomarkers and the further biomarker.

3. A method of sorting and/or separating neutrophil progenitors from a cell population, the method comprising:

selecting the cell having the following expression profiles: $CD71^{hi/+}$, LOX-$1^{int/lo/-}$ $CD164^{hi/+}$, $CD112^{hi/+}$, $CD181^{int/lo/-}$ TACSTD$2^{hi/+}$, $CD11b^{lo/-}$ and $CD49d^{int/hi/+}$;

determining an expression of the selected cells of a further biomarker CD49d and a side-scatter (SSC) property;

identifying the cells as an early committed neutrophil progenitor or an intermediate neutrophil progenitor subtype based on the expression of the further biomarker and the side-scatter property;

sorting and/or separating the identified cells as an early committed neutrophil progenitor having the following expression profiles: $CD71^{hi/+}$, $CD49d^{hi/+}$ and $SSC^{lo}$; and sorting and/or separating the identified cells as an intermediate neutrophil progenitor having the following expression profiles: $CD71^{hi/+}$, $CD49d^{int/lo/-}$ and $SSC^{hi}$.

4. The method according to claim 3, wherein the cell population is derived from cord blood and/or bone marrow.

5. The method according to claim 3, the method further comprising culturing the neutrophil progenitors to obtain proliferation and/or differentiation of the neutrophil progenitors to obtain progenies thereof.

6. The method according to claim 3, the method further comprising administering the neutrophil progenitors and/or the progenies thereof to a subject in need thereof.

7. The method according to claim 6, wherein the subject has neutropenia.

8. The method according to claim 3, wherein the selecting comprises contacting the cells with antibodies against CD71, LOX-1, CD164, CD112, CD181, TACSTD2, CD11b and CD49d.

9. A composition that is enriched in early neutrophil progenitors having the following expression profiles: $CD71^{hi/+}$, $CD49d^{hi/+}$, $SSC^{lo}$, LOX-$1^{int/lo/-}$, $CD164^{hi/+}$, $CD112^{hi/+}$, $CD181^{int/lo/-}$, TACSTD$2^{hi/+}$, and $CD11b^{lo/-}$.

10. The method of claim 3, further comprising preparing a transfusion composition, wherein the composition is an enriched composition of early neutrophil progenitors having $CD71^{hi/+}$ $CD49d^{hi+}$, $SSC^{lo}$LOX-$1^{int/lo/-}$, $CD164^{hi/+}$, $CD112^{hi/+}$, $CD181^{int/lo/-}$, TACSTD$2^{hi/+}$, and $CD11b^{lo/-}$.

11. The composition of claim 9, further comprising an intermediate neutrophil progenitor that is downstream in neutrophil lineage to the early committed neutrophil progenitor having the following expression profile: $CD71^{hi/30}$, $CD49d^{int/lo/-}$ and $SSC^{hi}$.

* * * * *